(12) United States Patent
Boléa et al.

(10) Patent No.: US 8,524,718 B2
(45) Date of Patent: Sep. 3, 2013

(54) HETEROAROMATIC DERIVATIVES AND THEIR USE AS POSITIVE ALLOSTERIC MODULATORS OF METABOTROPIC GLUTAMATE RECEPTORS

(75) Inventors: Christelle Boléa, Geneva (CH); Sylvain Celanire, Geneva (CH)

(73) Assignee: Addex Pharma S.A., Geneva (CH)

( * ) Notice: Subject to any disclaimer, the term of this patent is extended or adjusted under 35 U.S.C. 154(b) by 0 days.

(21) Appl. No.: 13/605,893

(22) Filed: Sep. 6, 2012

(65) Prior Publication Data

US 2012/0329811 A1   Dec. 27, 2012

Related U.S. Application Data

(63) Continuation of application No. 12/452,602, filed as application No. PCT/EP2008/059044 on Jul. 10, 2008, now abandoned.

(30) Foreign Application Priority Data

Jul. 13, 2007   (GB) .................................. 0713687.2
Nov. 28, 2007   (GB) .................................. 0723342.2

(51) Int. Cl.
| | | |
|---|---|---|
| A61K 31/427 | (2006.01) | |
| A61K 31/4155 | (2006.01) | |
| C07D 277/20 | (2006.01) | |
| C07D 231/10 | (2006.01) | |
| C07D 417/04 | (2006.01) | |

(52) U.S. Cl.
USPC ...... 514/255.05; 514/370; 514/406; 548/190; 548/364.1; 548/371.4

(58) Field of Classification Search
USPC ............ 514/370, 406; 548/190, 364.1, 371.4
See application file for complete search history.

(56) References Cited

U.S. PATENT DOCUMENTS

| | | | |
|---|---|---|---|
| 7,105,550 B2 * | 9/2006 | Love et al. ................... 514/365 | |
| 2003/0055085 A1 | 3/2003 | Wagenen et al. | |
| 2005/0272779 A1 | 12/2005 | Edwards et al. | |
| 2007/0105891 A1 | 5/2007 | Jaeschke et al. | |

FOREIGN PATENT DOCUMENTS

| | | |
|---|---|---|
| WO | WO 01/64674 A | 9/2001 |
| WO | WO 03/029210 A | 4/2003 |
| WO | WO 2004/014881 A2 | 2/2004 |
| WO | WO-2005/007096 A2 | 1/2005 |
| WO | WO 2006/002981 A | 1/2006 |
| WO | WO 2006/122011 A | 11/2006 |
| WO | WO 2006/123249 A2 | 11/2006 |
| WO | WO 2006/123257 A2 | 11/2006 |
| WO | WO 2006/126718 A | 11/2006 |
| WO | WO-2007/031440 A2 | 3/2007 |
| WO | WO 2007/037543 A1 | 4/2007 |
| WO | WO 2007/071348 A | 6/2007 |

OTHER PUBLICATIONS

Database Registry [Online] Chemical Abstracts Service, Columbus, Ohio, US ; Feb. 11, 2000, XP002507907 retrieved from STN Database accession No. 255828-23-0.
Database Registry [Online] Chemical Abstracts Service, Columbus, Ohio, US ; Feb. 11, 2000, XP002507908 retrieved from STN Database accession No. 255828-22-9.
Database Registry [Online] Chemical Abstracts Service, Columbus, Ohio, US ; Feb. 11, 2000, XP002507909 retrieved from STN Database accession No. 255828-21-8.
Database Registry [Online] Chemical Abstracts Service, Columbus, Ohio, US ; Feb. 11, 2000, XP002507911 retrieved from STN Database accession No. 255828-19-4.
Database WPI Week 200713, Thomson Scientific, London, GB ; AN 2007-132282 XP002508549, (2006).
Indian Journal of Heterocyclic Chemistry, 2006, vol. 16(2), pp. 155-158.
Indian Journal of Chemistry, Section B: Organic Chemistry Including Medicinal Chemistry, 2001, vol. 40B(7), pp. 636-639.
Russian Chemical Bulletin (Translation of Izvestiya Akademii Nauk, Seriya Khimicheskaya), 2004, vol. 53(3), pp. 676-680.
Chemische Berichte, 1962, vol. 95, pp. 2166-2171.
Journal of Medicinal Chemistry, 2004, vol. 47(20), pp. 4818-4828.
Celanire, S., et al., Dicovery and characterization of novel metabotropic glutamate receptor 4 (mGluR4) positive allosteric modulators. Poster session presented at the 7th International Meeting of Metabotropic Gluatamate Receptors in Taormina, Italy. Oct. 2011.
Battaglia, G., et al., Pharmacological Activation of mGlu4 Metabotropic Glutamate. . . , Journal of Neuroscience, 2006, vol. 26(27), pp. 7222-7229.
Besong, G., et al., Activation of Group III Metabotropic Glutamate Receptors Inhibits the Production of RANTES . . . , Journal of Neuroscience, 2002, vol. 22(13), pp. 5403-5411.

(Continued)

*Primary Examiner* — Yong Chu
(74) *Attorney, Agent, or Firm* — Law Offices of Gerard Bilotto, P.C.; Gerard Bilotto

(57) ABSTRACT

The present invention relates to novel compounds of Formula (I), wherein $X^1$, $X^2$, $X^3$, $X^4$, $Y^1$, $Y^2$, $Y^3$, $Y^4$, $M^1$, $M^2$, $M^3$, $A^m$ and $B^n$ are defined as in Formula (I); invention compounds are modulators of metabotropic glutamate receptors—subtype 4 ("mGluR4") which are useful for the treatment or prevention of central nervous system disorders as well as other disorders modulated by mGluR4 receptors.

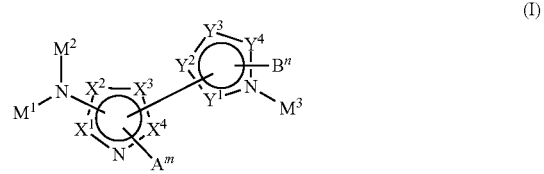

(I)

The invention is also directed to pharmaceutical compositions and the use of such compounds in the manufacture of medicaments, as well as to the use of such compounds for the prevention and treatment of such diseases in which mGluR4 is involved.

5 Claims, No Drawings

(56) References Cited

OTHER PUBLICATIONS

Bradley, S., et al., Immunohistochemical Localization of Subtype 4a Metabotropic Glutamate Receptors . . . , Journal of Comparative Neurology, 1999, vol. 407, pp. 33-46.

Bruno, V., et al., Selective Activation of mGlu4 Metabotropic Glutamate Receptors Is Protective . . . , Journal of Neuroscience, 2000, vol. 20(17), pp. 6413-6420.

Conn, P.J., et al., Metabotropic Glutamate Receptors in the Basal Ganglia Motor Circuit, Nature Review Neuroscience, 2005, vol. 6, pp. 787-798, Nature Publishing Group.

Corti, C., et al., Distribution and Synaptic Localisation of the Metabotropic Glutamate . . . , Neuroscience, 2002, vol. 110(3), pp. 403-420, Elsevier Science Ltd, Great Britain.

Johnson, M.P., et al., Modulation of Stress-Induced and Stimulated Hyperprolactinemia with the Group . . . , Neuropharmacology, 2002, vol. 43, pp. 799-808, Elsevier Science Ltd.

Johnson, M.P., et al., Discovery of Allosteric Potentiators . . . , Journal of Medicinal Chemistry, 2003, vol. 46(15), pp. 3189-3192, American Chemical Society.

Johnson, M.P., et al., Allosteric Modulators of Metabotropic Glutamate Receptors . . . , Biochemical Society Transactions, 2004, vol. 32(5), pp. 881-887, Biochemical Society.

Kew, J., Positive and Negative Allosteric Modulation of Metabotropic Glutamate Receptors . . . , Pharmacology & Therapeutics, 2004, vol. 104(3), pp. 233-244, Elsevier Inc.

Knoflach, F., et al., Positive Allosteric Modulators of Metabotropic Glutamate 1 Receptor . . . , Proc. Natl. Acad. Sci. USA, 2001, vol. 98(23), pp. 13402-13407.

Konieczny, J., et al., the Influence of Group III Metabotropic Glutamate Receptor Stimulation by . . . , Neuroscience, 2007, vol. 145, pp. 611-620, Elsevier Ltd.

Lopez, S., et al., Targeting Group III Metabotropic Glutamate Receptors Produces . . . , Journal of Neuroscience, 2007, vol. 27(25), pp. 6701-6711, Society for Neuroscience.

Maj, M., et al., (−)-PHCCC a Positive Allosteric Modulator of mGluR4: Characterization, Mechanism of Action . . . , Neuropharmacology, 2003, vol. 45, pp. 895-906, Elsevier Ltd.

Marino, M., et al., Allosteric Modulation of Group III Metabotropic Glutamate Receptor 4: a Potential . . . , Proc. Natl. Acad. Sci. USA, 2003, vol. 100(23), pp. 13668-13673.

Marino, M., et al., Targeting the Metabotropic Glutamate Receptor . . . , Current Topics in Medicinal Chemistry, 2005, vol. 5(9), pp. 885-895, Bentham Science Publishers, Ltd.

Marino, M., et al., Localization and Physiological Roles of Metabotropic Glutamate Receptors in the Direct and Indirect . . . , Amino Acids, 2002, vol. 23, pp. 185-191, Austria.

Mathiesen, J., et al., Positive Allosteric Modulation of the Human Metabotropic . . . , British Journal of Pharmacology, 2003, vol. 138(6), pp. 1026-1030, Nature Publishing Group.

Millan, C., et al., Subtype-specific Expression of Group . . . , Journal of Biological Chemistry, 2002, vol. 277(49), pp. 47796-47803, American Soc. Biochem. & Molec. Biology Inc.

Mitsukawa, K., et al., A Selective Metabotropic Glutamate Receptor 7 Agonist: Activation of Receptor . . . , Proc. Natl. Acad. Sci. USA, 2005, vol. 102(51), pp. 18712-18717.

Monastyrskaia, K., et al., Effect of the Umami Peptides on the Ligand Binding and Function . . . , British Journal of Pharmacology, 1999, vol. 128, pp. 1027-1034, Stockton Press.

Mutel, V., Therapeutic Potential of Non-Competitive, Subtype-Selective Metabotropic . . . , Expert Opinion Ther. Patents, 2002, vol. 12(12), pp. 1-8, Ashley Publications Ltd.

Nakanishi, S., et al., Glutamate Receptors: Brain Function and Signal Transduction, Brain Research Reviews, 1998, vol. 26, pp. 230-235, Elsevier Science B.V.

O'Brien, J., et al., A Family of Highly Selective Allosteric . . . , Molecular Pharmacology, 2003, vol. 64(3), pp. 731-740, Amer. Soc. For Pharmacology & Experim. Therapeutics, USA.

Page, A., et al., Metabotropic Glutamate Receptors Inhibit Mechanosensitivity in Vagal . . . , Gastroenterology, 2005, vol. 128, pp. 402-10, American Gastroenterological Assoc.

Ritzen, A., et al., Molecular Pharmacology and Therapeutic Prospects . . . , Basic & Clinical Pharmacol. & Toxicol., 2005, vol. 97, pp. 202-213, Pharmacology & Toxicology, Denmark.

Schoepp, D., et al., Pharmacological Agents Acting at Subtypes of Metabotropic Glutamate Receptors, Neuropharmacology, 1999, vol. 38, pp. 1431-1476, Elsevier Science Ltd.

Stachowicz, K., et al., Anxiolytic-like effects of Phccc, an allosteric modulator of mGlu4 . . . , European Journal of Pharmacology, 2004, vol. 498, pp. 153-156, Elsevier B.V.

Tatarczynska, E., et al., Anxiolytic- and Antidepressant-Like Effects of Group III . . . , Polish Journal of Pharmacol., 2002, vol. 54(6), pp. 707-710, Institute of Pharmacology.

Toyono, T., et al., Expression of the Metabotropic Glutamate Receptor, mGluR4A, in the Taste Hairs of Taste Buds in Rat . . . , Arch. Histol. Cytol., 2002, vol. 65(1), pp. 91-96.

Uehara, S., et al., Metabotropic Glutamate Receptor Type 4 Is Involved in Autoinhibitory Cascade . . . , Diabetes, 2004, vol. 53, pp. 998-1006, American Diabetes Association.

Valenti, O., et al., Group III Metabotropic Glutamate Receptor-Mediated Modulation . . . , Journal of Neuroscience, 2003, vol. 23(18), pp. 7218-7226, Society for Neuroscience.

Valenti, O., et al., Group III Metabotropic . . . , Journal of Pharmacol. & Experim. Therapeutics, 2005, vol. 313(3), pp. 1296-1304, Amer. Soc. For Pharmacol.& Experim. Ther., USA.

Vernon, A., et al., Neuroprotective Effects of Metabotropic . . . , European Journal of Neuroscience, 2005, vol. 22, pp. 1799-1806, Federation of European Neuroscience Societies.

Wilson, J., et al., Identification of Novel Positive Allosteric Modulators of mGlu8 Receptor, Neuropharmacology, 2005, vol. 49, p. 278.

Young, R., et al., Anatomy and Function of Group III Metabotropic Glutamate Receptors in Gastric Vagal Pathways, Neuropharmacology, 2008, vol. 54, pp. 965-975, Elsevier Ltd.

\* cited by examiner

HETEROAROMATIC DERIVATIVES AND THEIR USE AS POSITIVE ALLOSTERIC MODULATORS OF METABOTROPIC GLUTAMATE RECEPTORS

This application is a continuation of U.S. application Ser. No. 12/452,602 filed Jan. 11, 2010, now abandoned, which is a national stage application under U.S.C. §371 of international application PCT/EP2008/059044 filed Jul. 10, 2008, which claims the benefit under 35 U.S.C. 119(a) and 365(b) of UK application Nos. GB0713687.2, filed Jul. 13, 2007, and GB0723342.2, filed Nov. 28, 2007.

SUMMARY OF THE INVENTION

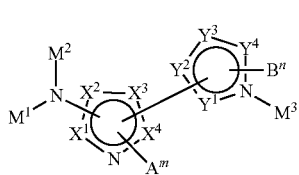

(I)

The present invention relates to novel compounds of Formula (I), wherein $X^1$, $X^2$, $X^3$, $X^4$, $Y^1$, $Y^2$, $Y^3$, $Y^4$, $M^1$, $M^2$, $M^3$, $A^m$ and $B^n$ are defined as in Formula (I); invention compounds are modulators of metabotropic glutamate receptors—subtype 4 ("mGluR4") which are useful for the treatment or prevention of central nervous system disorders as well as other disorders modulated by mGluR4 receptors. The invention is also directed to pharmaceutical compositions and the use of such compounds in the manufacture of medicaments, as well as to the use of such compounds for the prevention and treatment of such diseases in which mGluR4 is involved.

BACKGROUND OF THE INVENTION

Glutamate is the major amino-acid transmitter in the mammalian central nervous system (CNS). Glutamate plays a major role in numerous physiological functions, such as learning and memory but also sensory perception, development of synaptic plasticity, motor control, respiration and regulation of cardiovascular function. Furthermore, glutamate is at the center of several different neurological and psychiatric diseases, where there is an imbalance in glutamatergic neurotransmission.

Glutamate mediates synaptic neurotransmission through the activation of ionotropic glutamate receptor channels (iGluRs), namely the NMDA, AMPA and kainate receptors which are responsible for fast excitatory transmission (Nakanishi et al., (1998) Brain Res Rev., 26:230-235).

In addition, glutamate activates metabotropic glutamate receptors (mGluRs) which have a more modulatory role that contributes to the fine-tuning of synaptic efficacy.

The mGluRs are G protein-coupled receptors (GPCRs) with seven-transmembrane spanning domains and belong to GPCR family 3 along with the calcium-sensing, GABAb and pheromone receptors.

The mGluR family is composed of eight members. They are classified into three groups (group I comprising mGluR1 and mGluR5; group II comprising mGluR2 and mGluR3; group III comprising mGluR4, mGluR6, mGluR7 and mGluR8) according to sequence homology, pharmacological profile and nature of intracellular signalling cascades activated (Schoepp et al. (1999) Neuropharmacology, 38:1431-76).

Glutamate activates the mGluRs through binding to the large extracellular amino-terminal domain of the receptor, herein called the orthosteric binding site. This activation induces a conformational change of the receptor which results in the activation of the G-protein and intracellular signalling pathways.

In the central nervous system, mGluR4 receptors are expressed most intensely in the cerebellar cortex, basal ganglia, sensory relay nuclei of the thalamus and hippocampus (Bradley et al. (1999) Journal of Comparative Neurology, 407:33-46; Corti et al. (2002) Neuroscience, 110:403-420). The mGluR4 subtype is negatively coupled to adenylate cyclase via activation of the Gαi/o protein, is expressed primarily on presynaptic terminals, functioning as an autoreceptor or heteroceptor and activation of mGluR4 leads to decreases in transmitter release from presynaptic terminals (Corti et al. (2002) Neuroscience, 110:403-420; Millan et al. (2002) Journal of Biological Chemistry 277:47796-47803; Valenti et al. (2003) Journal of Neuroscience 23:72218-7226).

Orthosteric agonists of mGluR4 are not selective and activate the other Group III mGluRs (Schoepp et al (1999) Neuropharmacology 38:1431-1476). The Group III orthosteric agonist L-AP4 was able to reduce motor deficits in animal models of Parkinson's disease (Valenti et al (2003) J. Neurosci. 23:7218-7226) and decrease excitotoxicity (Bruno et al (2000) J. Neurosci. 20; 6413-6420) and these effects appear to be mediated through mGluR4 (Marino et al (2005) Curr. Topics Med. Chem. 5:885-895). In addition to LAP-4, ACPT-1, another selective group III mGluR agonist has been shown to caused a dose-and-structure dependant decrease in haloperidol-induced catalepsy and attenuated haloperidol-increased Proenkephalin mRNA expression in the striatum (Konieczny et al 2007). Furthermore, Lopez et al (2007, J Neuroscience) have shown that bilateral infusions of ACPT-I or LAP-4 into the globus pallidus fully reversed the severe akinetic deficits produced by 6-hydroxydopamine lesions of nigrostriatal dopamine neurons in a reaction-time task without affecting the performance of controls. In addition, the reversal of haloperidol-induced catalepsy by intrapallidal ACPT-1 was prevented by concomitant administration of a selective group III receptor antagonist (RS)-alpha-cyclopropyl-4-phosphonophenylglycine. The opposite effects produced by group III mGluR activation in the SNr strongly suggest a role of mGluR4 rather than others mGluR receptor sub-types in normalizing basal ganglia activity (Lopez et al 2007).

These results suggest that, among mGluRs subtypes, mGluR4 is believed to be the most interesting novel drug target for the treatment of Parkinson's disease (for a review see Conn et al Nature Review Neuroscience 2005).

Symptoms of Parkinson's disease appear to be due to an imbalance in the direct and indirect output pathways of the basal ganglia and reduction of transmission at the inhibitory GABAergic striato-pallidal synapse in the indirect pathway may result in alleviation of these symptoms (Marino et al. (2002) Amino Acids, 23:185-191).

mGluR4 is more abundant in striato-pallidal synapses than in striato-nigral synapses, and its localization suggests function as a presynaptic heteroceptor on GABAergic neurons (Bradley et al. (1999) Journal of Comparative Neurology, 407:33-46) suggesting that selective activation or positive modulation of mGluR4 would decrease GABA release in this synapse thereby decreasing output of the indirect pathway and reducing or eliminating the Parkinson's disease symptoms.

A new avenue for developing selective compounds acting at mGluRs is to identify molecules that act through allosteric mechanisms, modulating the receptor by binding to a site different from the highly conserved orthosteric binding site.

Positive allosteric modulators of mGluRs have emerged recently as novel pharmacological entities offering this attractive alternative. This type of molecule has been discovered for mGluR1, mGluR2, mGluR4, mGluR5, mGluR7 and mGluR8 (Knoflach F. et al. (2001) Proc. Natl. Acad. Sci. USA., 98:13402-13407; Johnson K et al. (2002) Neuropharmacology, 43:291; O'Brien J. A. et al. (2003) Mol. Pharmacol., 64:731-40; Johnson M. P. et al. (2003) J. Med. Chem., 46:3189-92; Marino M. J. et al. (2003) Proc. Natl. Acad. Sci. USA., 100:13668-73; Mitsukawa K. et al. (2005) Proc Natl Acad Sci USA 102(51):18712-7; Wilson J. et al. (2005) Neuropharmacology 49:278; for a review see Mutel V. (2002) Expert Opin. Ther. Patents, 12:1-8; Kew J. N. (2004) Pharmacol. Ther., 104(3):233-44; Johnson M. P. et al. (2004) Biochem. Soc. Trans., 32:881-7; recently Ritzen A., Mathiesen, J. M., and Thomsen C. (2005) Basic Clin. Pharmacol. Toxicol. 97:202-13).

In particular molecules have been described as mGluR4 positive allosteric modulators (Maj et al (2003) Neuropharmacology 45:895-906; Mathiesen et al. (2003) British Journal of Pharmacology 138:1026-1030). It has been demonstrated that such molecules have been characterized in in vitro systems as well as in rat brain slices where they potentiated the effect of LAP-4 in inhibiting transmission at the striatopallidal synapse. These compounds do not activate the receptor by themselves (Marino et al (2003) Proc. Nat. Acad. Sci. USA 100:13668-13673). Rather, they enable the receptor to produce a maximal response to a concentration of glutamate or the Group III orthosteric agonist L-AP4 which by itself induces a minimal response.

PHCCC, a positive allosteric modulator of mGluR4 not active on others mGluRs (Maj et al (2003) Neuropharmacology 45:895-906), has been shown to be efficacious in animal models of Parkinson's disease thus representing a potential novel therapeutic approach for Parkinson's disease as well as for other motor disorders and disturbances (Marino et al (2003) Proc. Nat. Acad. Sci. USA 100:13668-13673), neurodegeneration in Parkinson's disease (Marino et al (2005) Curr. Topics Med. Chem. 5:885-895; Valenti et al (2005) J Pharmacol. Exp. Ther. 313:1296-1304; Vernon et al (2005) Eur. J Neurosci. 22:1799-1806, Battaglia et al (2006) J. Neurosci. 26:7222-7229), and neurodegeneration in Alzheimer's disease or due to ischemic or traumatic insult (Maj et al (2003) Neuropharmacology 45:895-906).

PHCCC also has been shown to be active in animal model of anxiety (Stachowicz et al (2004) Eur J Pharmacol 498:153-156). Previously, ACPT-1 has been showed to produce a dose-dependent anti-conflict effect after intrahippocampal administration and anti-depressant-like effects in rats after intracerebroventricular administration (Tatarczynska et al., 2002)

Activation of mGluR4 receptors which are expressed in α- and F cells in the islets of Langerhans inhibits glucagon secretion. Molecules which activate or potentiate agonist activity of these receptors may be an effective treatment for hyperglycemia, one of the symptoms of type 2 diabetes (Uehara et al (2004) Diabetes 53:998-1006).

The β-chemokine RANTES is importantly involved in neuronal inflammation and has been implicated in the pathophysiology of multiple sclerosis. Activation of Group III mGluRs with L-AP4 reduced the synthesis and release RANTES in wild-type cultured astrocytes, whereas the ability of L-AP4 to inhibit RANTES was greatly decreased in astrocyte cultures from mGluR4 knockout mice (Besong et al. (2002) Journal of Neuroscience, 22:5403-5411). These data suggest that positive allosteric modulators of mGluR4 may be an effective treatment for neuroinflammatory disorders of the central nervous system, including multiple sclerosis and related disorders.

Two different variants of the mGluR4 receptor are expressed in taste tissues and may function as receptors for the umami taste sensation (Monastyrskaia et al (1999) Br. J Pharmacol. 128:1027-1034; Toyono et al (2002) Arch. Histol. Cytol. 65:91-96). Thus positive allosteric modulators of mGluR4 may be useful as taste agents, flavour agents, flavour enhancing agents or food additives.

There are anatomical evidence that the majority of vagal afferents innervating gastric muscle express group III mGluRs (mGluR4, mGluR6, mGluR7 and mGluR8) and actively transport receptors to their peripheral endings (Page et al (2005) 128:402-10). Recently, it was shown that the activation of peripheral group III mGluRs inhibited vagal afferents mechanosensitivity in vitro which translates into reduced triggering of transient lower oesophagal sphincter relaxations and gastroesophageal reflux in vivo (Young et al (2008) Neuropharmacol 54:965-975). Labelling for mGluR4 and mGluR8 was abundant in gastric vagal afferents in the nodose ganglion, at their termination sites in the nucleus tractus solitarius and in gastric vagal motoneurons. These data suggest that positive allosteric modulators of mGluR4 may be an effective treatment for gastro-esophageal reflux disease (GERD) and lower esophageal disorders and gastrointestinal disorders.

International patent publication WO2005/007096 describes mGluR4 receptor positive allosteric modulator useful, alone or in combination with a neuroleptic agent, for treating or preventing movement disorders. However, none of the specifically disclosed compounds are structurally related to the compounds of the invention.

(i) International patent publication WO2006/122011 describes 4-(2-(4-(octyloxy)-3-(trifluoromethyl)phenylamino)thiazol-4-yl)-1H-pyrazol-3-carbonitrile, having inhibitory activity on hepatitis C virus replication.

(ii) Mizutani et al (2004) J. Med. Chem. 47 (20): 4818-4828 describes 3-(1-(3,5-bis(trifluoromethyl)phenylsulfonyl)-3-methyl-1H-pyrazol-4-yl)-N-phenyl-1,2,4-thiadiazol-5-amine as an inhibitor toward AChE.

(iii) International patent publication WO2001/64674 describes N-phenyl-4-(1H-pyrazol-3-yl)thiazol-2-amine hydrobromide having proinflammatory cytokine production inhibiting properties and adenosine $A_3$ receptor blocking properties. Dhiman et al (2001) Ind. J. Chem., Section B, 40B (7): 636-639, Dorokhov et al (2004) Russian Chem. Bull., Int. Ed., 53 (3): 676-680 and Stachel (1962) Chem. Ber., 95: 2166-2171 described synthetic routes to obtain pyrazoles substituted in position 3 by an aminophenylheterocycle. More et al (2006) Ind. J. Het. Chem. 16 (2): 155-158 described synthetic routes to obtain indazoles substituted in position 3 by an aminophenylheterocycle.

It has now surprisingly been found that the compounds of general formula I show potent activity and selectivity on mGluR4 receptor. The compounds of the invention demonstrate advantageous properties over compounds of the prior art. Improvements have been observed in one or more of the following characteristics of the compounds of the invention:

the potency on the target, the selectivity for the target, the bioavailability, the brain penetration, and the activity in behavioural models.

The present invention relates to a method of treating or preventing a condition in a mammal, including a human, the treatment or prevention of which is affected or facilitated by the neuromodulatory effect of mGluR4 modulators.

DETAILED DESCRIPTION OF THE INVENTION

The invention relates to compounds having metabotropic glutamate receptor 4 modulator activity. In its most general compound aspect, the present invention provides a compound according to Formula (I),

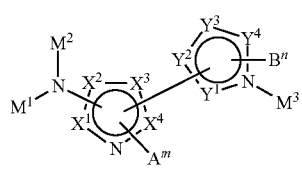

(I)

a pharmaceutically acceptable acid or base addition salt thereof, a stereochemically isomeric form thereof and an N-oxide form thereof, wherein:

$X^1$, $X^2$, $X^3$ and $X^4$ are each independently selected from the group of C, N, O, S and C=C representing a 5 or 6 membered heteroaryl ring which may further be substituted by 1 to 3 radicals $A^m$;

m is an integer ranging from 1 to 3;

$A^m$ radicals are each independently selected from the group of hydrogen, halogen, —CN, —OH, —NO$_2$, —CF$_3$, —SH, —NH$_2$ and an optionally substituted radical selected from the group of —(C$_1$-C$_6$)alkyl, —(C$_1$-C$_6$)alkylhalo, —(C$_2$-C$_6$)alkynyl, —(C$_2$-C$_6$)alkenyl, —(C$_3$-C$_7$)cycloalkyl, —(C$_3$-C$_8$)cycloalkenyl, —(C$_1$-C$_6$)alkylcyano, —(C$_1$-C$_6$)alkylheteroaryl, —(C$_1$-C$_6$)alkylaryl, aryl, heteroaryl, heterocycle, —(C$_0$-C$_6$)alkyl-OR$^1$, —O—(C$_2$-C$_6$)alkyl-OR$^1$, —NR$^1$(C$_2$-C$_6$)alkyl-OR$^2$, —(C$_3$-C$_2$)cycloalkyl-(C$_1$-C$_6$)alkyl, —O—(C$_3$-C$_2$)cycloalkyl-(C$_1$-C$_6$)alkyl, —NR$^1$—(C$_3$-C$_2$)cycloalkyl-(C$_1$-C$_6$)alkyl, —(C$_1$-C$_6$)alkylhalo-OR$^1$, —(C$_1$-C$_6$)alkylhalo-NR$^1$R$^2$, —(C$_3$-C$_6$)alkynyl-OR$^1$, —(C$_3$-C$_6$)alkynyl-NR$^1$R$^2$, —(C$_3$-C$_6$)alkenyl-OR$^1$, —(C$_3$-C$_6$)alkenyl-NR'R$^2$, —(C$_0$-C$_6$)alkyl-S—R$^1$, —O—(C$_2$-C$_6$)alkyl-S—R$^1$, —NR$^1$—(C$_2$-C$_6$)alkyl-S—R$^2$, —(C$_0$-C$_6$)alkyl-S(=O)—R$^1$, —O—(C$_1$-C$_6$)alkyl-S(=O)—R$^1$, —NR$^1$—(C$_1$-C$_6$)alkyl-S(=O)—R$^2$, —(C$_0$-C$_6$)alkyl-S(=O)$_2$—R$^1$, —O—(C$_1$-C$_6$)alkyl-S(=O)$_2$—R$^1$, —NR$^1$—(C$_1$-C$_6$)alkyl-S(=O)$_2$—R$^2$, —(C$_0$-C$_6$)alkyl-NR$^1$R$^2$, —O—(C$_2$-C$_6$)alkyl-NR$^1$R$^2$, —NR$^1$—(C$_2$-C$_6$)alkyl-NR$^2$R$^3$, —(C$_0$-C$_6$)alkyl-S(=O)$_2$NR$^1$R$^2$, —O—(C$_1$-C$_6$)alkyl-S(=O)$_2$NR$^1$R$^2$, —NR$^1$—(C$_1$-C$_6$)alkyl-S(=O)$_2$NR$^2$R$^3$, —(C$_0$-C$_6$)alkyl-NR$^1$—S(=O)$_2$R$^2$, —O—(C$_2$-C$_6$)alkyl-NR$^1$—S(=O)$_2$R$^2$, —NR$^1$—(C$_2$-C$_6$)alkyl-NR$^2$—S(=O)$_2$R$^3$, —(C$_0$-C$_6$)alkyl-C(=O)—NR$^1$R$^2$, —O—(C$_1$-C$_6$)alkyl-C(=O)—NR$^1$R$^2$, —NR$^1$—(C$_1$-C$_6$)alkyl-C(=O)—NR$^2$R$^3$, —(C$_0$-C$_6$)alkyl-NR$^1$C(=O)—R$^2$, —O—(C$_2$-C$_6$)alkyl-NR$^1$C(=O)—R$^2$, —NR$^1$—(C$_2$-C$_6$)alkyl-NR$^2$C(=O)—R$^3$, —(C$_0$-C$_6$)alkyl-OC(=O)—R$^1$, —O—(C$_2$-C$_6$)alkyl-OC(=O)—R$^1$, —NR$^1$—(C$_2$-C$_6$)alkyl-OC(=O)—R$^2$, —(C$_0$-C$_6$)alkyl-C(=O)—OR$^1$, —O—(C$_1$-C$_6$)alkyl-C(=O)—OR$^1$, —NR$^1$—(C$_1$-C$_6$)alkyl-C(=O)—OR$^2$, —(C$_0$-C$_6$)alkyl-C(=O)—R$^1$, —O—(C$_1$-C$_6$)alkyl-C(=O)—R$^1$, —NR$^1$—(C$_1$-C$_6$)alkyl-C(=O)—R$^2$, —(C$_0$-C$_6$)alkyl-NR$^1$—C(=O)—OR$^2$, —(C$_0$-C$_6$)alkyl-O—C(=O)—NR$^1$R$^2$, —(C$_0$-C$_6$)alkyl-NR$^1$—C(=NR$^2$)—NR$^3$R$^4$, —(C$_0$-C$_6$)alkyl-NR$^1$—C(=O)—NR$^2$R$^3$, —O—(C$_2$-C$_6$)alkyl-NR$^1$—C(=O)—NR$^2$R$^3$, —NR$^1$—(C$_2$-C$_6$)alkyl-NR$^2$—C(=O)—NR$^3$R$^4$ and —(C$_0$-C$_6$)alkyl-NR$^1$—C(=S)—NR$^2$R$^3$;

Any two radicals of $A^m$ ($A^1$ and $A^2$) may be taken together to form an optionally substituted 3 to 10 membered carbocyclic or heterocyclic ring;

$R^1$, $R^2$, $R^3$ and $R^4$ are each independently hydrogen or an optionally substituted radical selected from the group of —(C$_1$-C$_6$)alkylhalo, —(C$_1$-C$_6$)alkyl, —(C$_1$-C$_6$)alkylcyano, —(C$_3$-C$_7$)cycloalkyl, —(C$_4$-C$_{10}$)alkylcycloalkyl, heteroaryl, —(C$_1$-C$_6$)alkylheteroaryl, aryl, heterocycle and —(C$_1$-C$_6$)alkylaryl;

Any two radicals of R ($R^1$, $R^2$, $R^3$ or $R^4$) may be taken together to form an optionally substituted 3 to 10 membered carbocyclic or heterocyclic ring;

$Y^1$, $Y^2$, $Y^3$ and $Y^4$ are each independently selected from the group of C and N representing 5 membered heteroaryl ring which may further be substituted by 1 to 3 radicals $B''$;

n is an integer ranging from 1 to 3;

$B''$ radicals are each independently selected from the group of hydrogen, halogen, —CN, —OH, —NO$_2$, —CF$_3$, —SH, —NH$_2$ and an optionally substituted radical selected from the group of —(C$_1$-C$_6$)alkyl, —(C$_1$-C$_6$)alkylhalo, —(C$_2$-C$_6$)alkynyl, —(C$_2$-C$_6$)alkenyl, —(C$_3$-C$_7$)cycloalkyl, —(C$_3$-C$_8$)cycloalkenyl, —(C$_1$-C$_6$)alkylcyano, —(C$_1$-C$_6$)alkylheteroaryl, —(C$_1$-C$_6$)alkylaryl, aryl, heteroaryl, heterocycle, —(C$_0$-C$_6$)alkyl-OR$^5$, —O—(C$_2$-C$_6$)alkyl-OR$^5$, —NR$^5$(C$_2$-C$_6$)alkyl-OR$^6$, —(C$_3$-C$_2$)cycloalkyl-(C$_1$-C$_6$)alkyl, —O—(C$_3$-C$_2$)cycloalkyl-(C$_1$-C$_6$)alkyl, —NR$^5$—(C$_3$-C$_2$)cycloalkyl-(C$_1$-C$_6$)alkyl, —(C$_1$-C$_6$)alkylhalo-OR$^5$, —(C$_1$-C$_6$)alkylhalo-NR$^5$R$^6$, —(C$_3$-C$_6$)alkynyl-OR$^5$, —(C$_3$-C$_6$)alkynyl-NR$^5$R$^6$, —(C$_3$-C$_6$)alkenyl-OR$^5$, —(C$_3$-C$_6$)alkenyl-NR$^5$R$^6$, —(C$_0$-C$_6$)alkyl-S—R$^5$, —O—(C$_2$-C$_6$)alkyl-S—R$^5$, —NR$^5$—(C$_2$-C$_6$)alkyl-S—R$^6$, —(C$_0$-C$_6$)alkyl-S(=O)—R$^5$, —O—(C$_1$-C$_6$)alkyl-S(=O)—R$^5$, —NR$^5$—(C$_1$-C$_6$)alkyl-S(=O)—R$^6$, —(C$_0$-C$_6$)alkyl-S(=O)$_2$—R$^5$, —O—(C$_1$-C$_6$)alkyl-S(=O)$_2$—R$^5$, —NR$^5$—(C$_1$-C$_6$)alkyl-S(=O)$_2$—R$^6$, —(C$_0$-C$_6$)alkyl-NR$^5$R$^6$, —O—(C$_2$-C$_6$)alkyl-NR$^5$R$^6$, —NR$^5$—(C$_2$-C$_6$)alkyl-NR$^6$R$^2$, —(C$_0$-C$_6$)alkyl-S(=O)$_2$NR$^5$R$^6$, —O—(C$_1$-C$_6$)alkyl-S(=O)$_2$NR$^5$R$^6$, —NR$^5$—(C$_1$-C$_6$)alkyl-S(=O)$_2$NR$^6$R$^2$, —(C$_0$-C$_6$)alkyl-NR$^5$—S(=O)$_2$R$^6$, —O—(C$_2$-C$_6$)alkyl-NR$^5$—S(=O)$_2$R$^6$, —NR$^5$—(C$_2$-C$_6$)alkyl-NR$^6$—S(=O)$_2$R$^7$, —(C$_0$-C$_6$)alkyl-C(=O)—NR$^5$R$^6$, —O—(C$_1$-C$_6$)alkyl-C(=O)—NR$^5$R$^6$, —NR$^5$—(C$_1$-C$_6$)alkyl-C(=O)—NR$^6$R$^2$, —(C$_0$-C$_6$)alkyl-NR$^5$C(=O)—R$^6$, —O—(C$_2$-C$_6$)alkyl-NR$^5$C(=O)—R$^6$, —NR$^5$—(C$_2$-C$_6$)alkyl-NR$^6$C(=O)—R$^2$, —(C$_0$-C$_6$)alkyl-OC(=O)—R$^5$, —O—(C$_2$-C$_6$)alkyl-OC(=O)—R$^5$, —NR$^5$—(C$_2$-C$_6$)alkyl-OC(=O)—R$^6$, —(C$_0$-C$_6$)alkyl-C(=O)—OR$^5$, —O—(C$_1$-C$_6$)alkyl-C(=O)—OR$^5$, —NR$^5$—(C$_1$-C$_6$)alkyl-C(=O)—OR$^6$, —(C$_0$-C$_6$)alkyl-C(=O)—R$^5$, —O—(C$_1$-C$_6$)alkyl-C(=O)—R$^5$, —NR$^5$—(C$_1$-C$_6$)alkyl-C(=O)—R$^6$, —(C$_0$-C$_6$)alkyl-NR$^5$—C(=O)—OR$^6$, —(C$_0$-C$_6$)alkyl-O—C(=O)—NR$^5$R$^6$, —(C$_0$-C$_6$)alkyl-NR$^5$—C(=NR$^6$)—NR$^7$R$^8$, —(C$_0$-C$_6$)alkyl-NR$^5$—C(=O)—NR$^6$R$^2$, —O—(C$_2$-C$_6$)alkyl-NR$^5$—C(=O)—NR$^6$R$^2$, —NR$^5$—(C$_2$-C$_6$)alkyl-NR$^6$—C(=O)—NR$^2$R$^8$ and —(C$_0$-C$_6$)alkyl-NR$^5$—C(=S)—NR$^6$R$^2$;

Any two radicals of $B''$ ($B^1$ and $B^2$) may be taken together to form an optionally substituted 3 to 10 membered carbocyclic or heterocyclic ring;

$R^5$, $R^6$, $R^2$ and $R^8$ are each independently hydrogen or an optionally substituted radical selected from the group of —(C$_1$-C$_6$)alkylhalo, —(C$_1$-C$_6$)alkyl, —(C$_1$-C$_6$)alkylcyano, —($C_3$-$C_7$)cycloalkyl, —($C_4$-$C_{10}$)alkylcycloalkyl, heteroaryl, —($C_1$-$C_6$)alkylheteroaryl, aryl, heterocycle and —($C_1$-$C_6$)alkylaryl;

Any two radicals of R ($R^5$, $R^6$, $R^2$ or $R^8$) may be taken together to form an optionally substituted 3 to 10 membered carbocyclic or heterocyclic ring;

$M^1$ is selected from an optionally substituted 3 to 10 membered ring selected from the group of aryl, heteroaryl, heterocyclic and cycloalkyl;

$M^2$ is selected from the group of a hydrogen or an optionally substituted radical selected from the group of —($C_0$-$C_6$)alkyl-$R^9$, —($C_1$-$C_6$)alkylhalo, —($C_2$-$C_6$)alkyl-$NR^9R^{10}$, —($C_2$-$C_6$)alkyl-$OR^9$, —($C_2$-$C_6$)alkyl-$SR^9$, —($C_0$-$C_6$)alkyl-C(=O)—$R^9$, —($C_2$-$C_6$)alkyl-S(O)—$R^9$, —($C_0$-$C_6$)alkyl-C(=O)$NR^9R^{10}$ and —($C_0$-$C_6$)alkyl-S(O)$_2$—$R^9$;

$M^3$ is selected from the group of a hydrogen or an optionally substituted radical selected from the group of —($C_0$-$C_6$)alkyl-C(=O)—$R^{11}$, —($C_2$-$C_6$)alkyl-S(O)—$R^{11}$, —($C_0$-$C_6$)alkyl-C(=O)$NR^{11}R^{12}$ and —($C_0$-$C_6$)alkyl-S(O)$_2$—$R^{11}$;

$R^9$, $R^{10}$, $R^{11}$ and $R^{12}$ are selected from the group of a hydrogen or an optionally substituted radical selected from the group of —($C_1$-$C_6$)alkylhalo, —($C_1$-$C_6$)alkyl, —($C_1$-$C_6$)alkylcyano, —($C_3$-$C_7$)cycloalkyl, —($C_4$-$C_{10}$)alkylcycloalkyl, heteroaryl, —($C_1$-$C_6$)alkylheteroaryl, aryl, heterocycle and —($C_1$-$C_6$)alkylaryl;

provided that:
(i) when $M^2$ and $M^3$ are H, $X^1$, $X^3$ and $X^4$ are C, $X^2$ is S, $Y^1$, $Y^2$ and $Y^3$ are C, $Y^4$ is NH, m and n are both 1, $A^1$ is H and $B^1$ is —CN substituted on $Y^1$ then $M^1$ can not be an aryl optionally substituted by —O—($C_1$-$C_8$)alkyl;

and provided that:
(ii) when $M^1$ is aryl, $M^2$ is H, $X^1$ and $X^4$ are C, $X^2$ is S, $X^3$ is N, $Y^1$, $Y^2$ and $Y^3$ are C, $Y^4$ is NH, n is 1 and $B^1$ is alkyl substituted on $Y^1$ then $M^3$ can not be an optionally substituted —S(O)$_2$aryl;

and provided that:
(iii) Formula (I)

can not be

The compound 4-(2-(4-(octyloxy)-3-(trifluoromethyl)phenylamino)thiazol-4-yl)-1H-pyrazol-3-carbonitrile known as such from international patent publication WO2006/122011 is excluded from the present invention by virtue of proviso (i).

The compound 3-(1-(3,5-bis(trifluoromethyl)phenylsulfonyl)-3-methyl-1H-pyrazol-4-yl)-N-phenyl-1,2,4-thiadiazol-5-amine known as such from Mizutani et al (2004) J. Med. Chem. 47 (20): 4818-4828 is excluded from the present invention by virtue of proviso (ii).

The pyrazoles and indazoles substituted in position 3 by an aminophenylheterocycle known as such from international patent publication WO2001/64674, Dhiman et al (2001) Ind. J. Chem., Section B, 40B (7): 636-639, Dorokhov et al (2004) Russian Chem. Bull., Int. Ed., 53 (3): 676-680, Stachel (1962) Chem. Ber., 95: 2166-2171, and More et al (2006) Ind. J. Het. Chem. 16 (2): 155-158 are excluded from the present invention by virtue of proviso (iii).

In a more preferred aspect of Formula (I), the invention provides a compound according to Formula (II), (II)

a pharmaceutically acceptable acid or base addition salt thereof, a stereochemically isomeric form thereof and an N-oxide form thereof, wherein:

$X^1$, $X^2$ and $X^3$ are each independently selected from the group of C, N, O, S and C=C representing a 5 or 6 membered heteroaryl ring which may further be substituted by 1 to 3 radicals $A^m$;

m is an integer ranging from 1 to 3;

$A^m$ radicals are each independently selected from the group of hydrogen, halogen, —CN, —OH, —$NO_2$, —$CF_3$, —SH, —$NH_2$ and an optionally substituted radical selected from the group of —($C_1$-$C_6$)alkyl, —($C_1$-$C_6$)alkylhalo, —($C_2$-$C_6$)alkynyl, —($C_2$-$C_6$)alkenyl, —($C_3$-$C_7$)cycloalkyl, —($C_3$-$C_8$)cycloalkenyl, —($C_1$-$C_6$)alkylcyano, —($C_1$-$C_6$)alkylheteroaryl, —($C_1$-$C_6$)alkylaryl, aryl, heteroaryl, heterocycle, —($C_0$-$C_6$)alkyl-$OR^1$, —O—($C_2$-$C_6$)alkyl-$OR^1$, —$NR^1$($C_2$-$C_6$)alkyl-$OR^2$, —($C_3$-$C_2$)cycloalkyl-($C_1$-$C_6$)alkyl, —O—($C_3$-$C_2$)cycloalkyl-($C_1$-$C_6$)alkyl, —$NR^1$—($C_3$-$C_7$)cycloalkyl-($C_1$-$C_6$)alkyl, —($C_1$-$C_6$)alkylhalo-$OR^1$, —($C_1$-$C_6$)alkylhalo-$NR^1R^2$, —($C_3$-$C_6$)alkynyl-$OR^1$, —($C_3$-$C_6$)alkynyl-$NR^1R^2$, —($C_3$-$C_6$)alkenyl-$OR^1$, —($C_3$-$C_6$)alkenyl-$NR^1R^2$, —($C_0$-$C_6$)alkyl-S—$R^1$, —O—($C_2$-$C_6$)alkyl-S—$R^1$, —$NR^1$—($C_2$-$C_6$)alkyl-S—$R^2$, —($C_0$-$C_6$)alkyl-S(=O)—$R^1$, —O—($C_1$-$C_6$)alkyl-S(=O)—$R^1$, —$NR^1$—($C_1$-$C_6$)alkyl-S(=O)—$R^2$, —($C_0$-$C_6$)alkyl-S(=O)$_2$—$R^1$, —O—($C_1$-$C_6$)alkyl-S(=O)$_2$—$R^1$, —$NR^1$—($C_1$-$C_6$)alkyl-S(=O)$_2$—$R^2$, —($C_0$-$C_6$)alkyl-$NR^1R^2$, —O—($C_2$-$C_6$)alkyl-$NR^1R^2$, —$NR^1$—($C_2$-$C_6$)alkyl-$NR^2R^3$, —($C_0$-$C_6$)alkyl-S(=O)$_2$$NR^1R^2$, —O—($C_1$-$C_6$)alkyl-S(=O)$_2$$NR^1R^2$, —$NR^1$—($C_1$-$C_6$)alkyl-S(=O)$_2$$NR^2R^3$, —($C_0$-$C_6$)alkyl-$NR^1$—S(=O)$_2R^2$, —O—($C_2$-$C_6$)alkyl-$NR^1$—S(=O)$_2R^2$, —$NR^1$—($C_2$-$C_6$)alkyl-$NR^2$—S(=O)$_2R^3$, —($C_0$-$C_6$)alkyl-C(=O)—$NR^1R^2$, —O—($C_1$-$C_6$)alkyl-C(=O)—$NR^1R^2$, —$NR^1$—($C_1$-$C_6$)alkyl-C(=O)—$NR^2R^3$, —($C_0$-$C_6$)alkyl-$NR^1$C(=O)—$R^2$, —O—($C_2$-$C_6$)alkyl-$NR^1$C(=O)—$R^2$, —$NR^1$—($C_2$-$C_6$)alkyl-$NR^2$C(=O)—$R^3$, —($C_0$-$C_6$)alkyl-OC(=O)—$R^1$, —O—($C_2$-$C_6$)alkyl-OC(=O)—$R^1$, —$NR^1$—($C_2$-$C_6$)alkyl-OC(=O)—$R^2$, —($C_0$-$C_6$)alkyl-C(=O)—$OR^1$, —O—($C_1$-$C_6$)alkyl-C(=O)—$OR^1$, —$NR^1$—($C_1$-$C_6$)alkyl-C(=O)—$OR^2$, —($C_0$-$C_6$)alkyl-C(=O)—$R^1$, —O—($C_1$-$C_6$)alkyl-C(=O)—$R^1$, —$NR^1$—($C_1$-$C_6$)alkyl-C(=O)—$R^2$, —($C_0$-$C_6$)alkyl-$NR^1$—C(=O)—$OR^2$, —($C_0$-$C_6$)alkyl-O—C(=O)—$NR^1R^2$, —($C_0$-$C_6$)alkyl-$NR^1$—C(=$NR^2$)—$NR^3R^4$, —($C_0$-$C_6$)alkyl-$NR^1$—C(=O)—$NR^2R^3$, —O—($C_2$-$C_6$)alkyl-$NR^1$—C(=O)—$NR^2R^3$, —NR$^1$—(C$_2$-C$_6$)alkyl-NR$^2$—C(═O)—NR$^3$R$^4$ and —(C$_0$-C$_6$)alkyl-NR$^1$—C(═S)—NR$^2$R$^3$;

Any two radicals of A'" (A$^1$ and A$^2$) may be taken together to form an optionally substituted 3 to 10 membered carbocyclic or heterocyclic ring;

R$^1$, R$^2$, R$^3$ and R$^4$ are each independently hydrogen or an optionally substituted radical selected from the group of —(C$_1$-C$_6$)alkylhalo, —(C$_1$-C$_6$)alkyl, —(C$_1$-C$_6$)alkylcyano, —(C$_3$-C$_7$)cycloalkyl, —(C$_4$-C$_{10}$)alkylcycloalkyl, heteroaryl, —(C$_1$-C$_6$)alkylheteroaryl, aryl, heterocycle and —(C$_1$-C$_6$)alkylaryl;

Any two radicals of R (R$^1$, R$^2$, R$^3$ or R$^4$) may be taken together to form an optionally substituted 3 to 10 membered carbocyclic or heterocyclic ring;

n is an integer ranging from 1 to 2;

B" radicals are each independently selected from the group of hydrogen, halogen, —CN, —OH, —NO$_2$, —CF$_3$, —SH, —NH$_2$ and an optionally substituted radical selected from the group of —(C$_1$-C$_6$)alkyl, —(C$_1$-C$_6$)alkylhalo, —(C$_2$-C$_6$)alkynyl, —(C$_2$-C$_6$)alkenyl, —(C$_3$-C$_7$)cycloalkyl, —(C$_3$-C$_8$)cycloalkenyl, —(C$_1$-C$_6$)alkylcyano, —(C$_1$-C$_6$)alkylheteroaryl, —(C$_1$-C$_6$)alkylaryl, aryl, heteroaryl, heterocycle, —(C$_0$-C$_6$)alkyl-OR$^5$, —O—(C$_2$-C$_6$)alkyl-OR$^5$, —NR$^5$(C$_2$-C$_6$)alkyl-OR$^6$, —(C$_3$-C$_7$)cycloalkyl-(C$_1$-C$_6$)alkyl, —O—(C$_3$-C$_7$)cycloalkyl-(C$_1$-C$_6$)alkyl, —NR$^5$—(C$_3$-C$_7$)cycloalkyl-(C$_1$-C$_6$)alkyl, —(C$_1$-C$_6$)alkylhalo-OR$^5$, —(C$_1$-C$_6$)alkylhalo-NR$^5$R$^6$, —(C$_3$-C$_6$)alkynyl-OR$^5$, —(C$_3$-C$_6$)alkynyl-NR$^5$R$^6$, —(C$_3$-C$_6$)alkenyl-OR$^5$, —(C$_3$-C$_6$)alkenyl-NR$^5$R$^6$, —(C$_0$-C$_6$)alkyl-S—R$^5$, —O—(C$_2$-C$_6$)alkyl-S—R$^5$, —NR$^5$—(C$_2$-C$_6$)alkyl-S—R$^6$, —(C$_0$-C$_6$)alkyl-S(═O)—R$^5$, —O—(C$_1$-C$_6$)alkyl-S(═O)—R$^5$, —NR$^5$—(C$_1$-C$_6$)alkyl-S(═O)—R$^6$, —(C$_0$-C$_6$)alkyl-S(═O)$_2$—R$^5$, —O—(C$_1$-C$_6$)alkyl-S(═O)$_2$—R$^5$, —NR$^5$—(C$_1$-C$_6$)alkyl-S(═O)$_2$—R$^6$, —(C$_0$-C$_6$)alkyl-NR$^5$R$^6$, —O—(C$_2$-C$_6$)alkyl-NR$^5$R$^6$, —NR$^5$—(C$_2$-C$_6$)alkyl-NR$^6$R$^7$, —(C$_0$-C$_6$)alkyl-S(═O)$_2$NR$^5$R$^6$, —O—(C$_1$-C$_6$)alkyl-S(═O)$_2$NR$^5$R$^6$, —NR$^5$—(C$_1$-C$_6$)alkyl-S(═O)$_2$NR$^6$R$^7$, —(C$_0$-C$_6$)alkyl-NR$^5$—S(═O)$_2$R$^6$, —O—(C$_2$-C$_6$)alkyl-NR$^5$—S(═O)$_2$R$^6$, —NR$^5$—(C$_2$-C$_6$)alkyl-NR$^6$—S(═O)$_2$R$^7$, —(C$_0$-C$_6$)alkyl-C(═O)—NR$^5$R$^6$, —O—(C$_1$-C$_6$)alkyl-C(═O)—NR$^5$R$^6$, —NR$^5$—(C$_1$-C$_6$)alkyl-C(═O)—NR$^6$R$^7$, —(C$_0$-C$_6$)alkyl-NR$^5$C(═O)—R$^6$, —O—(C$_2$-C$_6$)alkyl-NR$^5$C(═O)—R$^6$, —NR$^5$—(C$_2$-C$_6$)alkyl-NR$^6$C(═O)—R$^7$, —(C$_0$-C$_6$)alkyl-OC(═O)—R$^5$, —O—(C$_2$-C$_6$)alkyl-OC(═O)—R$^5$, —NR$^5$—(C$_2$-C$_6$)alkyl-OC(═O)—R$^6$, —(C$_0$-C$_6$)alkyl-C(═O)—OR$^5$, —O—(C$_1$-C$_6$)alkyl-C(═O)—OR$^5$, —NR$^5$—(C$_1$-C$_6$)alkyl-C(═O)—OR$^6$, —(C$_0$-C$_6$)alkyl-C(═O)—R$^5$, —O—(C$_1$-C$_6$)alkyl-C(═O)—R$^5$, —NR$^5$—(C$_1$-C$_6$)alkyl-C(═O)—R$^6$, —(C$_0$-C$_6$)alkyl-NR$^5$—C(═O)—OR$^6$, —(C$_0$-C$_6$)alkyl-O—C(═O)—NR$^5$R$^6$, —(C$_0$-C$_6$)alkyl-NR$^5$—C(═NR$^6$)—NR$^7$R$^8$, —(C$_0$-C$_6$)alkyl-NR$^5$—C(═O)—NR$^6$R$^7$, —O—(C$_2$-C$_6$)alkyl-NR$^5$—C(═O)—NR$^6$R$^7$, —NR$^5$—(C$_2$-C$_6$)alkyl-NR$^6$—C(═O)—NR$^7$R$^8$ and —(C$_0$-C$_6$)alkyl-NR$^5$—C(═S)—NR$^6$R$^7$;

Any two radicals of B" (B$^1$ and B$^2$) may be taken together to form an optionally substituted 3 to 10 membered carbocyclic or heterocyclic ring;

R$^5$, R$^6$, R$^7$ and R$^8$ are each independently hydrogen or an optionally substituted radical selected from the group of —(C$_1$-C$_6$)alkylhalo, —(C$_1$-C$_6$)alkyl, —(C$_1$-C$_6$)alkylcyano, —(C$_3$-C$_7$)cycloalkyl, —(C$_4$-C$_{10}$)alkylcycloalkyl, heteroaryl, —(C$_1$-C$_6$)alkylheteroaryl, aryl, heterocycle and —(C$_1$-C$_6$)alkylaryl;

Any two radicals of R (R$^5$, R$^6$, R$^7$ or R$^8$) may be taken together to form an optionally substituted 3 to 10 membered carbocyclic or heterocyclic ring;

M$^1$ is selected from an optionally substituted 3 to 10 membered ring selected from the group of aryl, heteroaryl, heterocyclic and cycloalkyl;

M$^2$ is selected from the group of a hydrogen or an optionally substituted radical selected from the group of —(C$_0$-C$_6$)alkyl-R$^9$, —(C$_1$-C$_6$)alkylhalo, —(C$_2$-C$_6$)alkyl-NR$^9$R$^{10}$, —(C$_2$-C$_6$)alkyl-OR$^9$, —(C$_2$-C$_6$)alkyl-SR$^9$, —(C$_0$-C$_6$)alkyl-C(═O)—R$^9$, —(C$_2$-C$_6$)alkyl-S(O)—R$^9$, —(C$_0$-C$_6$)alkyl-C(═O)NR$^9$R$^{10}$ and —(C$_0$-C$_6$)alkyl-S(O)$_2$—R$^9$;

M$^3$ is selected from the group of a hydrogen or an optionally substituted radical selected from the group of —(C$_0$-C$_6$)alkyl-C(═O)—R$^{11}$, —(C$_2$-C$_6$)alkyl-S(O)—R$^{11}$, —(C$_0$-C$_6$)alkyl-C(═O)NR$^{11}$R$^{12}$ and —(C$_0$-C$_6$)alkyl-S(O)$_2$—R$^{11}$;

R$^9$, R$^{10}$, R$^{11}$ and R$^{12}$ are selected from the group of a hydrogen or an optionally substituted radical selected from the group of —(C$_1$-C$_6$)alkylhalo, —(C$_1$-C$_6$)alkyl, —(C$_1$-C$_6$)alkylcyano, —(C$_3$-C$_7$)cycloalkyl, —(C$_4$-C$_{10}$)alkylcycloalkyl, heteroaryl, —(C$_1$-C$_6$)alkylheteroaryl, aryl, heterocycle and —(C$_1$-C$_6$)alkylaryl;

provided that:

(i) when M$^2$ and M$^3$ are H, X$^1$ is S, X$^2$ and X$^3$ are C, m and n are both 1, A$^1$ is H and B$^1$ is —CN then M$^1$ can not be an aryl optionally substituted by —O—(C$_1$-C$_8$)alkyl;

and provided that:

(ii) when M$^1$ is aryl, M$^2$ is H, X$^1$ is S, X$^2$ is N, X$^3$ is C, n is 1 and B$^1$ is alkyl then M$^3$ can not be an optionally substituted —S(O)$_2$aryl;

and provided that:

(iii) Formula (I)

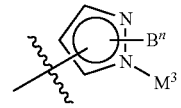

can not be

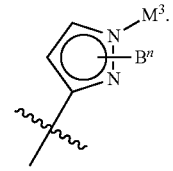

In a more preferred aspect of Formula (II), the invention provides a compound according to Formula (III),

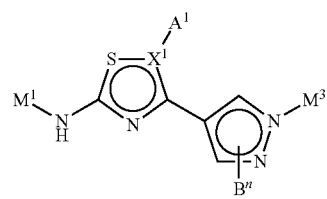

(III)

a pharmaceutically acceptable acid or base addition salt thereof, a stereochemically isomeric form thereof and an N-oxide form thereof, wherein:

X$^1$ is selected from C or N which may further be substituted by A$^1$;

$A^1$ radical is selected from the group of hydrogen, halogen, —CN, —OH, —$CF_3$, —SH, —$NH_2$ and an optionally substituted radical selected from the group of —$(C_1$-$C_6)$alkyl, —$(C_1$-$C_6)$alkylhalo, —$(C_2$-$C_6)$alkynyl, —$(C_2$-$C_6)$alkenyl, —$(C_3$-$C_7)$cycloalkyl, —$(C_3$-$C_8)$cycloalkenyl, —$(C_1$-$C_6)$alkylcyano, —$(C_1$-$C_6)$alkylheteroaryl, —$(C_1$-$C_6)$alkylaryl, aryl, heteroaryl, heterocycle, —$(C_0$-$C_6)$alkyl-$OR^1$, —O—$(C_2$-$C_6)$alkyl-$OR^1$, —$NR^1(C_2$-$C_6)$alkyl-$OR^2$, —$(C_3$-$C_7)$cycloalkyl-$(C_1$-$C_6)$alkyl, —O—$(C_3$-$C_7)$cycloalkyl-$(C_1$-$C_6)$alkyl, —$NR^1$—$(C_3$-$C_7)$cycloalkyl-$(C_1$-$C_6)$alkyl, —$(C_1$-$C_6)$alkylhalo-$OR^1$, —$(C_1$-$C_6)$alkylhalo-$NR^1R^2$, —$(C_3$-$C_6)$alkynyl-$OR^1$, —$(C_3$-$C_6)$alkynyl-$NR^1R^2$, —$(C_3$-$C_6)$alkenyl-$OR^1$, —$(C_3$-$C_6)$alkenyl-$NR^1R^2$, —$(C_0$-$C_6)$alkyl-S—$R^1$, —O—$(C_2$-$C_6)$alkyl-S—$R^1$, —$NR^1$—$(C_2$-$C_6)$alkyl-S—$R^2$, —$(C_0$-$C_6)$alkyl-S(=O)—$R^1$, —O—$(C_1$-$C_6)$alkyl-S(=O)—$R^1$, —$NR^1$—$(C_1$-$C_6)$alkyl-S(=O)—$R^2$, —$(C_0$-$C_6)$alkyl-S(=O)$_2$—$R^1$, —O—$(C_1$-$C_6)$alkyl-S(=O)$_2$—$R^1$, —$NR^1$—$(C_1$-$C_6)$alkyl-S(=O)$_2$—$R^2$, —$(C_0$-$C_6)$alkyl-$NR^1R^2$, —O—$(C_2$-$C_6)$alkyl-$NR^1R^2$, —$NR^1$—$(C_2$-$C_6)$alkyl-$NR^2R^3$, —$(C_0$-$C_6)$alkyl-S(=O)$_2NR^1R^2$, —O—$(C_1$-$C_6)$alkyl-S(=O)$_2NR^1R^2$, —$NR^1$—$(C_1$-$C_6)$alkyl-S(=O)$_2NR^2R^3$, —$(C_0$-$C_6)$alkyl-$NR^1$—S(=O)$_2R^2$, —O—$(C_2$-$C_6)$alkyl-$NR^1$—S(=O)$_2R^2$, —$NR^1$—$(C_2$-$C_6)$alkyl-$NR^2$—S(=O)$_2R^3$, —$(C_0$-$C_6)$alkyl-C(=O)—$NR^1R^2$, —O—$(C_1$-$C_6)$alkyl-C(=O)—$NR^1R^2$, —$NR^1$—$(C_1$-$C_6)$alkyl-C(=O)—$NR^2R^3$, —$(C_0$-$C_6)$alkyl-$NR^1C$(=O)—$R^2$, —O—$(C_2$-$C_6)$alkyl-$NR^1C$(=O)—$R^2$, —$NR^1$—$(C_2$-$C_6)$alkyl-$NR^2C$(=O)—$R^3$, —$(C_0$-$C_6)$alkyl-C(=O)—$R^1$, —O—$(C_1$-$C_6)$alkyl-C(=O)—$R^1$, —$NR^1$—$(C_1$-$C_6)$alkyl-C(=O)—$R^2$, —$(C_0$-$C_6)$alkyl-$NR^1$—C(=O)—$NR^2R^3$, —O—$(C_2$-$C_6)$alkyl-$NR^1$—C(=O)—$NR^2R^3$, —$NR^1$—$(C_2$-$C_6)$alkyl-$NR^2$—C(=O)—$NR^3R^4$ and —$(C_0$-$C_6)$alkyl-$NR^1$—C(=S)—$NR^2R^3$;

$R^1$, $R^2$, $R^3$ and $R^4$ are each independently hydrogen or an optionally substituted radical selected from the group of —$(C_1$-$C_6)$alkylhalo, —$(C_1$-$C_6)$alkyl, —$(C_1$-$C_6)$alkylcyano, —$(C_3$-$C_7)$cycloalkyl, —$(C_4$-$C_{10})$alkylcycloalkyl, heteroaryl, —$(C_1$-$C_6)$alkylheteroaryl, aryl, heterocycle and —$(C_1$-$C_6)$alkylaryl;

Any two radicals of R ($R^1$, $R^2$, $R^3$ or $R^4$) may be taken together to form an optionally substituted 3 to 10 membered carbocyclic or heterocyclic ring;

n is an integer ranging from 1 to 2;

$B''$ radicals are each independently selected from the group of hydrogen, halogen, —CN, —OH, —$CF_3$, —SH, —$NH_2$ and an optionally substituted radical selected from the group of —$(C_1$-$C_6)$alkyl, —$(C_1$-$C_6)$alkylhalo, —$(C_2$-$C_6)$alkynyl, —$(C_2$-$C_6)$alkenyl, —$(C_3$-$C_7)$cycloalkyl, —$(C_3$-$C_8)$cycloalkenyl, —$(C_1$-$C_6)$alkylcyano, —$(C_1$-$C_6)$alkylheteroaryl, —$(C_1$-$C_6)$alkylaryl, aryl, heteroaryl, heterocycle, —$(C_0$-$C_6)$alkyl-$OR^5$, —O—$(C_2$-$C_6)$alkyl-$OR^5$, —$NR^5(C_2$-$C_6)$alkyl-$OR^6$, —$(C_3$-$C_7)$cycloalkyl-$(C_1$-$C_6)$alkyl, —O—$(C_3$-$C_2)$cycloalkyl-$(C_1$-$C_6)$alkyl, —$NR^5$—$(C_3$-$C_2)$cycloalkyl-$(C_1$-$C_6)$alkyl, —$(C_1$-$C_6)$alkylhalo-$OR^5$, —$(C_1$-$C_6)$alkylhalo-$NR^5R^6$, —$(C_3$-$C_6)$alkynyl-$OR^5$, —$(C_3$-$C_6)$alkynyl-$NR^5R^6$, —$(C_3$-$C_6)$alkenyl-$OR^5$, —$(C_3$-$C_6)$alkenyl-$NR^5R^6$, —$(C_0$-$C_6)$alkyl-S—$R^5$, —O—$(C_2$-$C_6)$alkyl-S—$R^5$, —$NR^5$—$(C_2$-$C_6)$alkyl-S—$R^6$, —$(C_0$-$C_6)$alkyl-S(=O)—$R^5$, —O—$(C_1$-$C_6)$alkyl-S(=O)—$R^5$, —$NR^5$—$(C_1$-$C_6)$alkyl-S(=O)—$R^6$, —$(C_0$-$C_6)$alkyl-S(=O)$_2$—$R^5$, —O—$(C_1$-$C_6)$alkyl-S(=O)$_2$—$R^5$, —$NR^5$—$(C_1$-$C_6)$alkyl-S(=O)$_2$—$R^6$, —$(C_0$-$C_6)$alkyl-$NR^5R^6$, —O—$(C_2$-$C_6)$alkyl-$NR^5R^6$, —$NR^5$—$(C_2$-$C_6)$alkyl-$NR^6R^7$, —$(C_0$-$C_6)$alkyl-S(=O)$_2NR^5R^6$, —O—$(C_1$-$C_6)$alkyl-S(=O)$_2NR^5R^6$, —$NR^5$—$(C_1$-$C_6)$alkyl-S(=O)$_2NR^6R^7$, —$(C_0$-$C_6)$alkyl-$NR^5$—S(=O)$_2R^6$, —O—$(C_2$-$C_6)$alkyl-$NR^5$—S(=O)$_2R^6$, —$NR^5$—$(C_2$-$C_6)$alkyl-$NR^6$—S(=O)$_2R^7$, —$(C_0$-$C_6)$alkyl-C(=O)—$NR^5R^6$, —O—$(C_1$-$C_6)$alkyl-C(=O)—$NR^5R^6$, —$NR^5$—$(C_1$-$C_6)$alkyl-C(=O)—$NR^6R^7$, —$(C_0$-$C_6)$alkyl-$NR^5C$(=O)—$R^6$, —O—$(C_2$-$C_6)$alkyl-$NR^5C$(=O)—$R^6$, —$NR^5$—$(C_2$-$C_6)$alkyl-$NR^6C$(=O)—$R^7$, —$(C_0$-$C_6)$alkyl-C(=O)—$R^5$, —O—$(C_1$-$C_6)$alkyl-C(=O)—$R^5$, —$NR^5$—$(C_1$-$C_6)$alkyl-C(=O)—$R^6$, —$(C_0$-$C_6)$alkyl-$NR^5$—C(=O)—$NR^6R^7$, —O—$(C_2$-$C_6)$alkyl-$NR^5$—C(=O)—$NR^6R^7$, —$NR^5$—$(C_2$-$C_6)$alkyl-$NR^6$—C(=O)—$NR^7R^8$ and —$(C_0$-$C_6)$alkyl-$NR^5$—C(=S)—$NR^6R^7$;

$R^5$, $R^6$, $R^7$ and $R^8$ are each independently hydrogen or an optionally substituted radical selected from the group of —$(C_1$-$C_6)$alkylhalo, —$(C_1$-$C_6)$alkyl, —$(C_1$-$C_6)$alkylcyano, —$(C_3$-$C_7)$cycloalkyl, —$(C_4$-$C_{10})$alkylcycloalkyl, heteroaryl, —$(C_1$-$C_6)$alkylheteroaryl, aryl, heterocycle and —$(C_1$-$C_6)$alkylaryl;

Any two radicals of R ($R^5$, $R^6$, $R^7$ or $R^8$) may be taken together to form an optionally substituted 3 to 10 membered carbocyclic or heterocyclic ring;

$M^1$ is selected from an optionally substituted 3 to 10 membered ring selected from the group of aryl, heteroaryl, heterocyclic and cycloalkyl;

$M^3$ is selected from the group of a hydrogen or an optionally substituted radical selected from the group of —$(C_0$-$C_6)$alkyl-C(=O)—$R^9$, —$(C_2$-$C_6)$alkyl-S(O)—$R^9$, —$(C_0$-$C_6)$alkyl-C(=O)$NR^9R^{10}$ and —$(C_0$-$C_6)$alkyl-S(O)$_2$—$R^9$;

$R^9$ and $R^{16}$ are selected from the group of a hydrogen or an optionally substituted radical selected from the group of —$(C_1$-$C_6)$alkylhalo, —$(C_1$-$C_6)$alkyl, —$(C_1$-$C_6)$alkylcyano, —$(C_3$-$C_7)$cyclo alkyl, —$(C_4$-$C_{10})$alkylcycloalkyl, heteroaryl, —$(C_1$-$C_6)$alkylheteroaryl, aryl, heterocycle and —$(C_1$-$C_6)$alkylaryl;

provided that:

(i) when $M^3$ is H, $X^1$ is C, m and n are both 1, $A^1$ is H and $B^1$ is —CN then $M^1$ can not be an aryl optionally substituted by —O—$(C_1$-$C_8)$alkyl;

and provided that:

(ii) when $M^1$ is aryl, $X^1$ is N, n is 1 and $B^1$ is alkyl then $M^3$ can not be an optionally substituted —S(O)$_2$aryl.

In a more preferred aspect of Formula (III), the invention provides a compound according to Formula (III-A),

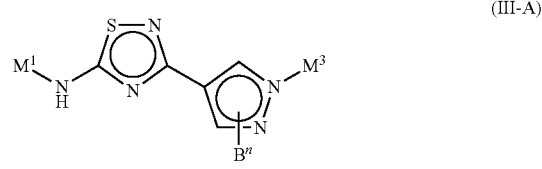

(III-A)

a pharmaceutically acceptable acid or base addition salt thereof, a stereochemically isomeric form thereof and an N-oxide form thereof, wherein:

n is an integer ranging from 1 to 2;

$B''$ radicals are each independently selected from the group of hydrogen, halogen, —CN, —OH, —$CF_3$, —SH, —$NH_2$ and an optionally substituted radical selected from the group of —$(C_1$-$C_6)$alkyl, —$(C_1$-$C_6)$alkylhalo, —$(C_3$-$C_7)$cycloalkyl, —$(C_1$-$C_6)$alkylcyano, —$(C_1$-$C_6)$alkylheteroaryl, —$(C_1$-$C_6)$alkylaryl, aryl, heteroaryl, heterocycle, —$(C_0$-$C_6)$alkyl-$OR^1$, —O—$(C_2$-$C_6)$alkyl-$OR^1$, —$NR^1(C_2$-$C_6)$alkyl-$OR^2$, —$(C_3$-$C_2)$cycloalkyl-$(C_1$-$C_6)$alkyl, —O—$(C_3$-$C_7)$cycloalkyl-$(C_1$-$C_6)$alkyl, —$NR^1$—$(C_3$-$C_2)$cycloalkyl-$(C_1$-$C_6)$alkyl, —$(C_1$-$C_6)$alkylhalo-$OR^1$, —$(C_1$-$C_6)$alkylhalo-$NR^1R^2$, —$(C_0$-$C_6)$alkyl-S—$R^1$, —O—$(C_2$-$C_6)$alkyl-S—$R^1$, —$NR^1$—$(C_2$-$C_6)$alkyl-S—$R^2$, —$(C_0$-$C_6)$alkyl-S(=O)—$R^1$, —O—$(C_1$-$C_6)$alkyl-S(=O)—$R^1$, —$NR^1$—$(C_1$-$C_6)$alkyl-S(=O)—$R^2$, —$(C_0$-$C_6)$alkyl-S(=O)$_2$—$R^1$, —O—$(C_1$-$C_6)$alkyl- S(=O)₂—R¹, —NR¹—(C₁-C₆)alkyl-S(=O)₂—R², —(C₀-C₆)alkyl-NR¹R², —O—(C₂-C₆)alkyl-NR¹R², —NR¹—(C₂-C₆)alkyl-NR²R³, —(C₀-C₆)alkyl-S(=O)₂NR¹R², —O—(C₁-C₆)alkyl-S(=O)₂NR¹R², —NR¹—(C₁-C₆)alkyl-S(=O)₂NR²R³, —(C₀-C₆)alkyl-NR¹—S(=O)₂R², —O—(C₂-C₆)alkyl-NR¹—S(=O)₂R², —NR¹—(C₂-C₆)alkyl-NR²—S(=O)₂R³, —(C₀-C₆)alkyl-C(=O)—NR¹R², —O—(C₁-C₆)alkyl-C(=O)—NR¹R², —NR¹—(C₁-C₆)alkyl-C(=O)—NR²R³, —(C₀-C₆)alkyl-NR¹C(=O)—R², —O—(C₂-C₆)alkyl-NR¹C(=O)—R², —NR¹—(C₂-C₆)alkyl-NR²C(=O)—R³, —(C₀-C₆)alkyl-C(=O)—R¹, —O—(C₁-C₆)alkyl-C(=O)—R¹, —NR¹—(C₁-C₆)alkyl-C(=O)—R², —(C₀-C₆)alkyl-NR¹—C(=O)—NR²R³, —O—(C₂-C₆)alkyl-NR¹—C(=O)—NR²R³ and —NR¹—(C₂-C₆)alkyl-NR²—C(=O)—NR³R⁴;

R¹, R², R³ and R⁴ are each independently hydrogen or an optionally substituted radical selected from the group of —(C₁-C₆)alkylhalo, —(C₁-C₆)alkyl, —(C₁-C₆)alkylcyano, —(C₃-C₇)cycloalkyl, —(C₄-C₁₀)alkylcycloalkyl, heteroaryl, —(C₁-C₆)alkylheteroaryl, aryl, heterocycle and —(C₁-C₆)alkylaryl;

Any two radicals of R (R¹, R², R³ or R⁴) may be taken together to form an optionally substituted 3 to 10 membered carbocyclic or heterocyclic ring;

M¹ is selected from an optionally substituted 3 to 10 membered ring selected from the group of aryl, heteroaryl, heterocyclic and cycloalkyl;

M³ is selected from the group of a hydrogen or an optionally substituted radical selected from the group of —(C₀-C₆)alkyl-C(=O)—R⁵, —(C₂-C₆)alkyl-S(O)—R⁵, —(C₀-C₆)alkyl-C(=O)NR⁵R⁶ and —(C₀-C₆)alkyl-S(O)₂—R⁵;

R⁵ and R⁶ are selected from the group of a hydrogen or an optionally substituted radical selected from the group of —(C₁-C₆)alkylhalo, —(C₁-C₆)alkyl, —(C₁-C₆)alkylcyano, —(C₃-C₇)cycloalkyl, —(C₄-C₁₀)alkylcycloalkyl, heteroaryl, —(C₁-C₆)alkylheteroaryl, aryl, heterocycle and —(C₁-C₆)alkylaryl;

provided that according to proviso (ii):
when M¹ is aryl, n is 1, B¹ is alkyl then M³ can not be an optionally substituted —S(O)₂aryl.

In a more preferred aspect of Formula (III), the invention provides a compound according to Formula (III-B),

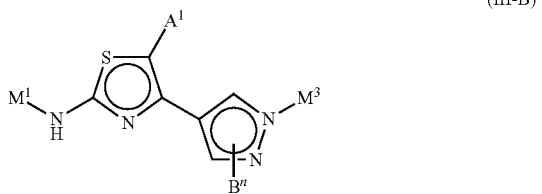

(III-B)

a pharmaceutically acceptable acid or base addition salt thereof, a stereochemically isomeric form thereof and an N-oxide form thereof, wherein:

A¹ radical is selected from the group of hydrogen, halogen, —CN, —OH, —CF₃, —SH, —NH₂ and an optionally substituted radical selected from the group of —(C₁-C₆)alkyl, —(C₁-C₆)alkylhalo, —(C₃-C₇)cycloalkyl, —(C₁-C₆)alkylcyano, —(C₁-C₆)alkylheteroaryl, —(C₁-C₆)alkylaryl, aryl, heteroaryl, heterocycle, —(C₀-C₆)alkyl-OR¹, —O—(C₂-C₆)alkyl-OR¹, —NR¹(C₂-C₆)alkyl-OR², —(C₃-C₇)cycloalkyl-(C₁-C₆)alkyl, —O—(C₃-C₇)cycloalkyl-(C₁-C₆)alkyl, —NR¹—(C₃-C₇)cycloalkyl-(C₁-C₆)alkyl, —(C₁-C₆)alkylhalo-OR¹, —(C₁-C₆)alkylhalo-NR¹R², —(C₀-C₆)alkyl-S—R¹, —O—(C₂-C₆)alkyl-S—R¹, —NR¹—(C₂-C₆)alkyl-S—R², —(C₀-C₆)alkyl-S(=O)—R¹, —O—(C₁-C₆)alkyl-S(=O)—R¹, —NR¹—(C₁-C₆)alkyl-S(=O)—R², —(C₀-C₆)alkyl-S(=O)₂—R¹, —O—(C₁-C₆)alkyl-S(=O)₂—R¹, —NR¹—(C₁-C₆)alkyl-S(=O)₂—R², —(C₀-C₆)alkyl-NR¹R², —O—(C₂-C₆)alkyl-NR¹R², —NR¹—(C₂-C₆)alkyl-NR²R³, —(C₀-C₆)alkyl-S(=O)₂NR¹R², —O—(C₁-C₆)alkyl-S(=O)₂NR¹R², —NR¹—(C₁-C₆)alkyl-S(=O)₂NR²R³, —(C₀-C₆)alkyl-NR¹—S(=O)₂R², —O—(C₂-C₆)alkyl-NR¹—S(=O)₂R², —NR¹—(C₂-C₆)alkyl-NR²—S(=O)₂R³, —(C₀-C₆)alkyl-C(=O)—NR¹R², —O—(C₁-C₆)alkyl-C(=O)—NR¹R², —NR¹—(C₁-C₆)alkyl-C(=O)—NR²R³, —(C₀-C₆)alkyl-NR¹C(=O)—R², —O—(C₂-C₆)alkyl-NR¹C(=O)—R², —NR¹—(C₂-C₆)alkyl-NR²C(=O)—R³, —(C₀-C₆)alkyl-C(=O)—R¹, —O—(C₁-C₆)alkyl-C(=O)—R¹, —NR¹—(C₁-C₆)alkyl-C(=O)—R², —(C₀-C₆)alkyl-NR¹—C(=O)—NR²R³, —O—(C₂-C₆)alkyl-NR¹—C(=O)—NR²R³ and —NR¹—(C₂-C₆)alkyl-NR²—C(=O)—;

R¹, R², R³ and R⁴ are each independently hydrogen or an optionally substituted radical selected from the group of —(C₁-C₆)alkylhalo, —(C₁-C₆)alkyl, —(C₁-C₆)alkylcyano, —(C₃-C₇)cycloalkyl, —(C₄-C₁₀)alkylcycloalkyl, heteroaryl, —(C₁-C₆)alkylheteroaryl, aryl, heterocycle and —(C₁-C₆)alkylaryl;

Any two radicals of R (R¹, R², R³ or R⁴) may be taken together to form an optionally substituted 3 to 10 membered carbocyclic or heterocyclic ring;

n is an integer ranging from 1 to 2;

B" radicals are each independently selected from the group of hydrogen, halogen, —CN, —OH, —CF₃, —SH, —NH₂ and an optionally substituted radical selected from the group of —(C₁-C₆)alkyl, —(C₁-C₆)alkylhalo, —(C₃-C₇)cyclo alkyl, —(C₁-C₆)alkylcyano, —(C₁-C₆)alkylheteroaryl, —(C₁-C₆)alkylaryl, aryl, heteroaryl, heterocycle, —(C₀-C₆)alkyl-OR⁵, —O—(C₂-C₆)alkyl-OR⁵, —NR⁵(C₂-C₆)alkyl-OR⁶, —(C₃-C₇)cycloalkyl-(C₁-C₆)alkyl, —O—(C₃-C₇)cycloalkyl-(C₁-C₆)alkyl, —NR⁵—(C₃-C₇)cycloalkyl-(C₁-C₆)alkyl, —(C₁-C₆)alkylhalo-OR⁵, —(C₁-C₆)alkylhalo-NR⁵R⁶, —(C₀-C₆)alkyl-S—R⁵, —O—(C₂-C₆)alkyl-S—R⁵, —NR⁵—(C₂-C₆)alkyl-S—R⁶, —(C₀-C₆)alkyl-S(=O)—R⁵, —O—(C₁-C₆)alkyl-S(=O)—R⁵, —NR⁵—(C₁-C₆)alkyl-S(=O)—R⁶, —(C₀-C₆)alkyl-S(=O)₂—R⁵, —O—(C₁-C₆)alkyl-S(=O)₂—R⁵, —NR⁵—(C₁-C₆)alkyl-S(=O)₂—R⁶, —(C₀-C₆)alkyl-NR⁵R⁶, —O—(C₂-C₆)alkyl-NR⁵R⁶, —NR⁵—(C₂-C₆)alkyl-NR⁶R⁷, —(C₀-C₆)alkyl-S(=O)₂NR⁵R⁶, —O—(C₁-C₆)alkyl-S(=O)₂NR⁵R⁶, —NR⁵—(C₁-C₆)alkyl-S(=O)₂NR⁶R⁷, —(C₀-C₆)alkyl-NR⁵—S(=O)₂R⁶, —O—(C₂-C₆)alkyl-NR⁵—S(=O)₂R⁶, —NR⁵—(C₂-C₆)alkyl-NR⁶—S(=O)₂R⁷, —(C₀-C₆)alkyl-C(=O)—NR⁵R⁶, —O—(C₁-C₆)alkyl-C(=O)—NR⁵R⁶, —NR⁵—(C₁-C₆)alkyl-C(=O)—NR⁶R⁷, —(C₀-C₆)alkyl-NR⁵C(=O)—R⁶, —O—(C₂-C₆)alkyl-NR⁵C(=O)—R⁶, —NR⁵—(C₂-C₆)alkyl-NR⁶C(=O)—R⁷, —(C₀-C₆)alkyl-C(=O)—R⁵, —O—(C₁-C₆)alkyl-C(=O)—R⁵, —NR⁵—(C₁-C₆)alkyl-C(=O)—R⁶, —(C₀-C₆)alkyl-NR⁵—C(=O)—NR⁶R⁷, —O—(C₂-C₆)alkyl-NR⁵—C(=O)—NR⁶R⁷ and —NR⁵—(C₂-C₆)alkyl-NR⁶—C(=O)—NR⁷R⁸;

R⁵, R⁶, R⁷ and R⁸ are each independently hydrogen or an optionally substituted radical selected from the group of —(C₁-C₆)alkylhalo, —(C₁-C₆)alkyl, —(C₁-C₆)alkylcyano, —(C₃-C₇)cycloalkyl, —(C₄-C₁₀)alkylcycloalkyl, heteroaryl, —(C₁-C₆)alkylheteroaryl, aryl, heterocycle and —(C₁-C₆)alkylaryl;

Any two radicals of R (R⁵, R⁶, R⁷ or R⁸) may be taken together to form an optionally substituted 3 to 10 membered carbocyclic or heterocyclic ring;

$M^1$ is selected from an optionally substituted 3 to 10 membered ring selected from the group of aryl, heteroaryl, heterocyclic and cycloalkyl;

$M^3$ is selected from the group of a hydrogen or an optionally substituted radical selected from the group of —$(C_0$-$C_6)$alkyl-C(=O)—$R^9$, —$(C_2$-$C_6)$alkyl-S(O)—$R^9$, —$(C_0$-$C_6)$alkyl-C(=O)NR$^9$R$^{10}$ and —$(C_0$-$C_6)$alkyl-S(O)$_2$—$R^9$;

$R^9$ and $R^{10}$ are selected from the group of a hydrogen or an optionally substituted radical selected from the group of —$(C_1$-$C_6)$alkylhalo, —$(C_1$-$C_6)$alkyl, —$(C_1$-$C_6)$alkylcyano, —$(C_3$-$C_7)$cycloalkyl, —$(C_4$-$C_{10})$alkylcycloalkyl, heteroaryl, —$(C_1$-$C_6)$alkylheteroaryl, aryl, heterocycle and —$(C_1$-$C_6)$alkylaryl;

provided that according to proviso (i):
when $M^3$ is H, $A^1$ is H, n is 1 and $B^1$ is —CN then $M^1$ can not be an aryl optionally substituted by —O—$(C_1$-$C_8)$alkyl.

In a more preferred aspect of Formula (III-B), the invention provides a compound according to Formula (III-B), wherein:
$A^1$ radical is selected from the group of hydrogen, halogen, —CN, —OH, —CF$_3$, —SH, —NH$_2$ and an optionally substituted radical selected from the group of —$(C_1$-$C_6)$alkyl, —$(C_1$-$C_6)$alkylhalo, —$(C_3$-$C_7)$cycloalkyl, —$(C_1$-$C_6)$alkylcyano, —$(C_1$-$C_6)$alkylheteroaryl, —$(C_1$-$C_6)$alkylaryl, aryl, heteroaryl, heterocycle, —$(C_0$-$C_6)$alkyl-OR$^1$, —O—$(C_2$-$C_6)$alkyl-OR$^1$, —NR$^1$$(C_2$-$C_6)$alkyl-OR$^2$, —$(C_3$-$C_7)$cycloalkyl-$(C_1$-$C_6)$alkyl, —O—$(C_3$-$C_7)$cycloalkyl-$(C_1$-$C_6)$alkyl, —NR$^1$—$(C_3$-$C_7)$cycloalkyl-$(C_1$-$C_6)$alkyl, —$(C_1$-$C_6)$alkylhalo-OR$^1$, —$(C_1$-$C_6)$alkylhalo-NR$^1$R$^2$, —$(C_0$-$C_6)$alkyl-S—R$^1$, —O—$(C_2$-$C_6)$alkyl-S—R$^1$, —NR$^1$—$(C_2$-$C_6)$alkyl-S—R$^2$, —$(C_0$-$C_6)$alkyl-S(=O)—R$^1$, —O—$(C_1$-$C_6)$alkyl-S(=O)—R$^1$, —NR$^1$—$(C_1$-$C_6)$alkyl-S(=O)—R$^2$, —$(C_0$-$C_6)$alkyl-S(=O)$_2$—R$^1$, —O—$(C_1$-$C_6)$alkyl-S(=O)$_2$—R$^1$, —NR$^1$—$(C_1$-$C_6)$alkyl-S(=O)$_2$—R$^2$, —$(C_0$-$C_6)$alkyl-NR$^1$R$^2$, —O—$(C_2$-$C_6)$alkyl-NR$^1$R$^2$, —NR$^1$—$(C_2$-$C_6)$alkyl-NR$^2$R$^3$, —$(C_0$-$C_6)$alkyl-S(=O)$_2$NR$^1$R$^2$, —O—$(C_1$-$C_6)$alkyl-S(=O)$_2$NR$^1$R$^2$, —NR$^1$—$(C_1$-$C_6)$alkyl-S(=O)$_2$NR$^2$R$^3$, —$(C_0$-$C_6)$alkyl-NR$^1$—S(=O)$_2$R$^2$, —O—$(C_2$-$C_6)$alkyl-NR$^1$—S(=O)$_2$R$^2$, —NR$^1$—$(C_2$-$C_6)$alkyl-NR$^2$—S(=O)$_2$R$^3$, —$(C_0$-$C_6)$alkyl-C(=O)—NR$^1$R$^2$, —O—$(C_1$-$C_6)$alkyl-C(=O)—NR$^1$R$^2$, —NR$^1$—$(C_1$-$C_6)$alkyl-C(=O)—NR$^2$R$^3$, —$(C_0$-$C_6)$alkyl-NR$^1$C(=O)—R$^2$, —O—$(C_2$-$C_6)$alkyl-NR$^1$C(=O)—R$^2$, —NR$^1$—$(C_2$-$C_6)$alkyl-NR$^2$C(=O)—R$^3$, —$(C_0$-$C_6)$alkyl-C(=O)—R$^1$, —O—$(C_1$-$C_6)$alkyl-C(=O)—R$^1$, —NR$^1$—$(C_1$-$C_6)$alkyl-C(=O)—R$^2$, —$(C_0$-$C_6)$alkyl-NR$^1$—C(=O)—NR$^2$R$^3$, —O—$(C_2$-$C_6)$alkyl-NR$^1$—C(=O)—NR$^2$R$^3$ and —NR$^1$—$(C_2$-$C_6)$alkyl-NR$^2$—C(=O)—;

$R^1$, $R^2$, $R^3$ and $R^4$ are each independently hydrogen or an optionally substituted radical selected from the group of —$(C_1$-$C_6)$alkylhalo, —$(C_1$-$C_6)$alkyl, —$(C_1$-$C_6)$alkylcyano, —$(C_3$-$C_7)$cycloalkyl, —$(C_4$-$C_{10})$alkylcycloalkyl, heteroaryl, —$(C_1$-$C_6)$alkylheteroaryl, aryl, heterocycle and —$(C_1$-$C_6)$alkylaryl;

Any two radicals of R ($R^1$, $R^2$, $R^3$ or $R^4$) may be taken together to form an optionally substituted 3 to 10 membered carbocyclic or heterocyclic ring;

n is an integer ranging from 1 to 2;

$B''$ radicals are each independently selected from the group of hydrogen, halogen, —CN, —OH, —CF$_3$, —SH, —NH$_2$ and an optionally substituted radical selected from the group of —$(C_1$-$C_6)$alkyl, —$(C_1$-$C_6)$alkylhalo, —$(C_3$-$C_2)$cyclo alkyl, —$(C_1$-$C_6)$alkylcyano, —$(C_1$-$C_6)$alkylheteroaryl, —$(C_1$-$C_6)$alkylaryl, aryl, heteroaryl, heterocycle, —$(C_0$-$C_6)$alkyl-OR$^5$, —O—$(C_2$-$C_6)$alkyl-OR$^5$, —NR$^5$$(C_2$-$C_6)$alkyl-OR$^6$, —$(C_3$-$C_7)$cycloalkyl-$(C_1$-$C_6)$alkyl, —O—$(C_3$-$C_7)$cycloalkyl-$(C_1$-$C_6)$alkyl, —NR$^5$—$(C_3$-$C_2)$cycloalkyl-$(C_1$-$C_6)$alkyl, —$(C_1$-$C_6)$alkylhalo-OR$^5$, —$(C_1$-$C_6)$alkylhalo-NR$^5$R$^6$, —$(C_0$-$C_6)$alkyl-S—R$^5$, —O—$(C_2$-$C_6)$alkyl-S—R$^5$, —NR$^5$—$(C_2$-$C_6)$alkyl-S—R$^6$, —$(C_0$-$C_6)$alkyl-S(=O)—R$^5$, —O—$(C_1$-$C_6)$alkyl-S(=O)—R$^5$, —NR$^5$—$(C_1$-$C_6)$alkyl-S(=O)—R$^6$, —$(C_0$-$C_6)$alkyl-S(=O)$_2$—R$^5$, —O—$(C_1$-$C_6)$alkyl-S(=O)$_2$—R$^5$, —NR$^5$—$(C_1$-$C_6)$alkyl-S(=O)$_2$—R$^6$, —$(C_0$-$C_6)$alkyl-NR$^5$R$^6$, —O—$(C_2$-$C_6)$alkyl-NR$^5$R$^6$, —NR$^5$—$(C_2$-$C_6)$alkyl-NR$^6$R$^7$, —$(C_0$-$C_6)$alkyl-S(=O)$_2$NR$^5$R$^6$, —O—$(C_1$-$C_6)$alkyl-S(=O)$_2$NR$^5$R$^6$, —NR$^5$—$(C_1$-$C_6)$alkyl-S(=O)$_2$NR$^6$R$^7$, —$(C_0$-$C_6)$alkyl-NR$^5$—S(=O)$_2$R$^6$, —O—$(C_2$-$C_6)$alkyl-NR$^5$—S(=O)$_2$R$^6$, —NR$^5$—$(C_2$-$C_6)$alkyl-NR$^6$—S(=O)$_2$R$^7$, —$(C_0$-$C_6)$alkyl-C(=O)—NR$^5$R$^6$, —O—$(C_1$-$C_6)$alkyl-C(=O)—NR$^5$R$^6$, —NR$^5$—$(C_1$-$C_6)$alkyl-C(=O)—NR$^6$R$^7$, —$(C_0$-$C_6)$alkyl-NR$^5$C(=O)—R$^6$, —O—$(C_2$-$C_6)$alkyl-NR$^5$C(=O)—R$^6$, —NR$^5$—$(C_2$-$C_6)$alkyl-NR$^6$C(=O)—R$^7$, —$(C_0$-$C_6)$alkyl-C(=O)—R$^5$, —O—$(C_1$-$C_6)$alkyl-C(=O)—R$^5$, —NR$^5$—$(C_1$-$C_6)$alkyl-C(=O)—R$^6$, —$(C_0$-$C_6)$alkyl-NR$^5$—C(=O)—NR$^6$R$^7$, —O—$(C_2$-$C_6)$alkyl-NR$^5$—C(=O)—NR$^6$R$^7$ and —NR$^5$—$(C_2$-$C_6)$alkyl-NR$^6$—C(=O)—NR$^7$R$^8$;

$R^5$, $R^6$, $R^7$ and $R^8$ are each independently hydrogen or an optionally substituted radical selected from the group of —$(C_1$-$C_6)$alkylhalo, —$(C_1$-$C_6)$alkyl, —$(C_1$-$C_6)$alkylcyano, —$(C_3$-$C_7)$cycloalkyl, —$(C_4$-$C_{10})$alkylcycloalkyl, heteroaryl, —$(C_1$-$C_6)$alkylheteroaryl, aryl, heterocycle and —$(C_1$-$C_6)$alkylaryl;

Any two radicals of R ($R^5$, $R^6$, $R^7$ or $R^8$) may be taken together to form an optionally substituted 3 to 10 membered carbocyclic or heterocyclic ring;

$M^1$ is selected from an optionally substituted 3 to 10 membered ring selected from the group of aryl;

$M^3$ is selected from the group of a hydrogen or an optionally substituted radical selected from the group of —$(C_0$-$C_6)$alkyl-C(=O)—$R^9$, —$(C_2$-$C_6)$alkyl-S(O)—$R^9$, —$(C_0$-$C_6)$alkyl-C(=O)NR$^9$R$^{10}$ and —$(C_0$-$C_6)$alkyl-S(O)$_2$—$R^9$;

$R^9$ and $R^{10}$ are selected from the group of a hydrogen or an optionally substituted radical selected from the group of —$(C_1$-$C_6)$alkylhalo, —$(C_1$-$C_6)$alkyl, —$(C_1$-$C_6)$alkylcyano, —$(C_3$-$C_7)$cycloalkyl, —$(C_4$-$C_{10})$alkylcycloalkyl, heteroaryl, —$(C_1$-$C_6)$alkylheteroaryl, aryl, heterocycle and —$(C_1$-$C_6)$alkylaryl;

provided that according to proviso (i):
when $M^3$ is H, $A^1$ is H, n is 1 and $B^1$ is —CN then $M^1$ can not be an aryl optionally substituted by —O—$(C_1$-$C_8)$alkyl.

In a more preferred aspect of Formula (III-B), the invention provides a compound according to Formula (III-B), wherein:
$A^1$ radical is selected from the group of hydrogen, halogen, —CN, —OH, —CF$_3$, —SH, —NH$_2$ and an optionally substituted radical selected from the group of —$(C_1$-$C_6)$alkyl, —$(C_1$-$C_6)$alkylhalo, —$(C_3$-$C_7)$cycloalkyl, —$(C_1$-$C_6)$alkylcyano, —$(C_1$-$C_6)$alkylheteroaryl, —$(C_1$-$C_6)$alkylaryl, aryl, heteroaryl, heterocycle, —$(C_0$-$C_6)$alkyl-OR$^1$, —O—$(C_2$-$C_6)$alkyl-OR$^1$, —NR$^1$$(C_2$-$C_6)$alkyl-OR$^2$, —$(C_3$-$C_7)$cycloalkyl-$(C_1$-$C_6)$alkyl, —O—$(C_3$-$C_7)$cycloalkyl-$(C_1$-$C_6)$alkyl, —NR$^1$—$(C_3$-$C_7)$cycloalkyl-$(C_1$-$C_6)$alkyl, —$(C_1$-$C_6)$alkylhalo-OR$^1$, —$(C_1$-$C_6)$alkylhalo-NR$^1$R$^2$, —$(C_0$-$C_6)$alkyl-S—R$^1$, —O—$(C_2$-$C_6)$alkyl-S—R$^1$, —NR$^1$—$(C_2$-$C_6)$alkyl-S—R$^2$, —$(C_0$-$C_6)$alkyl-S(=O)—R$^1$, —O—$(C_1$-$C_6)$alkyl-S(=O)—R$^1$, —NR$^1$—$(C_1$-$C_6)$alkyl-S(=O)—R$^2$, —$(C_0$-$C_6)$alkyl-S(=O)$_2$—R$^1$, —O—$(C_1$-$C_6)$alkyl-S(=O)$_2$—R$^1$, —NR$^1$—$(C_1$-$C_6)$alkyl-S(=O)$_2$—R$^2$, —$(C_0$-$C_6)$alkyl-NR$^1$R$^2$, —O—$(C_2$-$C_6)$alkyl-NR$^1$R$^2$, —NR$^1$—$(C_2$-$C_6)$alkyl-NR$^2$R$^3$, —$(C_0$-$C_6)$alkyl-S(=O)$_2$NR$^1$R$^2$, —O—$(C_1$-$C_6)$alkyl-S(=O)$_2$NR$^1$R$^2$, —NR$^1$—$(C_1$-$C_6)$alkyl-S(=O)$_2$NR$^2$R$^3$, —$(C_0$-$C_6)$alkyl-NR$^1$—S(=O)$_2$R$^2$, —NR$^1$—$(C_2$-$C_6)$alkyl-NR$^2$—S(=O)$_2$R$^3$, —$(C_0$-$C_6)$alkyl-C(=O)—NR$^1$R$^2$, —O—$(C_1$-$C_6)$alkyl-C(=O)—NR$^1$R$^2$, —NR$^1$—$(C_1$-$C_6)$alkyl-C(=O)—

NR$^2$R$^3$, —(C$_0$-C$_6$)alkyl-NR$^1$C(=O)—R$^2$, —O—(C$_2$-C$_6$)alkyl-NR$^1$C(=O)—R$^2$, —NR$^1$—(C$_2$-C$_6$)alkyl-NR$^2$C(=O)—R$^3$, —(C$_0$-C$_6$)alkyl-C(=O)—R$^1$, —O—(C$_1$-C$_6$)alkyl-C(=O)—R$^1$, —NR$^1$—(C$_1$-C$_6$)alkyl-C(=O)—R$^2$, —(C$_0$-C$_6$)alkyl-NR$^1$—C(=O)—NR$^2$R$^3$, —O—(C$_2$-C$_6$)alkyl-NR$^1$—C(=O)—NR$^2$R$^3$ and —NR$^1$—(C$_2$-C$_6$)alkyl-NR$^2$—C(=O)—;

R$^1$, R$^2$, R$^3$ and R$^4$ are each independently hydrogen or an optionally substituted radical selected from the group of —(C$_1$-C$_6$)alkylhalo, —(C$_1$-C$_6$)alkyl, —(C$_1$-C$_6$)alkylcyano, —(C$_3$-C$_7$)cycloalkyl, —(C$_4$-C$_{10}$)alkylcycloalkyl, heteroaryl, —(C$_1$-C$_6$)alkylheteroaryl, aryl, heterocycle and —(C$_1$-C$_6$)alkylaryl;

Any two radicals of R R$^1$, R$^2$, R$^3$ or R$^4$) may be taken together to form an optionally substituted 3 to 10 membered carbocyclic or heterocyclic ring;

n is an integer ranging from 1 to 2;

B$^6$ radicals are each independently selected from the group of hydrogen, halogen, —CN, —OH, —CF$_3$, —SH, —NH$_2$ and an optionally substituted radical selected from the group of —(C$_1$-C$_6$)alkyl, —(C$_1$-C$_6$)alkylhalo, —(C$_3$-C$_2$)cyclo alkyl, —(C$_1$-C$_6$)alkylcyano, —(C$_1$-C$_6$)alkylheteroaryl, —(C$_1$-C$_6$)alkylaryl, aryl, heteroaryl, heterocycle, —(C$_0$-C$_6$)alkyl-OR$^5$, —O—(C$_2$-C$_6$)alkyl-OR$^5$, —NR$^5$(C$_2$-C$_6$)alkyl-OR$^6$, —(C$_3$-C$_7$)cycloalkyl-(C$_1$-C$_6$)alkyl, —O—(C$_3$-C$_7$)cycloalkyl-(C$_1$-C$_6$)alkyl, —NR$^5$—(C$_3$-C$_2$)cycloalkyl-(C$_1$-C$_6$)alkyl, —(C$_1$-C$_6$)alkylhalo-OR$^5$, —(C$_1$-C$_6$)alkylhalo-NR$^5$R$^6$, —(C$_0$-C$_6$)alkyl-S—R$^5$, —O—(C$_2$-C$_6$)alkyl-S—R$^5$, —NR$^5$—(C$_2$-C$_6$)alkyl-S—R$^6$, —(C$_0$-C$_6$)alkyl-S(=O)—R$^5$, —O—(C$_1$-C$_6$)alkyl-S(=O)—R$^5$, —NR$^5$—(C$_1$-C$_6$)alkyl-S(=O)—R$^6$, —(C$_0$-C$_6$)alkyl-S(=O)$_2$—R$^5$, —O—(C$_1$-C$_6$)alkyl-S(=O)$_2$—R$^5$, —NR$^5$—(C$_1$-C$_6$)alkyl-S(=O)$_2$—R$^6$, —(C$_0$-C$_6$)alkyl-NR$^5$R$^6$, —O—(C$_2$-C$_6$)alkyl-NR$^5$R$^6$, —NR$^5$—(C$_2$-C$_6$)alkyl-NR$^6$R$^2$, —(C$_0$-C$_6$)alkyl-S(=O)$_2$NR$^5$R$^6$, —O—(C$_1$-C$_6$)alkyl-S(=O)$_2$NR$^5$R$^6$, —NR$^5$—(C$_1$-C$_6$)alkyl-S(=O)$_2$NR$^6$R$^2$, —(C$_0$-C$_6$)alkyl-NR$^5$—S(=O)$_2$R$^6$, —O—(C$_2$-C$_6$)alkyl-NR$^5$—S(=O)$_2$R$^6$, —NR$^5$—(C$_2$-C$_6$)alkyl-NR$^6$—S(=O)$_2$R$^2$, —(C$_0$-C$_6$)alkyl-C(=O)—NR$^5$R$^6$, —O—(C$_1$-C$_6$)alkyl-C(=O)—NR$^5$R$^6$, —NR$^5$—(C$_1$-C$_6$)alkyl-C(=O)—NR$^6$R$^2$, —(C$_0$-C$_6$)alkyl-NR$^5$C(=O)—R$^6$, —O—(C$_2$-C$_6$)alkyl-NR$^5$C(=O)—R$^6$, —NR$^5$—(C$_2$-C$_6$)alkyl-NR$^6$C(=O)—R$^2$, —(C$_0$-C$_6$)alkyl-C(=O)—R$^5$, —O—(C$_1$-C$_6$)alkyl-C(=O)—R$^5$, —NR$^5$—(C$_1$-C$_6$)alkyl-C(=O)—R$^6$, —(C$_0$-C$_6$)alkyl-NR$^5$—C(=O)—NR$^6$R$^2$, —O—(C$_2$-C$_6$)alkyl-NR$^5$—C(=O)—NR$^6$R$^2$ and —NR$^5$—(C$_2$-C$_6$)alkyl-NR$^6$—C(=O)—NR$^7$R$^8$;

R$^5$, R$^6$, R$^7$ and R$^8$ are each independently hydrogen or an optionally substituted radical selected from the group of —(C$_1$-C$_6$)alkylhalo, —(C$_1$-C$_6$)alkyl, —(C$_1$-C$_6$)alkylcyano, —(C$_3$-C$_7$)cycloalkyl, —(C$_4$-C$_{10}$)alkylcycloalkyl, heteroaryl, —(C$_1$-C$_6$)alkylheteroaryl, aryl, heterocycle and —(C$_1$-C$_6$)alkylaryl;

Any two radicals of R (R$^5$, R$^6$, R$^7$ or R$^8$) may be taken together to form an optionally substituted 3 to 10 membered carbocyclic or heterocyclic ring;

M$^1$ is selected from an optionally substituted 3 to 10 membered ring selected from the group of heteroaryl, heterocyclic and cycloalkyl;

M$^3$ is selected from the group of a hydrogen or an optionally substituted radical selected from the group of —(C$_0$-C$_6$)alkyl-C(=O)—R$^9$, —(C$_2$-C$_6$)alkyl-S(O)—R$^9$, —(C$_0$-C$_6$)alkyl-C(=O)NR$^9$R$^{10}$ and —(C$_0$-C$_6$)alkyl-S(O)$_2$—R$^9$; and R$^9$ and R$^{16}$ are selected from the group of a hydrogen or an optionally substituted radical selected from the group of —(C$_1$-C$_6$)alkylhalo, —(C$_1$-C$_6$)alkyl, —(C$_1$-C$_6$)alkylcyano, —(C$_3$-C$_7$)cyclo alkyl, —(C$_4$-C$_{10}$)alkylcycloalkyl, heteroaryl, —(C$_1$-C$_6$)alkylheteroaryl, aryl, heterocycle and —(C$_1$-C$_6$)alkylaryl.

Particular preferred compounds of the invention are compounds as mentioned in the following list (List of Particular Preferred Compounds), as well as a pharmaceutically acceptable acid or base addition salt thereof, a stereochemically isomeric form thereof and an N-oxide form thereof.

3-(3-Methyl-1H-pyrazol-4-yl)-N-phenyl-1,2,4-thiadiazol-5-amine 1-(3-Methyl-4-(5-(phenylamino)-1,2,4-thiadiazol-3-yl)-1H-pyrazol-1-yl)ethanone N-(2-Chlorophenyl)-3-(3-methyl-1H-pyrazol-4-yl)-1,2,4-thiadiazol-5-amine N-(2-Fluorophenyl)-3-(3-methyl-1H-pyrazol-4-yl)-1,2,4-thiadiazol-5-amine 3-(3-Methyl-1H-pyrazol-4-yl)-N-(pyridin-2-yl)-1,2,4-thiadiazol-5-amine N-Phenyl-3-(1H-pyrazol-4-yl)-1,2,4-thiadiazol-5-amine 4-(3-Methyl-1H-pyrazol-4-yl)-N-phenylthiazol-2-amine N-Phenyl-3-(3-propyl-1H-pyrazol-4-yl)-1,2,4-thiadiazol-5-amine 3-(3-Propyl-1H-pyrazol-4-yl)-N-(pyridin-2-yl)-1,2,4-thiadiazol-5-amine N-(Pyridin-2-yl)-3-(3-(trifluoromethyl)-1H-pyrazol-4-yl)-1,2,4-thiadiazol-5-amine 4-(3-Methyl-1H-pyrazol-4-yl)-N-(pyridin-2-yl)thiazol-2-amine N-(Pyridin-2-yl)-4-(3-(trifluoromethyl)-1H-pyrazol-4-yl)thiazol-2-amine and 4-(3-Isopropyl-1H-pyrazol-4-yl)-N-(pyridin-2-yl)thiazol-2-amine N-(2,6-Difluorophenyl)-4-(3-methyl-1H-pyrazol-4-yl)thiazol-2-amine 5-Methyl-4-(3-methyl-1H-pyrazol-4-yl)-N-(pyridin-2-yl)thiazol-2-amine 5-Methyl-4-(1H-pyrazol-4-yl)-N-(pyridin-2-yl)thiazol-2-amine N-(2,5-Difluorophenyl)-4-(3-methyl-1H-pyrazol-4-yl)thiazol-2-amine 5-Methyl-N-(6-methylpyridin-2-yl)-4-(1H-pyrazol-4-yl)thiazol-2-amine 5-Methyl-N-(4-methylpyridin-2-yl)-4-(1H-pyrazol-4-yl)thiazol-2-amine N-(3,5-Difluoropyridin-2-yl)-5-methyl-4-(1H-pyrazol-4-yl)thiazol-2-amine 4-(3-Methyl-1H-pyrazol-4-yl)-N-(4-methylpyridin-2-yl)thiazol-2-amine 5-Ethyl-4-(1H-pyrazol-4-yl)-N-(pyridin-2-yl)thiazol-2-amine 4-(3-Methyl-1H-pyrazol-4-yl)-N-(6-methylpyridin-2-yl)thiazol-2-amine N-(5-Fluoropyridin-2-yl)-5-methyl-4-(1H-pyrazol-4-yl)thiazol-2-amine 4-(1H-Pyrazol-4-yl)-N-(pyridin-2-yl)thiazol-2-amine 2-Methyl-1-(4-(5-methyl-2-(pyridin-2-ylamino)thiazol-4-yl)-1H-pyrazol-1-yl)propan-1-one 4-(5-Methyl-2-(pyridin-2-ylamino)thiazol-4-yl)-1H-pyrazole-1-carboxamide Cyclohexyl(4-(5-methyl-2-(pyridin-2-ylamino)thiazol-4-yl)-1H-pyrazol-1-yl)methanone N-Cyclohexyl-5-methyl-4-(1H-pyrazol-4-yl)thiazol-2-amine 2-Methyl-1-(4-(5-methyl-2-(6-methylpyridin-2-ylamino)thiazol-4-yl)-1H-pyrazol-1-yl)propan-1-one N-(6-Chloropyridin-2-yl)-5-methyl-4-(1H-pyrazol-4-yl)thiazol-2-amine 5-Chloro-4-(1H-pyrazol-4-yl)-N-(pyridin-2-yl)thiazol-2-amine
N-(6-Fluoropyridin-2-yl)-5-methyl-4-(1H-pyrazol-4-yl)thiazol-2-amine
(4-(5-Methyl-2-(pyridin-2-ylamino)thiazol-4-yl)-1H-pyrazol-1-yl)(piperidin-1-yl)methanone
3-(1H-Pyrazol-4-yl)-N-(pyridin-2-yl)-1,2,4-thiadiazol-5-amine
2-Methyl-1-(4-(5-(pyridin-2-ylamino)-1,2,4-thiadiazol-3-yl)-1H-pyrazol-1-yl)propan-1-one
N-Cyclopentyl-5-methyl-4-(1H-pyrazol-4-yl)thiazol-2-amine
N-(6-Methylpyridin-2-yl)-3-(1H-pyrazol-4-yl)-1,2,4-thiadiazol-5-amine
5-Methyl-N-(pyrazin-2-yl)-4-(1H-pyrazol-4-yl)thiazol-2-amine
3-(3-Methyl-1H-pyrazol-4-yl)-N-(6-methylpyridin-2-yl)-1,2,4-thiadiazol-5-amine
N-(6-Chloropyridin-2-yl)-3-(3-methyl-1H-pyrazol-4-yl)-1,2,4-thiadiazol-5-amine
N-(6-Chloropyridin-2-yl)-3-(1H-pyrazol-4-yl)-1,2,4-thiadiazol-5-amine
N-(6-Fluoropyridin-2-yl)-3-(3-methyl-1H-pyrazol-4-yl)-1,2,4-thiadiazol-5-amine
N-(3,5-Difluoropyridin-2-yl)-3-(3-methyl-1H-pyrazol-4-yl)-1,2,4-thiadiazol-5-amine
5-Methyl-4-(1-(methylsulfonyl)-1H-pyrazol-4-yl)-N-(pyridin-2-yl)thiazol-2-amine
N-(3-Fluoropyridin-2-yl)-5-methyl-4-(1H-pyrazol-4-yl)thiazol-2-amine
4-(1H-Pyrazol-4-yl)-2-(pyridin-2-ylamino)thiazol-5-carbonitrile
N-(6-Ethylpyridin-2-yl)-5-methyl-4-(1H-pyrazol-4-yl)thiazol-2-amine
N-(6-Chloropyridin-2-yl)-4-(1H-pyrazol-4-yl)thiazol-2-amine
N-Isopropyl-4-(5-methyl-2-(pyridin-2-ylamino)thiazol-4-yl)-1H-pyrazole-1-carboxamide
N-(6-Fluoropyridin-2-yl)-4-(1H-pyrazol-4-yl)thiazol-2-amine
5-Chloro-N-(6-methylpyridin-2-yl)-4-(1H-pyrazol-4-yl)thiazol-2-amine
N-(2,5-Difluorophenyl)-6-(1H-pyrazol-4-yl)pyridin-2-amine
N-(6-Methylpyridin-2-yl)-4-(1H-pyrazol-4-yl)thiazol-2-amine
4-(1H-Pyrazol-4-yl)-N-(pyridin-2-yl)-5-(trifluoromethyl)thiazol-2-amine
5-Phenyl-4-(1H-pyrazol-4-yl)-N-(pyridin-2-yl)thiazol-2-amine
5-Fluoro-4-(1H-pyrazol-4-yl)-N-(pyridin-2-yl)thiazol-2-amine
(4-(1H-Pyrazol-4-yl)-2-(pyridin-2-ylamino)thiazol-5-yl)methanol
N-(6-Methoxypyridin-2-yl)-5-methyl-4-(1H-pyrazol-4-yl)thiazol-2-amine
N-Cyclopropyl-4-(5-methyl-2-(pyridin-2-ylamino)thiazol-4-yl)-1H-pyrazole-1-carboxamide
4-(3-Cyclopropyl-1H-pyrazol-4-yl)-N-(pyridin-2-yl)thiazol-2-amine
4-(3-Ethyl-1H-pyrazol-4-yl)-N-(pyridin-2-yl)thiazol-2-amine and
4-(2-(6-Fluoropyridin-2-ylamino)-5-methylthiazol-4-yl)-1H-pyrazole-1-carboxamide

DEFINITION OF TERMS

Listed below are definitions of various terms used in the specification and claims to describe the present invention.

For the avoidance of doubt it is to be understood that in this specification "$(C_1\text{-}C_6)$" means a carbon radical having 1, 2, 3, 4, 5 or 6 carbon atoms. "$(C_0\text{-}C_6)$" means a carbon radical having 0, 1, 2, 3, 4, 5 or 6 carbon atoms. In this specification "C" means a carbon atom, "N" means a nitrogen atom, "O" means an oxygen atom and "S" means a sulphur atom.

In the case where a subscript is the integer 0 (zero) the radical to which the subscript refers, indicates that the radical is absent, i.e. there is a direct bond between the radicals.

In this specification, unless stated otherwise, the term "bond" refers to a saturated covalent bond. When two or more bonds are adjacent to one another, they are assumed to be equal to one bond. For example, a radical -A-B—, wherein both A and B may be a bond, the radical is depicting a single bond.

In this specification, unless stated otherwise, the term "alkyl" includes both straight and branched chain alkyl radicals and may be methyl, ethyl, n-propyl, i-propyl, n-butyl, i-butyl, s-butyl, t-butyl, n-pentyl, i-pentyl, t-pentyl, neo-pentyl, n-hexyl, i-hexyl or t-hexyl. The term "$(C_0\text{-}C_3)$alkyl" refers to an alkyl radical having 0, 1, 2 or 3 carbon atoms and may be methyl, ethyl, n-propyl and i-propyl.

In this specification, unless stated otherwise, the term "cycloalkyl" refers to an optionally substituted carbocycle containing no heteroatoms, including mono-, bi-, and tricyclic saturated carbocycles, as well as fused ring systems. Such fused ring systems can include one ring that is partially or fully unsaturated such as a benzene ring to form fused ring systems such as benzo-fused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, fluorenyl and 1,2,3,4-tetrahydronaphthalene and the like. The term "$(C_3\text{-}C_7)$cycloalkyl" may be cyclopropyl, cyclobutyl, cyclopentyl, cyclohexyl, cycloheptyl and the like.

In this specification, unless stated otherwise, the term "alkenyl" includes both straight and branched chain alkenyl radicals. The term "$(C_2\text{-}C_6)$alkenyl" refers to an alkenyl radical having 2 to 6 carbon atoms and one or two double bonds, and may be, but is not limited to vinyl, allyl, propenyl, i-propenyl, butenyl, i-butenyl, crotyl, pentenyl, i-pentenyl and hexenyl.

In this specification, unless stated otherwise, the term "alkynyl" includes both straight and branched chain alkynyl radicals. The term $(C_2\text{-}C_6)$alkynyl having 2 to 6 carbon atoms and one or two triple bonds, and may be, but is not limited to ethynyl, propargyl, butynyl, i-butynyl, pentynyl, i-pentynyl and hexynyl.

The term "aryl" refers to an optionally substituted monocyclic or bicyclic hydrocarbon ring system containing at least one unsaturated aromatic ring. Examples and suitable values of the term "aryl" are phenyl, naphthyl, 1,2,3,4-tetrahydronaphthyl, indyl, indenyl and the like.

In this specification, unless stated otherwise, the term "heteroaryl" refers to an optionally substituted monocyclic or bicyclic unsaturated, aromatic ring system containing at least one heteroatom selected independently from N, O or S. Examples of "heteroaryl" may be, but are not limited to thienyl, pyridyl, thiazolyl, isothiazolyl, furyl, pyrrolyl, triazolyl, imidazolyl, oxadiazolyl, oxazolyl, isoxazolyl, pyrazolyl, imidazolonyl, oxazolonyl, thiazolonyl, tetrazolyl, thiadiazolyl, benzoimidazolyl, benzooxazolyl, benzothiazolyl, tetrahydrotriazolopyridyl, tetrahydrotriazolopyrimidinyl, benzofuryl, benzothiophenyl, thionaphthyl, indolyl, isoindolyl, pyridonyl, pyridazinyl, pyrazinyl, pyrimidinyl, quinolyl, phtalazinyl, naphthyridinyl, quinoxalinyl, quinazolyl, imidazopyridyl, oxazolopyridyl, thiazolopyridyl, imidazopyridazinyl, oxazolopyridazinyl, thiazolopyridazinyl, cynnolyl, pteridinyl, furazanyl, benzotriazolyl, pyrazolopyridinyl and purinyl.

In this specification, unless stated otherwise, the term "alkylaryl", "alkylheteroaryl" and "alkylcycloalkyl" refers respectively to a substituent that is attached via the alkyl radical to an aryl, heteroaryl or cycloalkyl radical, respectively. The term "$(C_1-C_6)$alkylaryl" includes aryl-$C_1-C_6$-alkyl radicals such as benzyl, 1-phenylethyl, 2-phenylethyl, 1-phenylpropyl, 2-phenylpropyl, 3-phenylpropyl, 1-naphthylmethyl and 2-naphthylmethyl. The term "$(C_1-C_6)$alkyheteroaryl" includes heteroaryl-$C_1-C_6$-alkyl radicals, wherein examples of heteroaryl are the same as those illustrated in the above definition, such as 2-furylmethyl, 3-furylmethyl, 2-thienylmethyl, 3-thienylmethyl, 1-imidazolylmethyl, 2-imidazolylmethyl, 3-imidazolylmethyl, 2-oxazolylmethyl, 3-oxazolylmethyl, 2-thiazolylmethyl, 3-thiazolylmethyl, 2-pyridylmethyl, 3-pyridylmethyl, 4-pyridylmethyl, 1-quinolylmethyl or the like.

In this specification, unless stated otherwise, the term "heterocycle" refers to an optionally substituted, monocyclic or bicyclic saturated, partially saturated or unsaturated ring system containing at least one heteroatom selected independently from N, O and S.

In this specification, unless stated otherwise, a 5- or 6-membered ring containing one or more atoms independently selected from C, N, O and S, includes aromatic and heteroaromatic rings as well as carbocyclic and heterocyclic rings which may be saturated or unsaturated. Examples of such rings may be, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, tetrahydrothiopyranyl, oxazolidinonyl, thiomorpholinyl, oxadiazolyl, thiadiazolyl, tetrazolyl, phenyl, cyclohexyl, cyclopentyl, cyclohexenyl and cyclopentenyl.

In this specification, unless stated otherwise, a 3- to 10-membered ring containing one or more atoms independently selected from C, N, O and S, includes aromatic and heteroaromatic rings as well as carbocyclic and heterocyclic rings which may be saturated or unsaturated. Examples of such rings may be, but are not limited to imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, tetrahydrothiopyranyl, furyl, pyrrolyl, isoxazolyl, isothiazolyl, oxazolyl, oxazolidinonyl, pyrazinyl, pyrazolyl, pyridazinyl, pyridyl, pyrimidyl, pyrrolyl, thiazolyl, thienyl, imidazolyl, triazolyl, phenyl, cyclopropyl, aziridinyl, cyclobutyl, azetidinyl, oxadiazolyl, thiadiazolyl, tetrazolyl, cyclopentyl, cyclopentenyl, cyclohexyl, cyclohexenyl, cycloheptyl, cycloheptenyl, cyclooctyl and cyclooctenyl.

In this specification, unless stated otherwise, the term "halo" or "halogen" may be fluoro, chloro, bromo or iodo.

In this specification, unless stated otherwise, the term "alkylhalo" means an alkyl radical as defined above, substituted with one or more halo radicals. The term "$(C_1-C_6)$alkylhalo" may include, but is not limited to, fluoromethyl, difluoromethyl, trifluoromethyl, fluoroethyl and difluoroethyl. The term "O—$C_1-C_6$-alkylhalo" may include, but is not limited to, fluoromethoxy, difluoromethoxy, trifluoromethoxy and fluoroethoxy.

In this specification, unless stated otherwise, the term "alkylcyano" means an alkyl radical as defined above, substituted with one or more cyano.

In this specification, unless stated otherwise, the term "optionally substituted" refers to radicals further bearing one or more substituents which may be, but are not limited to, $(C_1-C_6)$alkyl, hydroxy, $(C_1-C_6)$alkyloxy, mercapto, aryl, heterocycle, halogen, trifluoromethyl, pentafluoroethyl, cyano, cyanomethyl, nitro, amino, amido, amidinyl, carboxyl, carboxamide, $(C_1-C_6)$alkyloxycarbonyl, carbamate, sulfonamide, ester and sulfonyl.

In this specification, unless stated otherwise, the term "solvate" refers to a complex of variable stoichiometry formed by a solute (e.g. a compound of Formula (I)) and a solvent. The solvent is a pharmaceutically acceptable solvent as preferably water; such solvent may not interfere with the biological activity of the solute.

In this specification, unless stated otherwise, the term "positive allosteric modulator of mGluR4" or "allosteric modulator of mGluR4" refers also to a pharmaceutically acceptable acid or base addition salt thereof, a stereochemically isomeric form thereof and an N-oxide form thereof.

Pharmaceutical Compositions

Allosteric modulators of mGluR4 described herein, and the pharmaceutically acceptable salts, solvates and hydrates thereof can be used in pharmaceutical preparations in combination with a pharmaceutically acceptable carrier or diluent. Suitable pharmaceutically acceptable carriers include inert solid fillers or diluents and sterile aqueous or organic solutions. The allosteric modulators of mGluR4 will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

The amount of allosteric modulators of mGluR4, administered to the subject will depend on the type and severity of the disease or condition and on the characteristics of the subject, such as general health, age, sex, body weight and tolerance to drugs. The skilled artisan will be able to determine appropriate dosages depending on these and other factors. Effective dosages for commonly used CNS drugs are well known to the skilled person. The total daily dose usually ranges from about 0.05-2000 mg.

The present invention relates to pharmaceutical compositions which provide from about 0.01 to 1000 mg of the active ingredient per unit dose. The compositions may be administered by any suitable route. For example orally in the form of capsules, etc. . . . , parenterally in the form of solutions for injection, topically in the form of onguents or lotions, ocularly in the form of eye-drops, rectally in the form of suppositories, intranasally or transcutaneously in the form of delivery system like patches.

For oral administration, the allosteric modulators of mGluR4 thereof can be combined with a suitable solid or liquid carrier or diluent to form capsules, tablets, pills, powders, syrups, solutions, suspensions and the like.

The tablets, pills, capsules, and the like contain from about 0.01 to about 99 weight percent of the active ingredient and a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

For parenteral administration the disclosed allosteric modulators of mGluR4 can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

Preferably disclosed allosteric modulators of mGluR4 or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient in a unit dose of composition is an effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

Methods of Synthesis

The compounds according to the invention, in particular the compounds according to the Formula (I) to (III-B), may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (Green T. W. and Wuts P. G. M. (1991) *Protecting Groups in Organic Synthesis*, John Wiley & Sons). These groups are removed at a convenient stage of the compound synthesis using methods that are readily apparent to those skilled in the art. The selection of process as well as the reaction conditions and order of their execution shall be consistent with the preparation of compounds of Formula (I) to (III-B).

The compounds according to the invention may be represented as a mixture of enantiomers, which may be resolved into the individual pure R- or S-enantiomers. If for instance, a particular enantiomer is required, it may be prepared by asymmetric synthesis or by derivation with a chiral auxiliary, where the resulting diastereomeric mixture is separated and the auxiliary group cleaved to provide the pure desired enantiomers. Alternatively, where the molecule contains a basic functional group such as an amino or an acidic functional group such as carboxyl, this resolution may be conveniently performed by fractional crystallization from various solvents as the salts of an optical active acid or by other methods known in the literature (e.g. chiral column chromatography).

Resolution of the final product, an intermediate or a starting material may be performed by any suitable method known in the art (Eliel E. L., Wilen S. H. and Mander L. N. (1984) *Stereochemistry of Organic Compounds*, Wiley-Interscience).

Many of the heterocyclic compounds of the invention can be prepared using synthetic routes well known in the art (Katrizky A. R. and. Rees C. W. (1984) *Comprehensive Heterocyclic Chemistry*, Pergamon Press).

The product from the reaction can be isolated and purified employing standard techniques, such as extraction, chromatography, crystallization and distillation.

The compounds of the invention may be prepared by general route of synthesis as disclosed in the following methods.

In one embodiment of the present invention compounds of Formula (III-A) may be prepared according to the synthetic sequences illustrated in Scheme 1. Pyrazole g1 can be protected (PG: protecting group), for example, by p-methoxybenzyl or tert-butyloxycarbonyl using standard conditions. Then amidine can be synthesized either from ester treated with aluminium chloride in the presence of ammonium chloride or from nitrile by synthesis of amidoxime g3 followed by hydrogenation, in the presence of Pd/C and anhydride acetic. Under these conditions of reduction, the protecting group tert-butyloxycarbonyl is removed. The subsequent cyclization reaction between amidine g4 and isothiocyanate g5 may be promoted by di-tert-butylazodicarboxylate and a base such as DBU. Finally, aminothiadiazole g6 can be deprotected when PG is p-methoxybenzyl in the presence of TFA with a solvent such as dichloroethane under reflux.

Scheme 1

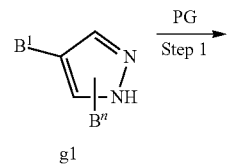

-continued

If B¹ = CO₂R, Step 2, Method A

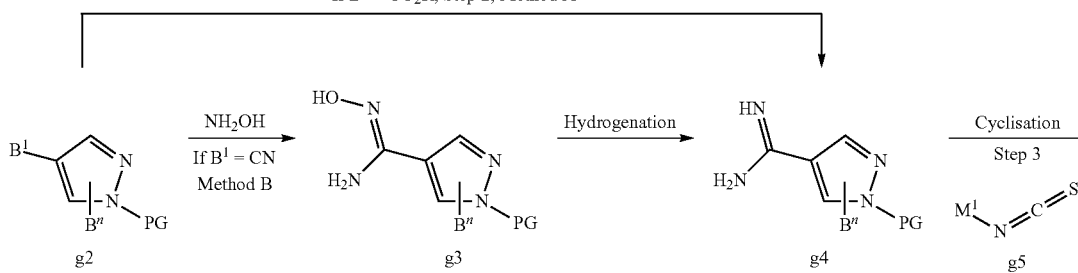

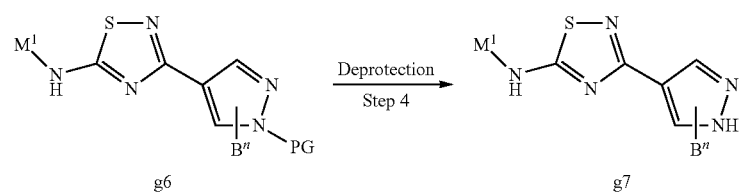

In another embodiment of the present invention, the compounds of Formula (III-B) may be prepared according to the synthetic sequences illustrated in Scheme 2. Compound g8 may be hydrolyzed by standard procedures followed by reaction with oxalyl chloride to yield compound g10. Subsequently, the acid chloride can be transformed in bromoketone g11 via the formation of diazoketone. Thiourea g12 can be generated either from a primary amine treated first with benzoylisothiocyanate followed by basic treatment (Press et al (2005) Bioorg. Med. Chem. Let. 15: 3081-3085) or via primary amine treated with thiocarbonyldiimidazole to form the isothiocyanate which is converted into thiourea by treatment with ammonia (WO2005/007601). Then the cyclization reaction may be performed between thiourea g12 and bromoketone g11 to yield the aminothiazole g13. Finally, if B¹ is a protecting group (PG), g13 can be deprotected with classical conditions.

Scheme 2

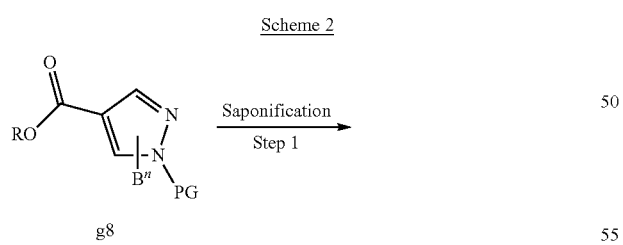

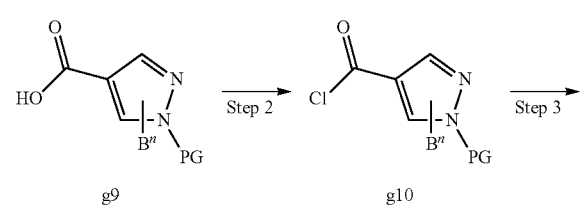

-continued

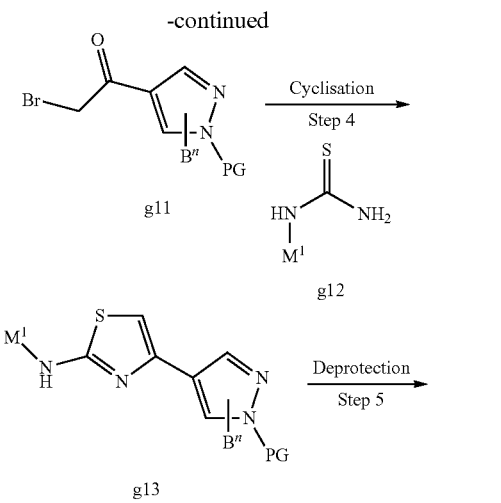

In one embodiment of the present invention, the compounds of Formula (III-B) may be prepared according to the synthetic sequences illustrated in Scheme 3. Compound g9 may be converted into Weinreb amide g15 which undergoes addition of Grignard reagent to yield ketone g16. Subsequently ketone g16 can be transformed into bromoketone g17 in presence of CuBr₂. Then the cyclization reaction may be performed between bromoketone g17 and thiourea 12 to yield the aminothiazole g18. Finally, g20 can be deprotected with classical conditions.

Scheme 3

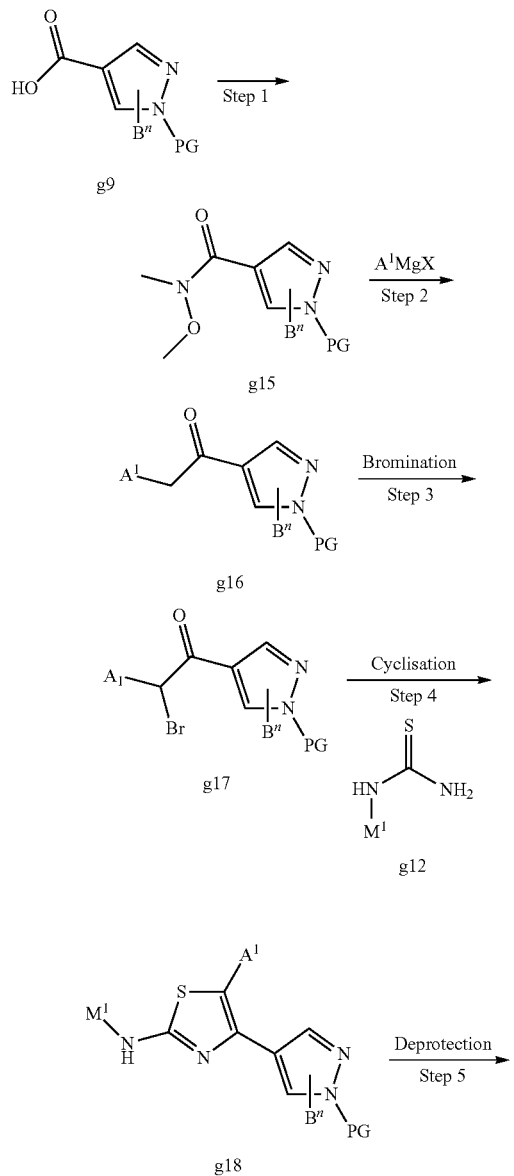

Scheme 4

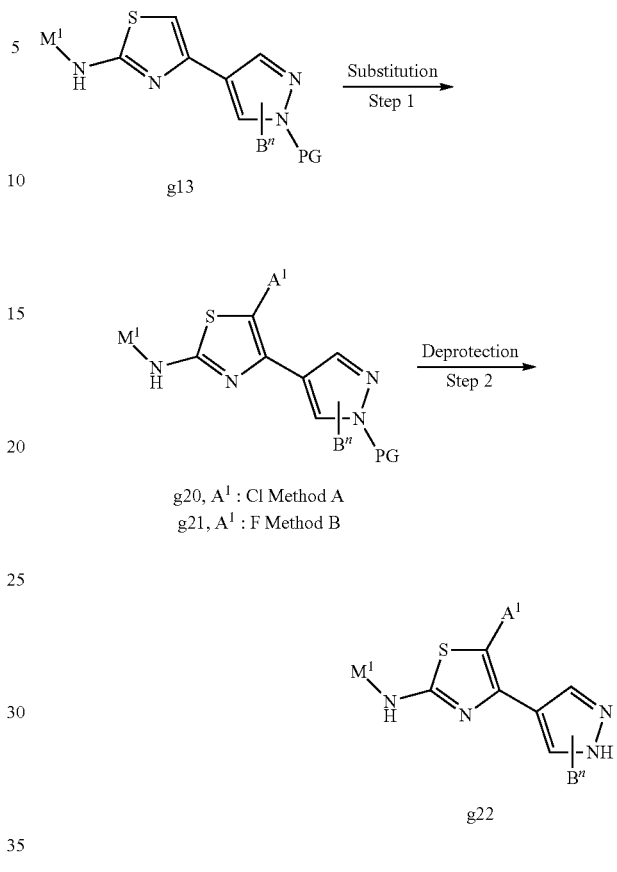

In another embodiment of the present invention compounds of Formula (III-B) may be prepared in accordance with Scheme 4. Thiazole ring in compound g13 can be substituted either by chloride in the presence of N-chlorosuccinimide or by fluoride using Select-Fluor. Then compound g22 can be obtained after deprotection in the presence of TFA using thermic or microwave conditions.

In another embodiment of the present invention compounds of Formula (III-B) may be prepared in accordance with Scheme 5. Bromoketone g11 can be converted into cyanoketone g23 in the presence of KCN. Then the cyclization reaction may be performed between cyanoketone g23 and thiourea g12 to yield the aminothiazole g24. Finally, g24 can be deprotected with classical conditions well known to people skilled in the art.

Scheme 5

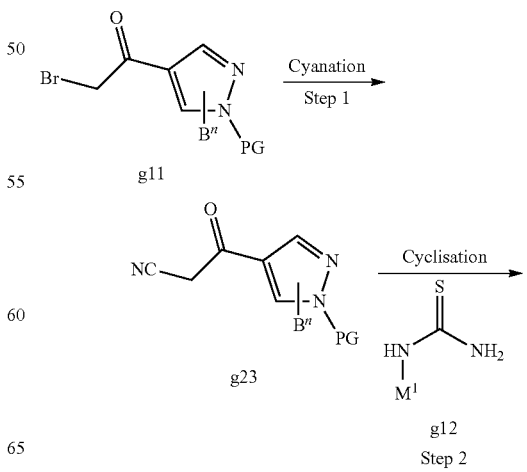

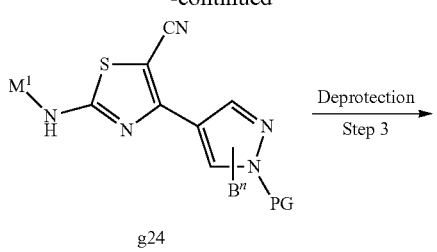

g24

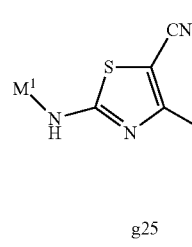

g25

In another embodiment of the present invention compounds of Formula (III-B) may be prepared in accordance with Scheme 6. After protection with p-methoxybenzyl using standard conditions, pyrazole g27 undergoes coupling with enolether g28 in the presence of Pd(OAc)$_2$ and silver carbonate. The subsequent ketone g29 in the presence of thiourea g12 may be cyclized into thiazole g30 which can be deprotected with classical conditions.

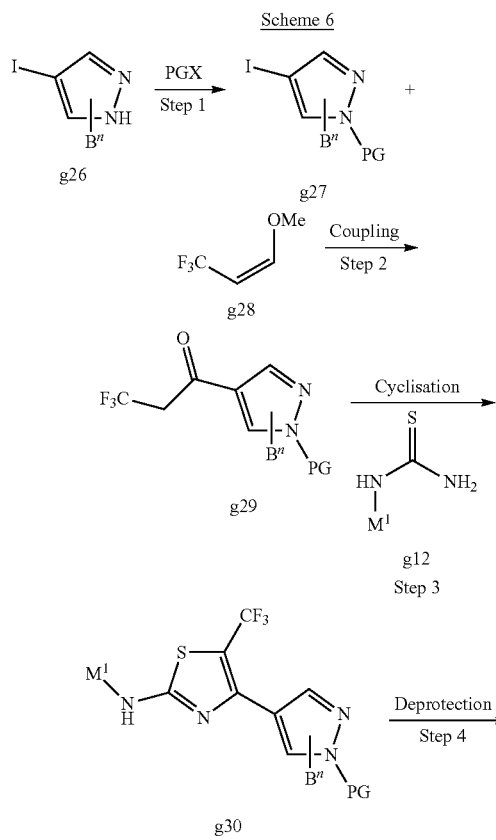

Scheme 6

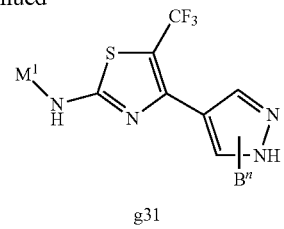

g31

In another embodiment of the present invention compounds of Formula (III-B) may be prepared in accordance with Scheme 7. After Sonogashira coupling between alkyne g32 and iodopyrazole g27, triple bond in compound g33 is transformed into methyl ketone in the presence of SnCl$_2$. The subsequent ketone g34 is first brominated and then cyclised in the presence of thiourea g12 into thiazole g36.

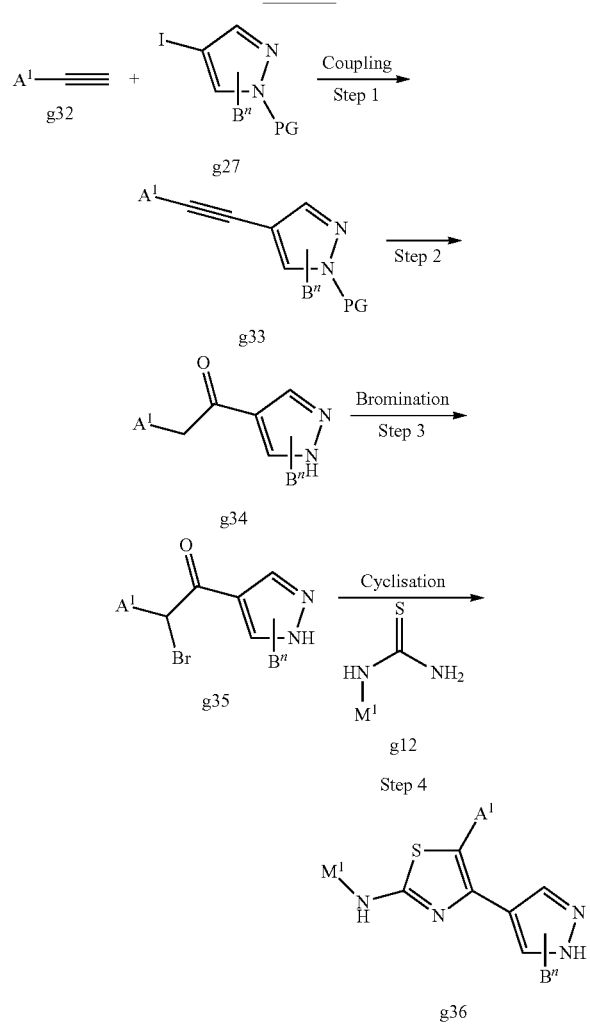

Scheme 7

In another embodiment of the present invention compounds of Formula (III-B) may be prepared in accordance with Scheme 8. Methyl alcohol can be introduced on the thiazole ring from compound g14 using formaldehyde in the presence of a base such as Et$_3$N under microwaved conditions as described in WO2007/031440A2.

Scheme 8

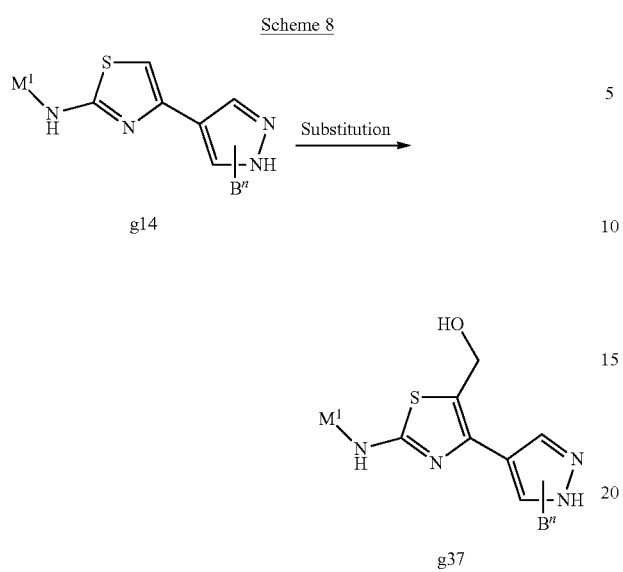

In another embodiment of the present invention compounds of Formula (III-B) may be prepared in accordance with Scheme 9. A well known procedure to synthetise pyrazole is from ketoester g38 which is condensed with 1,1-dimethoxy-N,N-dimethylmethanamine followed by cyclisation in the presence of hydrazine. Pyrazole g40 can be protected by p-methoxybenzyl using standard conditions. Then compound g41 may be hydrolyzed by standard procedures followed by reaction with oxalyl chloride to yield compound g43. Subsequently, the acid chloride can be transformed in bromoketone g44 via the formation of diazoketone. Then the cyclization reaction may be performed between thiourea g12 and bromoketone g44 to yield aminothiazole g45. Finally, g45 can be deprotected with classical conditions.

Scheme 9

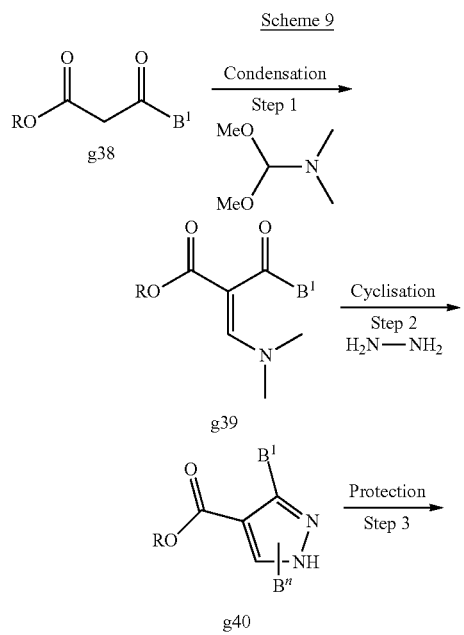

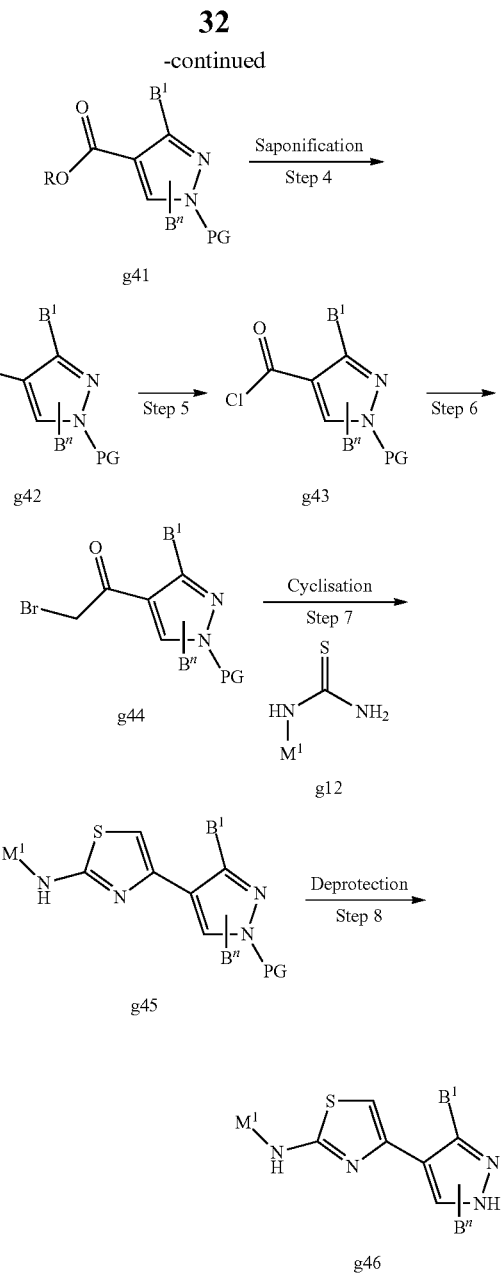

In one embodiment of the present invention compounds of Formula (III) may be prepared according to Scheme 10. g47 may be acylated in the presence of anhydride acetic in a solvent such as pyridine or with an acid chloride in the presence of a base such as $Et_3N$ in a solvent such as THF.

Scheme 10

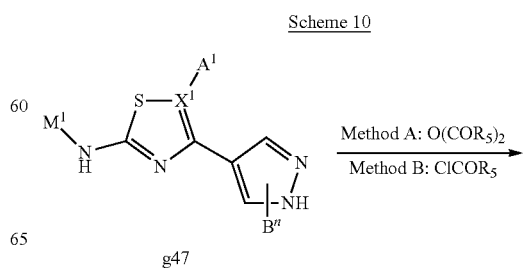

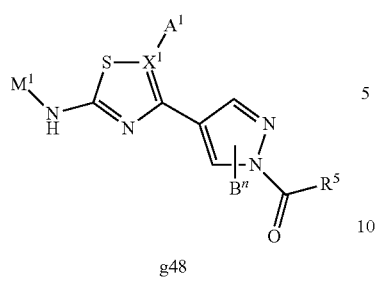

g48

In one embodiment of the present invention compounds of Formula (III) may be prepared according to Scheme 11. g47 may be converted into urea by treatment either with potassium cyanate as described in Yang et al (2004) J. Med. Chem. 47 (6): 1547-1552, or with carbamic chloride in the presence of a base such as DBU or with isocyanate.

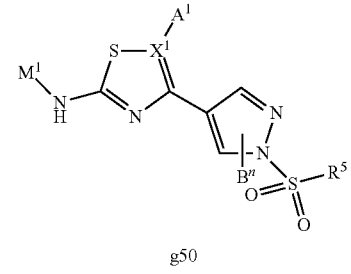

g50

In another embodiment of the present invention compounds of Formula (II) may be prepared in accordance with Scheme 13. Pyrazole g51 can be protected by p-methoxybenzyl using standard conditions. Then compound g53 may be coupled to 2,6-dibromopyridine via Suzuki coupling followed by nucleophilic substitution of primary amine in presence of a base such as KOtBu. Finally, g55 can be deprotected with classical conditions.

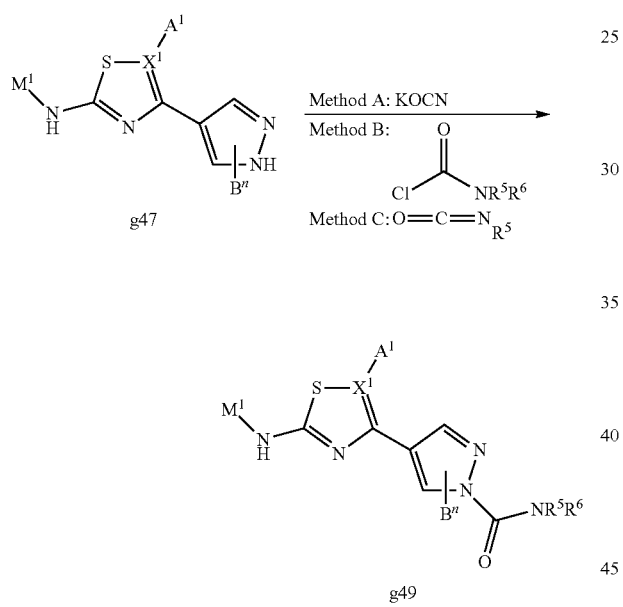

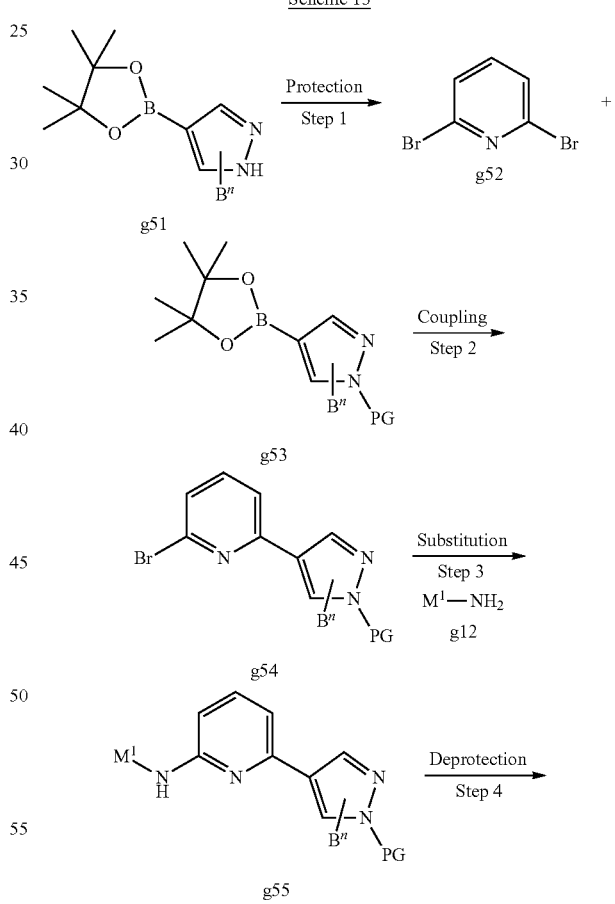

In one embodiment of the present invention compounds of Formula (III) may be prepared according to Scheme 12. g47 may be sulfonylated by sulfonyl chloride in the presence of a base such as Et$_3$N to yield pyrazole g50.

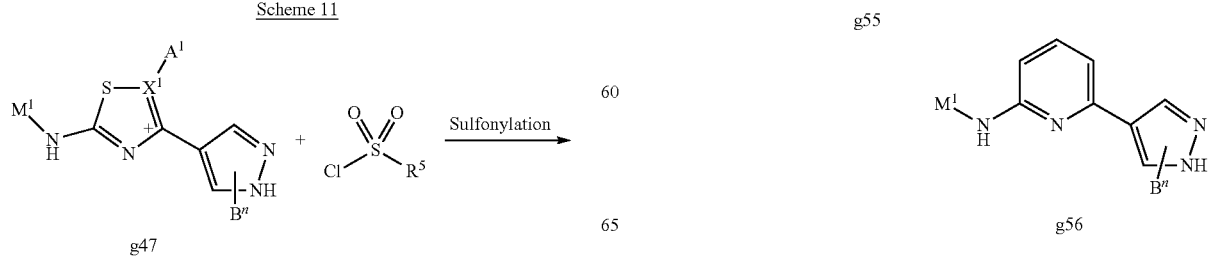

EXPERIMENTAL

Unless otherwise noted, all starting materials were obtained from commercial suppliers and used without further purification.

Specifically, the following abbreviations may be used in the examples and throughout the specification.

| | |
|---|---|
| ACN (Acetonitrile) | mg (Milligrams) |
| AcOEt (Ethyl acetate) | MgSO$_4$ (Magnesium sulphate) |
| (Boc)$_2$O (Di-tert-butyl carbonate) | μL (Microliters) |
| CuBr$_2$ (Copper (II) bromide) | mL (Milliliters) |
| CuI (Copper (I) iodide) | mmol (Millimoles) |
| DBU (1,8-Diazabicyclo[5.4.0]undec-7-ene) | M.p. (Melting point) |
| | NaCl (Sodium chloride) |
| DCM (Dichloromethane) | NaHCO$_3$ (Sodium hydrogenocarbonate) |
| DIEA (Diisopropyl ethyl amine) | |
| DMAP (N,N-Dimethylaminopyridine) | NaOH (Sodium hydroxide) |
| | Na$_2$CO$_3$ (Sodium carbonate) |
| DME (Dimethoxyethane) | Na$_2$SO$_4$ (Sodium sulphate) |
| DMF (Dimethylformamide) | NH$_4$OH (Ammonium hydroxide) |
| EtOH (Ethanol) | Pd/C (Palladium on charcoal) |
| Et$_2$O (Diethyl ether) | PdCl$_2$(PPh$_3$)$_2$ (Bis(triphenylphosphine) palladium (II) dichloride |
| Et$_3$N (Triethyl amine) | |
| HBr (Hydrobromic acid) | |
| HCl (Hydrochloric acid) | Pd(OAc)$_2$ (Palladium(II)acetate) |
| KCN (Potassium cyanide) | Pd(PPh$_3$)$_4$ (Tetrakis(triphenyl-phosphine)palladium(0)) |
| KOtBu (Potassium-tert-butoxide) | |
| K$_2$CO$_3$ (Potassium carbonate) | |
| K$_3$PO$_4$ (Potassium phosphate) | PPh$_3$ (Triphenylphosphine) |
| LCMS (Liquid Chromatography Mass Spectrum) | SnCl$_2$ (Tin chloride) |
| | TFA (Trifluoroacetic acid) |
| LiOH (Lithium hydroxide) | THF (Tetrahydrofuran) |
| M (Molar) | TLC (Thin layer chromatography) |
| MeOH (Methanol) | TMSdiazomethane (Trimethylsilyldiazomethane) |
| | RT (Retention Time) |

All references to brine refer to a saturated aqueous solution of NaCl. Unless otherwise indicated, all temperatures are expressed in ° C. (degrees Centigrade). All reactions are conducted not under an inert atmosphere at room temperature unless otherwise noted.

Most of the reaction were monitored by thin-layer chromatography on 0.25 mm Merck silica gel plates (60E-254), visualized with UV light. Flash column chromatography was performed on prepacked silica gel cartridges (15-40 μM, Merck).

Melting point determination was performed on a Buchi B-540 apparatus.

EXAMPLES

Example 1

N-(2-Chlorophenyl)-3-(3-methyl-1H-pyrazol-4-yl)-1,2,4-thiadiazol-5-amine (Final Compound 1-3)

tert-Butyl 4-cyano-3-methyl-1H-pyrazole-1-carboxylate

According to Scheme 1 Step 1: To a solution of 3-methyl-1H-pyrazol-4-carbonitrile (9.34 mmol, 1.00 g) in DCM (20 mL) were sequentially added DIEA (9.34 mmol, 1.60 mL), (Boc)$_2$O (9.34 mmol, 2.04 g) and DMAP (0.93 mmol, 0.11 g). After stirring for 14 hours at room temperature, the reaction mixture was quenched with water. The aqueous phase was extracted with DCM. The organic phase was washed with a saturated solution of NaHCO$_3$ and brine, was dried over MgSO$_4$, was filtered and was concentrated under reduced pressure. The crude product was purified by flash chromatography over silica gel using cyclohexane/AcOEt (85:15) as eluent to afford tert-butyl 4-cyano-3-methyl-1H-pyrazole-1-carboxylate (7.96 mmol, 1.65 g, 85%) as a white solid.

LC (Zorbax SB-C$_{18}$, 3.5 μm, 4.6×50 mm Column): RT=3.72 min; MS m/z ES$^+$=108 (M$^+$-Boc).

3-Methyl-1H-pyrazole-4-carboxamidine acetate

According to Scheme 1 Step 2, Method B: A mixture of tert-butyl 4-cyano-3-methyl-1H-pyrazole-1-carboxylate (7.96 mmol, 1.65 g) and hydroxylamine 50% in water (15.9 mmol, 0.98 mL) and EtOH (20 mL) was heated at 80° C. for 4 hours. After evaporation of the solvent, 1.90 g (7.91 mmol, 99%) of tert-butyl-4-(M-hydroxycarbamimidoyl)-3-methyl-1H-pyrazole-1-carboxylate was obtained. The crude product was used in the next step without purification.

LC (Zorbax SB-C$_{18}$, 3.5 μm, 4.6×30 mm Column): RT=0.59 min; MS m/z ES$^+$=141 (M$^+$-Boc).

A mixture of tert-butyl-4-(N'-hydroxycarbamimidoyl)-3-methyl-1H-pyrazole-1-carboxylate (7.91 mmol, 1.90 g), Pd/C (190 mg) and anhydride acetic (7.91 mmol, 0.81 g) in MeOH (50 mL) was stirred at room temperature for 6 hours under hydrogen atmosphere. After filtration and evaporation of the solvent, the crude product was triturated with Et$_2$O and dried to yield 3-methyl-1H-pyrazole-4-carboxamidine acetate (1.21 g, 6.57 mmol, 83%) as a white solid.

LC (Zorbax SB-C$_{18}$, 3.5 μm, 4.6×30 mm Column): RT=0.23 min; MS m/z ES$^+$=126.

N-(2-Chorophenyl)-3-(3-methyl-1H-pyrazol-4-yl)-1,2,4-thiadiazol-5-amine

According to Scheme 1 Step 3: DBU (0.26 mmol, 0.04 mL) was added to a solution of 1-chloro-2-isothiocyanatobenzene (0.26 mmol, 34 μl) and 3-methyl-1H-pyrazole-4-carboxamidine acetate (0.26 mmol, 60 mg) in DMF (5 mL) under nitrogen. The reaction mixture was stirred at room temperature until total consumption of the amidine. Then, di-tert-butylazodicarboxylate (0.26 mmol, 60 mg) was added dropwise and the reaction mixture was stirred for 5 minutes. Then a solution of NaOH 3M (3 mL) was added. The reaction mixture was stirred at room temperature for 1 hour. After evaporation of the EtOH, water was added and the aqueous phase was extracted with AcOEt. The organic phase was washed with a solution of HCl 1 M, water and brine, was dried over Na$_2$SO$_4$, was filtered and was concentrated under reduced pressure. Sodium methylate (2.60 mmol, 140 mg) was added to the crude product dissolved in MeOH and the reaction mixture was heated at 70° C. for 2 hours (cleavage of N-(2-chlorophenyl)-4-(5-(3-fluorophenylamino)-1,2,4-thiadiazol-3-yl)-3-methyl-1H-pyrazole-1-carbothioamide obtained from the addition of the isothiocyanate on the pyrazole ring). Water was added dropwise and the compound was extracted with AcOEt. The organic phase was washed with water and brine, was dried over Na$_2$SO$_4$, was filtered and was concentrated under reduced pressure. The crude product was purified by flash chromatography over silica gel using cyclohexane/AcOEt (50:50) as eluent to afford N-(2-chlorophenyl)-3-(3-methyl-1H-pyrazol-4-yl)-1,2,4-thiadiazol-5-amine (51 μmol, 15 mg, 20%) as a white solid.

M.p.: 180-182° C.;

LC (Zorbax SB-C$_{18}$, 3.5 μm, 4.6×30 mm Column): RT=2.18 min; MS m/z ES$^+$=292;

$^1$H NMR (300 MHz, DMSO) 12.95-12.70 (1H, br s), 10.45 (1H, s), 8.50 (1H, d), 8.10-7.80 (1H, m), 7.55 (1H, d), 7.50-7.38 (1H, m), 7.22-7.10 (1H, m), 2.61 (3H, s).

Example 2

3-(3-Propyl-1H-pyrazol-4-yl)-N-(pyridin-2-yl)-1,2,4-thiadiazol-5-amine (Final Compound 1-9)

Ethyl 1-(4-methoxybenzyl)-3-propyl-1H-pyrazole-4-carboxylate and ethyl 1-(4-methoxybenzyl)-5-propyl-1H-pyrazole-4-carboxylate According to Scheme 1 Step 1: A suspension of ethyl 5-propyl-1H-pyrazole-4-carboxylate (2.74 mmol, 500 mg), 1-(bromomethyl)-4-methoxybenzene (2.74 mmol, 0.39 mL) and $K_2CO_3$ (2.74 mmol, 379 mg) in acetonitrile (10 mL) was heated at 70° C. overnight. Water was added and the aqueous phase was extracted with AcOEt. The organic phase was washed with water and brine, was dried over $Na_2SO_4$, was filtered and was concentrated under reduced pressure. The crude product was purified by flash chromatography over silica gel using cyclohexane/AcOEt (80:20) as eluent to afford a mixture of ethyl 1-(4-methoxybenzyl)-3-propyl-1H-pyrazole-4-carboxylate and of ethyl 1-(4-methoxybenzyl)-5-propyl-1H-pyrazole-4-carboxylate (2.15 mmol, 650 mg, 78%) as an orange oil.

LC (Zorbax SB-$C_{18}$, 3.5 µm, 4.6×30 mm Column): RT=2.77 min; MS m/z ES$^+$=303.

1-(4-Methoxybenzyl)-3-propyl-1H-pyrazole-4-carboximidamide and 1-(4-methoxybenzyl)-5-propyl-1H-pyrazole-4-carboximidamide According to Scheme 1 Step 2, Method A: Trimethylaluminium, 2M solution in heptane (13.2 mmol, 6.61 mL), was added dropwise to a suspension of ammonium chloride (13.2 mmol, 708 mg) in dry toluene (20 mL), under an argon atmosphere, at 0° C. The reaction mixture was stirred at room temperature until no more evolution of gas was observed. After addition of a mixture of ethyl 1-(4-methoxybenzyl)-3-propyl-1H-pyrazole-4-carboxylate and of 1-(4-methoxybenzyl)-5-propyl-1H-pyrazole-4-carboxylate (1.32 mmol, 400 mg), the reaction mixture was stirred at 80° C. overnight. The reaction mixture was then cooled down to 0° C. and MeOH was added with consequent stirring for 1 hour at room temperature. The reaction mixture was added to a mixture of DCM and silica, then filtered on an empty cartridge. The cartridge was first eluted with DCM and then with DCM/MeOH (80:20) as eluent. After filtration and evaporation, a mixture of 1-(4-methoxybenzyl)-3-propyl-1H-pyrazole-4-carboximidamide and of 1-(4-methoxybenzyl)-5-propyl-1H-pyrazole-4-carboximidamide (0.57 mmol, 175 mg, 49%) was obtained as a white solid.

LC (Zorbax SB-$C_{18}$, 3.5 µm, 4.6×30 mm Column): RT=1.38 min; MS m/z ES$^+$=273.

3-(1-(4-Methoxybenzyl)-3-propyl-1H-pyrazol-4-yl)-N-(pyridin-2-yl)-1,2,4-thiadiazol-5-amine and 3-(1-(4-methoxybenzyl)-5-propyl-1H-pyrazol-4-yl)-N-(pyridin-2-yl)-1,2,4-thiadiazol-5-amine According to Scheme 1 Step 3: DBU (567 µmol, 86.3 mg) was added to a solution of a mixture of 1-(4-methoxybenzyl)-3-propyl-1H-pyrazole-4-carboximidamide and of 1-(4-methoxybenzyl)-5-propyl-1H-pyrazole-4-carboximidamide (567 µmol, 175 mg), and isothiocyanatobenzene (567 µmol, 76.6 mg) in dry DMF, under argon. The reaction mixture was stirred at room temperature until total consumption of the amidine. Then, di-tert-butylazodicarboxylate (567 µmol, 130 mg) was added dropwise and was stirred for 5 minutes. The reaction mixture was quenched with water and was extracted with AcOEt. The organic phase was washed with brine, was dried over $Na_2SO_4$, was filtered and was concentrated under reduced pressure. The crude product was purified by flash chromatography over silica gel using cyclohexane/AcOEt (70:30) as eluent to afford a mixture of 3-(1-(4-methoxybenzyl)-3-propyl-1H-pyrazol-4-yl)-N-(pyridin-2-yl)-1,2,4-thiadiazol-5-amine and of 3-(1-(4-methoxybenzyl)-5-propyl-1H-pyrazol-4-yl)-N-(pyridin-2-yl)-1,2,4-thiadiazol-5-amine (0.47 mmol, 190 mg, 83%) as an orange oil.

LC (Zorbax SB-$C_{18}$, 3.5 µm, 4.6×30 mm Column): RT=3.05 min; MS m/z ES$^+$=406.

3-(3-Propyl-1H-pyrazol-4-yl)-N-(pyridin-2-yl)-1,2,4-thiadiazol-5-amine

According to Scheme 1 Step 4: A solution of a mixture of 3-(1-(4-methoxybenzyl)-3-propyl-1H-pyrazol-4-yl)-N-(pyridin-2-yl)-1,2,4-thiadiazol-5-amine and of 3-(1-(4-methoxybenzyl)-5-propyl-1H-pyrazol-4-yl)-N-(pyridin-2-yl)-1,2,4-thiadiazol-5-amine (0.39 mmol, 160 mg) in TFA (2 mL) and dichloroethane (2 mL) was stirred under reflux for 12 hours. After evaporation of the solvent, DCM was added and the organic phase was washed with a saturated solution of $NH_4OH$ and brine. Then the organic phase was dried over $Na_2SO_4$, was filtered and was concentrated under reduced pressure. The resulting crude product was purified by flash chromatography over silica gel using DCM/MeOH (95:5) as eluent to yield 3-(3-propyl-1H-pyrazol-4-yl)-N-(pyridin-2-yl)-1,2,4-thiadiazol-5-amine (0.24 mmol, 70 mg, 62%) as a white solid.

M.p.: 248-250° C.;

LC (Zorbax SB-$C_{18}$, 3.5 µm, 4.6×30 mm Column): RT=2.15 min; MS m/z ES$^+$=287;

$^1$H NMR (300 MHz, DMSO) 12.95-12.65 (1H, br s), 12.15 (1H, s), 8.42 (1H, d), 8.10-7.75 (2H, m), 7.18 (1H, d), 7.12-7.00 (1H, m), 3.12-2.90 (2H, m), 1.80-1.60 (2H, m), 0.95 (3H, t).

Example 3

3-(3-Methyl-1H-pyrazol-4-yl)-N-(pyridin-2-yl)-1,2,4-thiadiazol-5-amine (Final Compound 1-5)

1-(4-Methoxybenzyl)-3-methyl-1H-pyrazol-4-carbonitrile and 1-(4-methoxybenzyl)-5-methyl-1H-pyrazol-4-carbonitrile According to Scheme 1 Step 1: Triphenylphosphine (11 mmol, 2.9 g), (4-methoxyphenyl)methanol (10 mmol, 1.4 g) and di-tert-butylazodicarboxylate (11 mmol, 2.6 g) were added to a solution of 3-methyl-1H-pyrazol-4-carbonitrile (9.3 mmol, 1.0 g), in DCM (40 mL) at 0° C. The reaction mixture was stirred at room temperature overnight. The organic phase was washed with a saturated solution of $NH_4OH$ and brine. Then the organic phase was dried over $MgSO_4$, was filtered and was concentrated under reduced pressure. The resulting crude product was purified by flash chromatography over silica gel using cyclohexane/AcOEt (90:10) as eluent to yield a mixture of 1-(4-methoxybenzyl)-3-methyl-1H-pyrazol-4-carbonitrile and of 1-(4-methoxybenzyl)-5-methyl-1H-pyrazol-4-carbonitrile (9.3 mmol, 2.1 g, 100%).

1-(4-Methoxybenzyl)-3-methyl-1H-pyrazole-4-carboximidamide and 1-(4-methoxybenzyl)-5-methyl-1H-pyrazole-4-carboximidamide According to Scheme 1 Step 2: The compound was prepared according to Example 1 Step 2, Method B from a mixture of 1-(4-methoxybenzyl)-3-methyl-1H-pyrazol-4-carbonitrile and of 1-(4-methoxybenzyl)-5-methyl-1H-pyrazol-4-carbonitrile (9.30 mmol, 2.1 g). Reaction conditions: 12 hours at 80° C. 2.42 g (9.30 mmol, 100%) of a mixture of (N'-hydroxy-1-(4-methoxybenzyl)-3-methyl-1H-pyrazole-4-carboximidamide and of (N'-hydroxy-1-(4-methoxybenzyl)-5-methyl-1H-pyrazole-4-carboximidamide were obtained. The crude product was used without purification.

LC (Zorbax SB-$C_{18}$, 3.5 μm, 4.6×30 mm Column): RT=0.86 min; MS m/z $ES^+$=261.

The title compound was prepared from a mixture of (N'-hydroxy-1-(4-methoxybenzyl)-3-methyl-1H-pyrazole-4-carboximidamide and of (N'-hydroxy-1-(4-methoxybenzyl)-5-methyl-1H-pyrazole-4-carboximidamide (9.30 mmol, 2.42 g). Reaction conditions: 12 hours at room temperature. 1.55 g (5.11 mmol, 55%) of a mixture of 1-(4-methoxybenzyl)-3-methyl-1H-pyrazole-4-carboximidamide and of 1-(4-methoxybenzyl)-5-methyl-1H-pyrazole-4-carboximidamide was obtained as a white solid. The crude product was used without purification.

LC (Zorbax SB-$C_{18}$, 3.5 μm, 4.6×30 mm Column): RT=0.91 min; MS m/z $ES^+$=245.

3-(1-(4-Methoxybenzyl)-3-methyl-1H-pyrazol-4-yl)-N-(pyridin-2-yl)-1,2,4-thiadiazol-5-amine and 3-(1-(4-methoxybenzyl)-5-methyl-1H-pyrazol-4-yl)-N-(pyridin-2-yl)-1,2,4-thiadiazol-5-amine According to Scheme 1 Step 3: The title compound was prepared according to Example Step 3, from a mixture of 1-(4-methoxybenzyl)-3-methyl-1H-pyrazole-4-carboximidamide and of 1-(4-methoxybenzyl)-5-methyl-1H-pyrazole-4-carboximidamide (0.30 mmol, 0.15 g). 40 mg (0.11 mmol, 36%) of 3-(1-(4-methoxybenzyl)-3-methyl-1H-pyrazol-4-yl)-N-(pyridin-2-yl)-1,2,4-thiadiazol-5-amine were obtained as a white solid. The crude product was used without purification.

LC (Zorbax SB-$C_{18}$, 3.5 μm, 4.6×30 mm Column): RT=2.50 min; MS m/z $ES^+$=379.

3-(3-Methyl-1H-pyrazol-4-yl)-N-(pyridin-2-yl)-1,2,4-thiadiazol-5-amine

According to Scheme 1 Step 4: The title compound was prepared according to Example 2 Step 4, from a mixture of 3-(1-(4-methoxybenzyl)-3-methyl-1H-pyrazol-4-yl)-N-(pyridin-2-yl)-1,2,4-thiadiazol-5-amine and of 1-(4-methoxybenzyl)-5-methyl-1H-pyrazole-4-carboximidamide (0.11 mmol, 43 mg). 11 mg (43 μmol, 37%) of 3-(3-methyl-1H-pyrazol-4-yl)-N-(pyridin-2-yl)-1,2,4-thiadiazol-5-amine were obtained as a white solid.

M.p.: >280° C.;
LC (Zorbax SB-$C_{18}$, 3.5 μm, 4.6×30 mm Column): RT=1.75 min; MS m/z $ES^+$=259;
$^1$H NMR (300 MHz, MeOD) 8.32 (1H, d), 7.92 (1H, s), 7.72-7.60 (1H, m), 7.02 (1H, d), 6.98-6.85 (1H, m), 2.55 (3H, s).

Example 4

N-(Pyridin-2-yl)-4-(3-(trifluoromethyl)-1H-pyrazol-4-yl)thiazol-2-amine (Final Compound 1-12)

1-(4-Methoxybenzyl)-5-(trifluoromethyl)-1H-pyrazole-4-carboxylic acid and 1-(4-methoxybenzyl)-3-(trifluoromethyl)-1H-pyrazole-4-carboxylic acid According to Scheme 2 Step 1: A solution of a mixture of ethyl 1-(4-methoxybenzyl)-5-(trifluoromethyl)-1H-pyrazole-4-carboxylate and of ethyl 1-(4-methoxybenzyl)-3-(trifluoromethyl)-1H-pyrazole-4-carboxylate (2.80 mmol, 0.92 g) and LiOH (28.0 mmol, 1.20 g) in water/THF (1:1, 20 mL) was heated at 80° C. overnight. After evaporation of the solvent, the aqueous phase was extracted with DCM then acidified with a solution of HCl 1 M until pH=1-2 and extracted with DCM. The organic phase was washed with brine, was dried over $Na_2SO_4$, was filtered and was concentrated under reduced pressure to yield a mixture of 1-(4-methoxybenzyl)-5-(trifluoromethyl)-1H-pyrazole-4-carboxylic acid and of 1-(4-methoxybenzyl)-3-(trifluoromethyl)-1H-pyrazole-4-carboxylic acid (2.33 mmol, 0.70 g, 83%) as a brown solid. The crude product was used without purification.

LC (Zorbax SB-$C_{18}$, 3.5 μm, 4.6×30 mm Column): RT=2.19 min.

1-(4-Methoxybenzyl)-5-(trifluoromethyl)-1H-pyrazole-4-carbonyl chloride and 1-(4-methoxybenzyl)-3-(trifluoromethyl)-1H-pyrazole-4-carbonyl chloride According to Scheme 2 Step 2: A solution of a mixture of 1-(4-methoxybenzyl)-5-(trifluoromethyl)-1H-pyrazole-4-carboxylic acid and of 1-(4-methoxybenzyl)-3-(trifluoromethyl)-1H-pyrazole-4-carboxylic acid (2.33 mmol, 0.70 g), oxalyl chloride (4.66 mmol, 0.41 mL) and three drops of DMF was stirred for 30 minutes at room temperature. After evaporation of the solvent, the crude residue was treated with toluene and was coevaporated to dryness to yield a mixture of 1-(4-methoxybenzyl)-5-(trifluoromethyl)-1H-pyrazole-4-carbonyl chloride and of 1-(4-methoxybenzyl)-3-(trifluoromethyl)-1H-pyrazole-4-carbonyl chloride (2.33 mmol, 0.74 g). The crude product was used without purification.

LC (Zorbax SB-$C_{18}$, 3.5 μm, 4.6×30 mm Column): RT=2.63 min.

2-Bromo-1-(1-(4-methoxybenzyl)-3-(trifluoromethyl)-1H-pyrazol-4-yl)ethanone and 2-bromo-1-(1-(4-methoxybenzyl)-5-(trifluoromethyl)-1H-pyrazol-4-yl)ethanone According to Scheme 2 Step 3: A solution of TMSdiazomethane (8.7 mmol, 4.3 mL) was added to a solution of a mixture of 1-(4-methoxybenzyl)-5-(trifluoromethyl)-1H-pyrazole-4-carbonyl chloride and of 1-(4-methoxybenzyl)-3-(trifluoromethyl)-1H-pyrazole-4-carbonyl chloride (2.33 mmol, 0.74 g) in acetonitrile (10 mL) at 0° C. The reaction mixture was stirred at room temperature overnight. HBr (9.9 mmol, 1.1 mL, 48%) was added at 0° C. to the reaction mixture. The reaction mixture was stirred at room temperature for one hour. After evaporation of the solvent, AcOEt was added and the aqueous phase was neutralized with a solution of NaOH 1 M. The aqueous phase was extracted with AcOEt. The organic phase was washed with brine, was dried over $Na_2SO_4$, was filtered and was concentrated under reduced pressure to yield a mixture of 2-bromo-1-(1-(4-methoxybenzyl)-3-(trifluoromethyl)-1H-pyrazol-4-yl)ethanone and of 2-bromo-1-(1-(4-methoxybenzyl)-5-(trifluoromethyl)-1H-pyrazol-4-yl)ethanone (2.33 mmol, 0.88 g, 100%) as a brown oil. The crude product was used without purification.

4-(1-(4-Methoxybenzyl)-3-(trifluoromethyl)-1H-pyrazol-4-yl)-N-(pyridin-2-yl)thiazol-2-amine and 4-(1-(4-methoxybenzyl)-5-(trifluoromethyl)-1H-pyrazol-4-yl)-N-(pyridin-2-yl)thiazol-2-amine According to Scheme 2 Step 4: A solution of a mixture of 2-bromo-1-(1-(4-methoxybenzyl)-3-(trifluoromethyl)-1H-pyrazol-4-yl)ethanone and of 2-bromo-1-(1-(4-methoxybenzyl)-5-(trifluoromethyl)-1H-pyrazol-4-yl)ethanone (0.95 mmol, 0.15 g) and of 1-(pyridin-2-yl)thiourea (1.19 mmol, 0.45 g) in acetone (15 mL) was stirred under reflux overnight. After filtration, the precipitate was washed with acetone and AcOEt and then dried to yield a mixture of 4-(1-(4-methoxybenzyl)-3-(trifluoromethyl)-1H-pyrazol-4-yl)-N-(pyridin-2-yl)thiazol-2-amine and of 4-(1-(4-methoxybenzyl)-5-(trifluoromethyl)-1H-pyrazol-4-yl)-N-(pyridin-2-yl)thiazol-2-amine (0.58 mmol, 0.25 g) as a white solid. The crude product was used without purification.

LC (Zorbax SB-$C_{18}$, 3.5 µm, 4.6×30 mm Column): RT=2.92 min; MS m/z $ES^+$=432.

N-(Pyridin-2-yl)-4-(3-(trifluoromethyl)-1H-pyrazol-4-yl)thiazol-2-amine

According to Scheme 2 Step 5: A solution of a mixture of 4-(1-(4-methoxybenzyl)-3-(trifluoromethyl)-1H-pyrazol-4-yl)-N-(pyridin-2-yl)thiazol-2-amine and of 4-(1-(4-methoxybenzyl)-5-(trifluoromethyl)-1H-pyrazol-4-yl)-N-(pyridin-2-yl)thiazol-2-amine (0.58 mmol, 0.25 g) in TFA (3 mL) was stirred under reflux for 12 hours (or microwaved for 10 min at 150° C.). After evaporation of the solvent, the crude residue was neutralized with a saturated solution of NaHCO₃. The expected compound was precipitated, was filtered, was washed with water and was dried over Na₂SO₄, was filtered and was concentrated. The resulting crude product was purified by flash chromatography over silica gel using DCM/AcOEt (90:10) as eluent to yield after evaporation N-(pyridin-2-yl)-4-(3-(trifluoromethyl)-1H-pyrazol-4-yl)thiazol-2-amine (0.27 mmol, 85 mg, 47%) as a white solid.

M.p.: 250° C.;

LC (Zorbax SB-$C_{18}$, 3.5 µm, 4.6×30 mm Column): RT=2.07 min; MS m/z $ES^+$=312;

$^1$H NMR (300 MHz, DMSO) δ 11.32 (1H, s), 8.32 (1H, dd), 8.19 (1H, s), 7.75-7.64 (1H, m), 7.12 (1H, d), 6.98-6.85 (2H, m).

Example 5

5-Methyl-4-(1H-pyrazol-4-yl)-N-(pyridin-2-yl)thiazol-2-amine (Final Compound 1-16)

N-Methoxy-1-(4-methoxybenzyl)-N-methyl-1H-pyrazole-4-carboxamide

According to Scheme 3 Step 1: A solution of 1-(4-methoxybenzyl)-1H-pyrazole-4-carboxylic acid (34.4 mmol, 8.00 g), oxalyl chloride (68.9 mmol, 5.92 mL) and a drop of DMF in DCM (80 mL) was stirred for 1 hour at room temperature. After evaporation, the crude product was dissolved in DCM (30 mL) and was added at 0° C. to a solution of N,O-dimethylhydroxylamine hydrochloride (103 mmol, 6.31 g) in DCM (100 mL) followed by Et₃N (138 mmol, 19.2 mL). The reaction mixture was stirred for 1 hour at room temperature. The reaction was quenched with a saturated solution of Na₂CO₃ (300 mL) and the aqueous phase was extracted with DCM. The organic phase was dried over MgSO₄, was filtered and was concentrated to yield N-methoxy-1-(4-methoxybenzyl)-N-methyl-1H-pyrazole-4-carboxamide (33.8 mmol, 9.30 g, 98%) as a beige solid.

LC (Zorbax SB-$C_{18}$, 3.5 µm, 4.6×50 mm Column): RT=1.78 min; MS m/z $ES^+$=276.

1-(1-(4-Methoxybenzyl)-1H-pyrazol-4-yl)propan-1-one

According to Scheme 3 Step 2: Ethylmagnesium bromide (3N, 37.2 mmol, 12.4 mL) was added dropwise at room temperature to a solution of N-methoxy-1-(4-methoxybenzyl)-N-methyl-1H-pyrazole-4-carboxamide (33.8 mmol, 9.30 g) in THF (80 mL) and the reaction mixture was stirred for 1 hour. Then ethylmagnesium bromide (3N, 37.2 mmol, 12.4 mL) was added and the reaction mixture was stirred for 1 hour. Finally some more ethylmagnesium bromide (3N, 74.4 mmol, 24.8 mL) was added and the reaction mixture was stirred for 1.5 hour at 50° C. The reaction was quenched with HCl (1 N, 300 mL) and the aqueous phase was extracted with DCM. The organic phase was dried over MgSO₄, was filtered and was concentrated to yield 1-(1-(4-methoxybenzyl)-1H-pyrazol-4-yl)propan-1-one (32.7 mmol, 8.00 g, 97%) as a yellow oil.

LC (Zorbax SB-$C_{18}$, 3.5 µm, 4.6×50 mm Column): RT=2.04 min; MS m/z $ES^+$=245.

2-Bromo-1-(1-(4-methoxybenzyl)-1H-pyrazol-4-yl)propan-1-one

According to Scheme 3 Step 3: A solution of 1-(1-(4-methoxybenzyl)-1H-pyrazol-4-yl)propan-1-one (32.7 mmol, 8.00 g) and CuBr₂ (55.7 mmol, 12.4 g) in AcOEt (130 mL) was stirred under reflux for 2 hours. After addition of silica and evaporation, the crude residue was purified by flash chromatography over silica gel using DCM/MeOH (99:1) as eluent to yield after evaporation 2-bromo-1-(1-(4-methoxybenzyl)-1H-pyrazol-4-yl)propan-1-one (23.8 mmol, 7.70 g, 73%) as a colorless oil.

LC (Zorbax SB-$C_{18}$, 3.5 µm, 4.6×50 mm Column): RT=2.39 min; MS m/z $ES^+$=324.

4-(1-(4-Methoxybenzyl)-1H-pyrazol-4-yl)-5-methyl-N-(pyridin-2-yl)thiazol-2-amine According to Scheme 3 Step 4: A solution of 2-bromo-1-(1-(4-methoxybenzyl)-1H-pyrazol-4-yl)propan-1-one (23.8 mmol, 7.70 g) and of 1-(pyridin-2-yl)thiourea (26.2 mmol, 4.02 g) in EtOH (200 mL) was stirred under reflux overnight. The reaction was quenched with water (200 mL) and the aqueous phase was extracted with DCM. The organic phase was dried over MgSO₄, was filtered and was concentrated to yield a brown solid. The resulting crude product was purified by flash chromatography over silica gel using DCM/AcOEt (98:2) as eluent to yield after evaporation 4-(1-(4-methoxybenzyl)-1H-pyrazol-4-yl)-5-methyl-N-(pyridin-2-yl)thiazol-2-amine (20.7 mmol, 7.80 g, 87%) as a beige solid.

LC (Zorbax SB-C18, 3.5 µm, 4.6×50 mm Column): RT=2.29 min; MS m/z ES+=378.

5-Methyl-4-(1H-pyrazol-4-yl)-N-(pyridin-2-yl)thiazol-2-amine

According to Scheme 3 Step 5: A solution of 4-(1-(4-methoxybenzyl)-1H-pyrazol-4-yl)-5-methyl-N-(pyridin-2-yl)thiazol-2-amine (0.37 mmol, 140 mg) in TFA (1.5 mL) was microwaved for 30 min at 150° C. The reaction mixture was neutralized with a saturated solution of Na₂CO₃ and the aqueous phase was extracted with DCM. The organic phase was dried over MgSO₄, was filtered and was concentrated. The resulting crude product was purified by flash chromatography over silica gel using DCM/MeOH (95:5) as eluent and washed with Et₂O to yield after evaporation 5-methyl-4-(1H-pyrazol-4-yl)-N-(pyridin-2-yl)thiazol-2-amine (0.15 mmol, 38 mg, 40%) as a white solid.

M.p.: 291-294° C.;

LC (Zorbax SB-$C_{18}$, 3.5 µm, 4.6×50 mm Column): RT=1.47 min; MS m/z $ES^+$=258;

¹H NMR (300 MHz, DMSO) 12.93 (1H, s), 11.15 (1H, s), 8.25 (1H, dd), 8.00-7.75 (2H, m), 7.70-7.62 (1H, m), 7.01 (1H, d), 6.90-6.80 (1H, m), 2.39 (3H, s).

Example 6

5-Chloro-4-(1H-pyrazol-4-yl)-N-(pyridin-2-yl)thiazol-2-amine (Final Compound 1-32)

N-(4-(1-(4-Methoxybenzyl)-1H-pyrazol-4-yl)-5-chlorothiazol-2-yl)pyridin-2-amine

According to Scheme 4 Step 1 Method A: A solution of N-(4-(1-(4-methoxybenzyl)-1H-pyrazol-4-yl)thiazol-2-yl)pyridin-2-amine (1.38 mmol, 500 mg) and N-chlorosuccinimide (1.38 mmol, 184 mg) in DMF (3 mL) was stirred for 1 hour at 50° C. The reaction mixture was diluted with AcOEt (250 mL) and the organic phase was washed with a saturated solution of $Na_2CO_3$. The organic phase was dried over $MgSO_4$, was filtered and was concentrated to yield N-(4-(1-(4-methoxybenzyl)-1H-pyrazol-4-yl)-5-chlorothiazol-2-yl)pyridin-2-amine (1.16 mmol, 460 mg, 84%) as a beige solid.

LC (Zorbax SB-C18, 3.5 µm, 4.6×50 mm Column): RT=2.95 min; MS m/z ES+=398.

5-Chloro-4-(1H-pyrazol-4-yl)-N-(pyridin-2-yl)thiazol-2-amine

According to Scheme 4 Step 2: A solution of N-(4-(1-(4-methoxybenzyl)-1H-pyrazol-4-yl)-5-chlorothiazol-2-yl)pyridin-2-amine (0.50 mmol, 140 mg) in TFA (2 mL) was microwaved for 10 min at 150° C. After evaporation of the solvent, the crude residue was neutralized with a saturated solution of $Na_2CO_3$ (50 mL). The aqueous phase was extracted with DCM/MeOH (70:30, 50 mL). The organic phase was dried over $MgSO_4$, was filtered and was concentrated. The resulting crude product was purified by flash chromatography over silica gel using DCM/MeOH (95:5) as eluent and was washed with $Et_2O$ to yield after evaporation 5-chloro-4-(1H-pyrazol-4-yl)-N-(pyridin-2-yl)thiazol-2-amine (0.25 mmol, 70 mg, 50%) as a white solid.

M.p.: 282-285° C.;
LC (Zorbax SB-$C_{18}$, 3.5 µm, 4.6×50 mm Column): RT=2.17 min; MS m/z ES⁺=278;
¹H NMR (300 MHz, DMSO) 11.62 (1H, s), 8.30 (1H, d), 8.20-8.11 (1H, m), 7.99-7.90 (1H, m), 7.77-7.69 (1H, m), 7.04 (1H, d), 6.99-6.93 (1H, m).

Example 7

5-Fluoro-4-(1H-pyrazol-4-yl)-N-(pyridin-2-yl)thiazol-2-amine (Final Compound 1-56)

N-(4-(1-(4-Methoxybenzyl)-1H-pyrazol-4-yl)-5-fluorothiazol-2-yl)pyridin-2-amine

According to Scheme 4 Step 1 Method B: Select-Fluor (0.13 mmol, 48 mg) was added portionwise to a solution of 4-(1-(4-methoxybenzyl)-1H-pyrazol-4-yl)-N-(pyridin-2-yl)thiazol-2-amine (0.27 mmol, 100 mg) and of 2,6-dimethylpyridine (0.27 mmol, 32 µL) in DMF (3 mL) at 0° C. The reaction mixture was stirred at room temperature for 6 hours. Then Select-Fluor (0.13 mmol, 48 mg) was added and the reaction mixture was stirred at room temperature overnight. The reaction was quenched with water (50 mL) and the aqueous phase was extracted with DCM. The organic phase was dried over $MgSO_4$, was filtered and was concentrated to yield a beige solid. The resulting crude product was purified by flash chromatography over silica gel using cyclohexane/AcOEt (70:30) as eluent to yield after evaporation N-(4-(1-(4-methoxybenzyl)-1H-pyrazol-4-yl)-5-fluorothiazol-2-yl)pyridin-2-amine (0.12 mmol, 46 mg, 44%) as a white solid.

LC (Zorbax SB-C18, 3.5 µm, 4.6×50 mm Column): RT=2.78 min; MS m/z ES+=382.

5-Fluoro-4-(1H-pyrazol-4-yl)-N-(pyridin-2-yl)thiazol-2-amine

According to Scheme 4 Step 2: A solution of N-(4-(1-(4-methoxybenzyl)-1H-pyrazol-4-yl)-5-fluorothiazol-2-yl)pyridin-2-amine (0.12 mmol, 46 mg) in TFA (1 mL) was microwaved for 10 min at 140° C. The reaction mixture was neutralized with a saturated solution of $Na_2CO_3$ (10 mL) and water (20 mL). The aqueous phase was filtered to afford a brown solid. The resulting crude product was purified by flash chromatography over silica gel using DCM/MeOH (95:5) as eluent to yield after evaporation 5-fluoro-4-(1H-pyrazol-4-yl)-N-(pyridin-2-yl)thiazol-2-amine (61 µmol, 16 mg, 51%) as a brown solid.

LC (Zorbax SB-$C_{18}$, 3.5 µm, 4.6×50 mm Column): RT=1.98 min; MS m/z ES⁺=262;
¹H NMR (300 MHz, DMSO) 11.40 (1H, s), 8.27 (1H, d), 8.05-7.85 (1H, br s), 7.85-7.65 (1H, br s), 7.78-7.65 (1H, m), 7.01 (1H, d), 6.96-6.90 (1H, m).

Example 8

4-(1H-Pyrazol-4-yl)-2-(pyridin-2-ylamino)thiazol-5-carbonitrile (Final Compound 1-47)

3-(1-(4-Methoxybenzyl)-1H-pyrazol-4-yl)-3-oxopropanenitrile

According to Scheme 5 Step 1: A solution of 1-(1-(4-methoxybenzyl)-1H-pyrazol-4-yl)-2-bromoethanone (9.70 mmol, 3.00 g) and potassium cyanide (14.6 mmol, 948 mg) in 120 mL of water/MeOH/THF (1:1:1) was stirred for 30 minutes at room temperature. The reaction mixture was diluted with water (150 mL) and the aqueous phase was extracted with DCM. The organic phase was dried over $MgSO_4$, was filtered and was concentrated to yield 3-(1-(4-methoxybenzyl)-1H-pyrazol-4-yl)-3-oxopropanenitrile (9.40 mmol, 2.40 g, 97%).

LC (Zorbax SB-C18, 3.5 µm, 4.6×50 mm Column): RT=1.87 min.

4-(1-(4-Methoxybenzyl)-1H-pyrazol-4-yl)-2-(pyridin-2-ylamino)thiazol-5-carbonitrile According to Scheme 5 Step 2: A solution of 3-(1-(4-methoxybenzyl)-1H-pyrazol-4-yl)-3-oxopropanenitrile (9.40 mmol, 2.40 g) and of 1-(pyridin-2-yl)thiourea (9.40 mmol, 1.44 g) in pyridine (30 mL) was stirred at 80° C. for 1 hour. The reaction was quenched with water (100 mL) and the aqueous phase was extracted with DCM. The organic phase was dried over $MgSO_4$, was filtered and was concentrated to yield a brown solid. The resulting crude product was purified by flash chromatography over silica gel using cyclohexane/AcOEt (60:40) as eluent to yield after evaporation 4-(1-(4-methoxybenzyl)-1H-pyrazol-4-yl)-2-(pyridin-2-ylamino)thiazol-5-carbonitrile (0.93 mmol, 360 mg, 10%) as a brown solid.

4-(1H-Pyrazol-4-yl)-2-(pyridin-2-ylamino)thiazol-5-carbonitrile

According to Scheme 5 Step 3: A solution of 4-(1-(4-methoxybenzyl)-1H-pyrazol-4-yl)-2-(pyridin-2-ylamino)thiazol-5-carbonitrile (0.93 mmol, 360 mg) in TFA (3 mL) was microwaved for 5 min at 140° C. The reaction mixture was neutralized with a saturated solution of $Na_2CO_3$ (40 mL) and water (50 mL). The aqueous phase was filtered to afford a brown solid which was recrystallized thrice with DMF/water to yield 4-(1H-pyrazol-4-yl)-2-(pyridin-2-ylamino)thiazol-5-carbonitrile (0.24 mmol, 65 mg, 26%) as an off-white solid.

LC (Zorbax SB-$C_{18}$, 3.5 μm, 4.6×50 mm Column): RT=1.99 min; MS m/z ES$^+$=269.

Example 9

4-(1H-Pyrazol-4-yl)-N-(pyridin-2-yl)-5-(trifluoromethyl)thiazol-2-amine (Final Compound 1-54)

4-Iodo-1-(4-methoxybenzyl)-1H-pyrazole

According to Scheme 6 Step 1: A suspension of 4-iodo-1H-pyrazole (26.3 mmol, 5.11 g), 1-(chloromethyl)-4-methoxybenzene (29.0 mmol, 3.95 mL) and $K_2CO_3$ (39.5 mmol, 5.46 g) in acetonitrile (150 mL) was heated at 60° C. overnight. The reaction mixture was cooled to room temperature and was filtered. The filtrate was concentrated under reduced pressure. The crude product was purified by flash chromatography over silica gel using DCM as eluent to afford 4-iodo-1-(4-methoxybenzyl)-1H-pyrazole (23.2 mmol, 7.3 g, 88%) as a yellow solid.

LC (Zorbax SB-$C_{18}$, 3.5 μm, 4.6×50 mm Column).

3,3,3-Trifluoro-1-(1-(4-methoxybenzyl)-1H-pyrazol-4-yl)propan-1-one

According to Scheme 6 Step 2: A solution of 4-iodo-1-(4-methoxybenzyl)-1H-pyrazole (6.05 mmol, 1.90 g), (Z)-3,3,3-trifluoro-1-methoxyprop-1-ene (18.1 mmol, 2.29 g), silver carbonate (6.05 mmol, 1.67 g), Pd(OAc)$_2$ (0.18 mmol, 41 mg) and PPh$_3$ (0.36 mmol, 95 mg) in DMF (30 mL) was stirred at 80° C. for 2 days. After addition of HCl (1 N, 100 mL), the reaction mixture was stirred at room temperature for 2 hours. The reaction was quenched with water (100 mL) and the aqueous phase was extracted with DCM. The organic phase was dried over MgSO$_4$, was filtered and was concentrated to yield a brown solid. The resulting crude product was purified by flash chromatography over silica gel using cyclohexane/AcOEt (70:30) as eluent to yield after evaporation 3,3,3-trifluoro-1-(1-(4-methoxybenzyl)-1H-pyrazol-4-yl)propan-1-one (3.25 mmol, 970 mg, 54%) as a beige solid.

LC (Zorbax SB-$C_{18}$, 3.5 μm, 4.6×50 mm Column): RT=2.31 min.

4-(1-(4-Methoxybenzyl)-1H-pyrazol-4-yl)-N-(pyridin-2-yl)-5-(trifluoromethyl)thiazol-2-amine According to Scheme 6 Step 3: A solution of 3,3,3-trifluoro-1-(1-(4-methoxybenzyl)-1H-pyrazol-4-yl)propan-1-one (2.51 mmol, 750 mg), 1-(pyridin-2-yl)thiourea (2.51 mmol, 385 mg) and of iodine (2.51 mmol, 638 mg) in pyridine (15 mL) was stirred at 90° C. for 6 hours. The reaction was quenched with water (100 mL) and the aqueous phase was extracted with DCM. The organic phase was dried over MgSO$_4$, was filtered and was concentrated to yield a brown solid. The resulting crude product was purified by flash chromatography over silica gel using cyclohexane/AcOEt (60:40) as eluent to yield after evaporation 4-(1-(4-methoxybenzyl)-1H-pyrazol-4-yl)-N-(pyridin-2-yl)-5-(trifluoromethyl)thiazol-2-amine (1.58 mmol, 680 mg, 63%) as a beige solid.

LC (Zorbax SB-$C_{18}$, 3.5 μm, 4.6×50 mm Column): RT=3.02 min; MS m/z ES$^+$=432.

4-(1H-Pyrazol-4-yl)-N-(pyridin-2-yl)-5-(trifluoromethyl)thiazol-2-amine

According to Scheme 6 Step 4: A solution of 4-(1-(4-methoxybenzyl)-1H-pyrazol-4-yl)-N-(pyridin-2-yl)-5-(trifluoromethyl)thiazol-2-amine (1.58 mmol, 680 mg) in TFA (5 mL) was microwaved for 10 min at 150° C. The reaction mixture was neutralized with a saturated solution of $Na_2CO_3$ (40 mL) and water (70 mL). The aqueous phase was filtered to afford a brown solid. The resulting crude product was purified by flash chromatography over silica gel using DCM/MeOH/Et$_3$N (94:5:1) as eluent to afford a beige solid. The product was then purified by flash chromatography over $C_{18}$ column using water/ACN (30:70 to 50:50) as eluent and was washed with MeOH to yield after evaporation 4-(1H-pyrazol-4-yl)-N-(pyridin-2-yl)-5-(trifluoromethyl)thiazol-2-amine (0.55 mmol, 170 mg, 35%) as an off-white solid.

M.p.: 250° C. (dec.);
LC (Zorbax SB-$C_{18}$, 3.5 μm, 4.6×50 mm Column): RT=2.34 min; MS m/z ES$^+$=312;
$^1$H NMR (300 MHz, DMSO) 11.96 (1H, s), 8.38 (1H, d), 8.05-7.85 (2H, br s), 7.82-7.74 (1H, m), 7.12 (1H, d), 7.05-6.99 (1H, m).

Example 10

5-Phenyl-4-(1H-pyrazol-4-yl)-N-(pyridin-2-yl)thiazol-2-amine (Final Compound 1-55)

1-(4-Methoxybenzyl)-4-(phenylethynyl)-1H-pyrazole

According to Scheme 7 Step 1: A solution of 4-iodo-1-(4-methoxybenzyl)-1H-pyrazole (4.78 mmol, 1.50 g), ethynylbenzene (6.21 mmol, 0.68 mL), PdCl$_2$(PPh$_3$)$_2$ (0.24 mmol, 168 mg) and CuI (0.48 mmol, 91 mg) in diethylamine (30 mL) was stirred at 50° C. for 3 hours. The reaction was quenched with water (150 mL) and the aqueous phase was extracted with DCM. The organic phase was dried over MgSO$_4$, was filtered and was concentrated to yield a brown solid. The resulting crude product was purified by flash chromatography over silica gel using cyclohexane/AcOEt (80:20) as eluent to yield after evaporation 1-(4-methoxybenzyl)-4-(phenylethynyl)-1H-pyrazole (3.92 mmol, 1.13 g, 82%) as a beige solid.

LC (Zorbax SB-$C_{18}$, 3.5 μm, 4.6×50 mm Column): RT=2.92 min; MS m/z ES$^+$=289.

2-Phenyl-1-(1H-pyrazol-4-yl)ethanone

According to Scheme 7 Step 2: A solution of 1-(4-methoxybenzyl)-4-(phenylethynyl)-1H-pyrazole (3.12 mmol, 900 mg), SnCl$_2$ (12.5 mmol, 2.37 g) and of HCl (37%, 20 mL) in EtOH (20 mL) was stirred overnight at 90° C. The reaction was quenched with water (100 mL) and the aqueous phase was extracted with DCM. The organic phase was dried over MgSO$_4$, was filtered and was concentrated to yield a brown solid. The resulting crude product was purified by flash chromatography over silica gel using DCM/MeOH (96:4) as eluent to yield after evaporation 2-phenyl-1-(1H-pyrazol-4-yl)ethanone (1.99 mmol, 370 mg, 64%) as a white solid.

LC (Zorbax SB-C$_{18}$, 3.5 µm, 4.6×50 mm Column): RT=1.57 min; MS m/z ES$^+$=187.

2-Bromo-2-phenyl-1-(1H-pyrazol-4-yl)ethanone

According to Scheme 7 Step 3: A solution of 2-phenyl-1-(1H-pyrazol-4-yl)ethanone (0.54 mmol, 100 mg) and CuBr$_2$ (0.91 mmol, 204 g) in AcOEt (5 mL) was stirred under reflux for 4 hours. After addition of silica and evaporation, the crude residue was purified by flash chromatography over silica gel using DCM/MeOH (99:1) as eluent to yield after evaporation 2-bromo-2-phenyl-1-(1H-pyrazol-4-yl)ethanone (0.23 mmol, 60 mg, 42%) as a brown solid.

LC (Zorbax SB-C$_{18}$, 3.5 µm, 4.6×50 mm Column): RT=1.90 min; MS m/z ES$^+$=266.

5-Phenyl-4-(1H-pyrazol-4-yl)-N-(pyridin-2-yl)thiazol-2-amine

According to Scheme 7 Step 4: A solution of 2-bromo-2-phenyl-1-(1H-pyrazol-4-yl)ethanone (0.23 mmol, 60 mg) and of 1-(pyridin-2-yl)thiourea (0.23 mmol, 35 mg) in EtOH (4 mL) was stirred at 90° C. overnight. The reaction was quenched with a saturated solution of Na$_2$CO$_3$ (50 mL) and the aqueous phase was extracted with DCM/MeOH (90:10, 50 mL). The organic phase was dried over MgSO$_4$, was filtered and was concentrated to yield a brown solid. The resulting crude product was purified by flash chromatography over silica gel using DCM/MeOH (96:4) as eluent to yield after evaporation 5-phenyl-4-(1H-pyrazol-4-yl)-N-(pyridin-2-yl)thiazol-2-amine (53 µmol, 17 mg, 24%) as a white solid.

M.p.: 266-267° C.;
LC (Zorbax SB-C$_{18}$, 3.5 µm, 4.6×50 mm Column): RT=2.31 min; MS m/z ES$^+$=320;
$^1$H NMR (300 MHz, DMSO) 11.43 (1H, s), 8.28 (1H, d), 7.71 (1H, dd), 7.45-7.39 (7H, m), 7.07 (1H, d), 6.91 (1H, dd).

Example 11

(4-(1H-Pyrazol-4-yl)-2-(pyridin-2-ylamino)thiazol-5-yl)methanol (Final Compound 1-57)

According to Scheme 8: A solution of N-(4-(1H-pyrazol-4-yl)thiazol-2-yl)pyridin-2-amine (0.41 mmol, 100 mg, Co.nr. 1-25), formaldehyde (0.5 mL, 30% in water) and Et$_3$N (0.5 mL) in THF (0.5 mL) was microwaved for 15 min at 100° C. The reaction mixture was quenched with water (50 mL) and the aqueous phase was extracted with DCM/MeOH (90:10). The organic phase was dried over MgSO$_4$, was filtered and was concentrated to yield a brown solid. The resulting crude product was purified by flash chromatography over C$_{18}$ column using water/ACN (80:20) as eluent to yield after evaporation (4-(1H-pyrazol-4-yl)-2-(pyridin-2-ylamino)thiazol-5-yl)methanol (91 µmol, 25 mg, 22%) as a white solid.

M.p.: 250° C. (dec.);
LC (Zorbax SB-C$_{18}$, 3.5 µm, 4.6×50 mm Column): RT=1.12 min; MS m/z ES$^+$=274;
$^1$H NMR (300 MHz, DMSO) 11.24 (1H, s), 8.28 (1H, dd), 8.05-7.90 (1H, br s), 7.85-7.70 (1H, br s), 7.69-7.64 (1H, m), 7.03 (1H, d), 6.93-6.86 (1H, m), 5.39 (1H, t), 4.64 (2H, d).

Example 12

4-(3-Ethyl-1H-pyrazol-4-yl)-N-(pyridin-2-yl)thiazol-2-amine (Final Compound 1-61)

(E)-Ethyl 2-((dimethylamino)methylene)-3-oxopentanoate

According to Scheme 9 Step 1: A solution of ethyl 3-oxopentanoate (13.9 mmol, 2.00 g) and of 1,1-dimethoxy-N,N-dimethylmethanamine (13.9 mmole, 1.84 mL) in DMF (10 mL) was microwaved for 30 min at 120° C. After evaporation of the solvent, 2.76 g (13.9 mmol) of (E)-ethyl 2-((dimethylamino)methylene)-3-oxopentanoate were obtained and used without further purification.

Ethyl 3-ethyl-1H-pyrazole-4-carboxylate

According to Scheme 9 Step 2: A solution of (E)-ethyl 2-((dimethylamino)methylene)-3-oxopentanoate (13.9 mmol, 2.76 g) and hydrazine (13.9 mmol, 0.44 mL) in EtOH (50 mL) was stirred for 1 hour at room temperature. After evaporation of the solvent, the resulting crude product was purified by flash chromatography over silica gel using cyclohexane/AcOEt (80:20) as eluent to yield after evaporation ethyl 3-ethyl-1H-pyrazole-4-carboxylate (6.00 mol, 1.01 g, 43%) as a yellow oil.

LC (Zorbax SB-C$_{18}$, 3.5 µm, 4.6×50 mm Column): RT=1.53 min; MS m/z ES$^+$=169.

Ethyl 5-ethyl-1-(4-methoxybenzyl)-1H-pyrazole-4-carboxylate and ethyl 3-ethyl-1-(4-methoxybenzyl)-1H-pyrazole-4-carboxylate According to Scheme 9 Step 3: A suspension of ethyl 3-ethyl-1H-pyrazole-4-carboxylate (5.95 mmol, 1.0 g), 1-(chloromethyl)-4-methoxybenzene (6.54 mmol, 0.89 mL) and K$_2$CO$_3$ (17.8 mmol, 2.46 g) in acetone (20 mL) was heated at 60° C. overnight. After evaporation of the solvent, water was added and the aqueous phase was extracted with DCM. The organic phase was dried over Na$_2$SO$_4$, was filtered and was concentrated under reduced pressure. The crude product was purified by flash chromatography over silica gel using cyclohexane/AcOEt (95:5) as eluent to afford a mixture of ethyl 5-ethyl-1-(4-methoxybenzyl)-1H-pyrazole-4-carboxylate and of ethyl 3-ethyl-1-(4-methoxybenzyl)-1H-pyrazole-4-carboxylate (2.77 mmol, 800 mg, 47%) as a yellow oil.

LC (Zorbax SB-C$_{18}$, 3.5 µm, 4.6×30 mm Column): RT=2.58 min.

3-Ethyl-1-(4-methoxybenzyl)-1H-pyrazole-4-carboxylic acid and 5-ethyl-1-(4-methoxybenzyl)-1H-pyrazole-4-carboxylic acid According to Scheme 9 Step 4: A solution of LiOH (8.32 mmol, 356 mg) in water (4 mL) was added to a solution of a mixture of ethyl 5-ethyl-1-(4-methoxybenzyl)-1H-pyrazole-4-carboxylate and of ethyl 3-ethyl-1-(4-methoxybenzyl)-1H-pyrazole-4-carboxylate (2.77 mmol, 800 mg) in MeOH/THF (1:1, 5 mL) and the reaction mixture was heated at 80° C. for 3 hours. After evaporation of the solvent, HCl 2 M was added and the aqueous phase was extracted with DCM. The organic phase was washed with brine, was dried over Na$_2$SO$_4$, was filtered and was concentrated under reduced pressure to yield a mixture of 3-ethyl-1-(4-methoxybenzyl)-1H-pyrazole-4-carboxylic acid and of 5-ethyl-1-(4-methoxybenzyl)-1H- pyrazole-4-carboxylic acid (2.77 mmol, 0.70 g, 100%) as a colorless oil. The crude product was used without purification.

LC (Zorbax SB-$C_{18}$, 3.5 μm, 4.6×30 mm Column): RT=1.87 min.

3-Ethyl-1-(4-methoxybenzyl)-1H-pyrazole-4-carbonyl chloride and of 5-ethyl-1-(4-methoxybenzyl)-1H-pyrazole-4-carbonyl chloride According to Scheme 9 Step 5: A solution of a mixture of 3-ethyl-1-(4-methoxybenzyl)-1H-pyrazole-4-carboxylic acid and of 5-ethyl-1-(4-methoxybenzyl)-1H-pyrazole-4-carboxylic acid (2.77 mmol, 722 mg), thionyl chloride (8.32 mmol, 0.60 mL) and drops of DMF in DCM (10 mL) was stirred for 1 hour at room temperature. After evaporation of the solvent, the crude residue was treated with toluene and was coevaporated to dryness to yield a mixture of 3-ethyl-1-(4-methoxybenzyl)-1H-pyrazole-4-carbonyl chloride and of 5-ethyl-1-(4-methoxybenzyl)-1H-pyrazole-4-carbonyl chloride (2.77 mmol, 0.77 g). The crude product was used without purification.

2-Bromo-1-(3-ethyl-1-(4-methoxybenzyl)-1H-pyrazol-4-yl)ethanone and 2-bromo-1-(5-ethyl-1-(4-methoxybenzyl)-1H-pyrazol-4-yl)ethanone According to Scheme 9 Step 6: A solution of TMSdiazomethane (6.10 mmol, 3.05 mL) was added to a solution of a mixture of 3-ethyl-1-(4-methoxybenzyl)-1H-pyrazole-4-carbonyl chloride and of 5-ethyl-1-(4-methoxybenzyl)-1H-pyrazole-4-carbonyl chloride (2.77 mmol, 0.77 g) in acetonitrile (10 mL) at 0° C. The reaction mixture was stirred at room temperature overnight. HBr (9.71 mmol, 1.1 mL, 48%) was added at 0° C. to the reaction mixture. The reaction mixture was stirred at room temperature overnight. After evaporation of the solvent, crude product was purified by flash chromatography over silica gel using cyclohexane/AcOEt (60:40) as eluent to yield after evaporation a mixture of 2-bromo-1-(3-ethyl-1-(4-methoxybenzyl)-1H-pyrazol-4-yl)ethanone and of 2-bromo-1-(5-ethyl-1-(4-methoxybenzyl)-1H-pyrazol-4-yl)ethanone (2.37 mmol, 0.80 g, 86%) as an off-white solid.

4-(3-Ethyl-1-(4-methoxybenzyl)-1H-pyrazol-4-yl)-N-(pyridin-2-yl)thiazol-2-amine and 4-(5-ethyl-1-(4-methoxybenzyl)-1H-pyrazol-4-yl)-N-(pyridin-2-yl)thiazol-2-amine According to Scheme 9 Step 7: A solution of a mixture of 2-bromo-1-(3-ethyl-1-(4-methoxybenzyl)-1H-pyrazol-4-yl)ethanone and of 2-bromo-1-(5-ethyl-1-(4-methoxybenzyl)-1H-pyrazol-4-yl)ethanone (1.19 mmol, 400 mg) and of 1-(pyridin-2-yl)thiourea (1.19 mmol, 182 mg) in EtOH (2.5 mL) was stirred under reflux for 2 hours. After filtration, the precipitate was dried to yield a mixture of 4-(3-ethyl-1-(4-methoxybenzyl)-1H-pyrazol-4-yl)-N-(pyridin-2-yl)thiazol-2-amine and of 4-(S-ethyl-1-(4-methoxybenzyl)-1H-pyrazol-4-yl)-N-(pyridin-2-yl)thiazol-2-amine (1.18 mmol, 464 mg) as a white solid. The crude product was used without purification.

LC (Zorbax SB-$C_{18}$, 3.5 μm, 4.6×30 mm Column): RT=2.57 min; MS m/z ES$^+$=392.

4-(3-Ethyl-1H-pyrazol-4-yl)-N-(pyridin-2-yl)thiazol-2-amine

According to Scheme 9 Step 8: A solution of a mixture of 4-(3-ethyl-1-(4-methoxybenzyl)-1H-pyrazol-4-yl)-N-(pyridin-2-yl)thiazol-2-amine and of 4-(5-ethyl-1-(4-methoxybenzyl)-1H-pyrazol-4-yl)-N-(pyridin-2-yl)thiazol-2-amine (1.18 mmol, 464 mg) in TFA (0.5 mL) was microwaved for 5 min at 140° C. The crude residue was neutralized with a saturated solution of $Na_2CO_3$ and the aqueous phase was extracted with DCM. The organic phase was dried over $Na_2SO_4$, was filtered and was concentrated. The resulting orange oil was purified by flash chromatography over silica gel using DCM/MeOH (100:0 to 90:10) as eluent to yield after evaporation 4-(3-ethyl-1H-pyrazol-4-yl)-N-(pyridin-2-yl)thiazol-2-amine (0.77 mmol, 209 mg, 65%) as a white solid.

M.p.: 196-198° C.;
LC (Zorbax SB-$C_{18}$, 3.5 nm, 4.6×30 mm Column): RT=1.68 min; MS m/z ES$^+$=272;
$^1$H NMR (300 MHz, DMSO) 12.70-12.50 (1H, s), 11.24 (1H, s), 8.29 (1H, d), 7.90-7.62 (2H, m), 7.10 (1H, d), 6.98-6.85 (1H, m), 6.83 (1H, s), 3.05-2.75 (2H, m), 1.23 (3H, t).

Example 13

1-(3-Methyl-4-(5-(phenylamino)-1,2,4-thiadiazol-3-yl)-1H-pyrazol-1-yl)ethanone (Final Compound 1-2)

According to Scheme 10 Method A: Anhydride acetic (36 μL, 0.39 mmol) and pyridine (31 μL, 0.39 mmol) were added to a solution of 3-(3-methyl-1H-pyrazol-4-yl)-N-phenyl-1,2,4-thiadiazol-5-amine (0.39 mmol, 0.10 mg, Co.nr. 1-1) in DCM (5 mL) at room temperature. The reaction mixture was stirred at room temperature for 14 hours. The organic phase was washed with water and with brine, was dried over $Na_2SO_4$, was filtered and was concentrated under reduced pressure. The crude product was triturated in MeOH to afford after filtration and evaporation 1-(3-methyl-4-(5-(phenylamino)-1,2,4-thiadiazol-3-yl)-1H-pyrazol-1-yl)ethanone (0.30 mmol, 90 mg, 77%) as a white solid.

M.p.: 204-208° C.;
LC (Zorbax SB-$C_{18}$, 3.5 nm, 4.6×50 mm Column): RT=4.41 min; MS m/z ES$^+$=300;
$^1$H NMR (300 MHz, DMSO) 11.05 (1H, s), 8.71 (1H, s), 7.70-7.55 (2H, m), 7.50-7.32 (2H, m), 7.15-7.05 (1H, m), 2.72 (3H, s), 2.61 (3H, s).

Example 14

2-Methyl-1-(4-(5-methyl-2-(pyridin-2-ylamino)thiazol-4-yl)-1H-pyrazol-1-yl)propan-1-one (Final Compound 1-26)

According to Scheme 10 Method B: To a cooled solution (0° C.) of N-(5-methyl-4-(1H-pyrazol-4-yl)thiazol-2-yl)pyridin-2-amine (0.39 mmol, 100 mg, Co.nr. 1-16) and $Et_3N$ (0.51 mmol, 0.07 mL) in THF (5 mL) was added dropwise isobutyryl chloride (0.39 mmol, 0.04 mL). The reaction mixture was stirred for 1 hour at 0° C. The reaction mixture was quenched with water (50 mL) and the aqueous phase was extracted with DCM. The organic phase was dried over $MgSO_4$, was filtered and was concentrated to yield a brown solid. The resulting crude product was purified by flash chromatography over silica gel using DCM/MeOH (99:1) as eluent to yield after evaporation 2-methyl-1-(4-(5-methyl-2-(pyridin-2-ylamino)thiazol-4-yl)-1H-pyrazol-1-yl)propan-1-one (0.16 mmol, 53 mg, 42%) as an off-white solid.

M.p.: 168° C.;
LC (Zorbax SB-$C_{18}$, 3.5 nm, 4.6×30 mm Column): RT=2.76 min; MS m/z ES$^+$=328;
$^1$H NMR (300 MHz, DMSO) 11.23 (1H, s), 8.47 (1H, s), 8.26 (1H, dd), 8.19 (1H, s), 7.72-7.64 (1H, m), 7.03 (1H, d), 6.93-6.87 (1H, m), 3.88-3.77 (1H, m), 2.47 (3H, s), 1.24 (6H, d).

Example 15

4-(5-Methyl-2-(pyridin-2-ylamino)thiazol-4-yl)-1H-pyrazole-1-carboxamide (Final Compound 1-27)

According to Scheme 11 Method A: A solution of N-(5-methyl-4-(1H-pyrazol-4-yl)thiazol-2-yl)pyridin-2-amine (0.39 mmol, 100 mg, Co.nr. 1-16), potassium cyanate (0.47 mmol, 18.2 mg), AcOH (2 mL) and water (50 mL) was stirred for 2 hours at room temperature. The reaction mixture was quenched with water (50 mL) and the aqueous phase was extracted with DCM/MeOH (90:10). The organic phase was dried over MgSO$_4$, was filtered and was concentrated to yield a brown solid. The resulting crude product was purified by flash chromatography over silica gel using DCM/MeOH (98:2) as eluent to yield after evaporation 4-(5-methyl-2-(pyridin-2-ylamino)thiazol-4-yl)-1H-pyrazole-1-carboxamide (0.39 mmol, 49 mg, 42%) as a white solid.

M.p.: 294-296° C.;
LC (Zorbax SB-C$_{18}$, 3.5 nm, 4.6×30 mm Column): RT=1.71 min; MS m/z ES$^+$=301;
$^1$H NMR (300 MHz, DMSO) 11.21 (1H, s), 8.39 (1H, s), 8.26 (1H, d), 8.03 (1H, s), 7.91 (2H, d), 7.72-7.64 (1H, m), 7.02 (1H, d), 6.93-6.87 (1H, m), 2.44 (3H, s).

Example 16

(4-(5-Methyl-2-(pyridin-2-ylamino)thiazol-4-yl)-1H-pyrazol-1-yl)(piperidin-1-yl)methanone (Final Compound 1-34)

According to Scheme 11 Method B: A solution of N-(5-methyl-4-(1H-pyrazol-4-yl)thiazol-2-yl)pyridin-2-amine (0.39 mmol, 100 mg, Co.nr. 1-16), piperidine-1-carbonyl chloride (0.58 mmol, 73 µL) and DBU (0.58 mmol, 87 µL) in THF (4 mL) was stirred for 24 hours at room temperature. After addition of piperidine-1-carbonyl chloride (0.78 mmol, 97 µL) and DBU (0.78 mmol, 116 µL), the reaction mixture was stirred for 4 days. The reaction mixture was quenched with water (50 mL) and the aqueous phase was extracted with DCM. The organic phase was dried over MgSO$_4$, was filtered and was concentrated to yield a beige solid. The resulting crude product was purified by flash chromatography over silica gel using DCM/MeOH (98:2) as eluent and washed with Et$_2$O/pentane (50:50) to yield after evaporation (4-(5-methyl-2-(pyridin-2-ylamino)thiazol-4-yl)-1H-pyrazol-1-yl)(piperidin-1-yl)methanone (0.19 mmol, 72 mg, 50%) as a white solid.

M.p.: 137-138° C.;
LC (Zorbax SB-C$_{18}$, 3.5 µm, 4.6×30 mm Column): RT=2.42 min; MS m/z ES$^+$=369;
$^1$H NMR (300 MHz, DMSO) 11.23 (1H, s), 8.32 (1H, s), 8.26 (1H, dd), 8.04 (1H, s), 7.71-7.64 (1H, m), 7.03 (1H, d), 6.89 (1H, t), 3.80-3.50 (4H, m), 2.44 (3H, s), 1.70-1.50 (6H, s).

Example 17

N-Isopropyl-4-(5-methyl-2-(pyridin-2-ylamino)thiazol-4-yl)-1H-pyrazole-1-carboxamide (Final Compound 1-50)

According to Scheme 11 Method C: A solution of N-(5-methyl-4-(1H-pyrazol-4-yl)thiazol-2-yl)pyridin-2-amine (0.39 mmol, 100 mg, Co.nr. 1-16), 2-isocyanatopropane (0.58 mmol, 57 µL) in THF (4 mL) was stirred for 2 hours at room temperature. The reaction mixture was quenched with water (50 mL) and the aqueous phase was extracted with DCM. The organic phase was dried over MgSO$_4$, was filtered and was concentrated to yield a brown solid. The resulting crude product was purified by flash chromatography over silica gel using DCM/MeOH (99:1) as eluent and washed with Et$_2$O to yield after evaporation N-isopropyl-4-(5-methyl-2-(pyridin-2-ylamino)thiazol-4-yl)-1H-pyrazole-1-carboxamide (0.25 mmol, 85 mg, 64%) as a white solid.

M.p.: 297-298° C.;
LC (Zorbax SB-C$_{18}$, 3.5 nm, 4.6×30 mm Column): RT=2.43 min; MS m/z ES$^+$=343;
$^1$H NMR (300 MHz, DMSO) 11.21 (1H, s), 8.40 (1H, s), 8.33 (1H, d), 8.28 (1H, dd), 8.04 (1H, s), 7.72-7.64 (1H, m), 7.02 (1H, d), 6.93-6.87 (1H, m), 4.05-3.96 (1H, m), 2.44 (3H, s), 1.22 (6H, d).

Example 18

5-Methyl-4-(1-(methylsulfonyl)-1H-pyrazol-4-yl)-N-(pyridin-2-yl)thiazol-2-amine (Final Compound 1-45)

According to Scheme 12: Methanesulfonyl chloride (36 µL, 0.47 mmol) was added dropwise to a solution of N-(5-methyl-4-(1H-pyrazol-4-yl)thiazol-2-yl)pyridin-2-amine (0.39 mmol, 100 mg, Co.nr. 1-16), Et$_3$N (0.58 mmol, 81 µL) in THF (5 mL) and the reaction mixture was stirred for 2 hours at room temperature. The reaction mixture was quenched with water (50 mL) and the aqueous phase was extracted with DCM. The organic phase was dried over MgSO$_4$, was filtered and was concentrated to yield a brown solid. The resulting crude product was purified by flash chromatography over silica gel using DCM/MeOH (98:2) as eluent and washed with Et$_2$O to yield after evaporation 5-methyl-4-(1-(methylsulfonyl)-1H-pyrazol-4-yl)-N-(pyridin-2-yl)thiazol-2-amine (0.20 mmol, 66 mg, 51%) as a white solid.

M.p.: 193° C.;
LC (Zorbax SB-C$_{18}$, 3.5 nm, 4.6×30 mm Column): RT=2.06 min; MS m/z ES$^+$=336;
$^1$H NMR (300 MHz, DMSO) 11.25 (1H, s), 8.36 (1H, s), 8.28-8.21 (2H, m), 7.72-7.64 (1H, m), 7.03 (1H, d), 6.93-6.86 (1H, m), 3.60 (3H, s).

Example 19

N-(2,5-Difluorophenyl)-6-(1H-pyrazol-4-yl)pyridin-2-amine (Final Compound 2-1)

1-(4-Methoxybenzyl)-4-(4,4,5,5-tetramethyl-1,3,2-dioxaborolan-2-yl)-1H-pyrazole According to Scheme 13 Step 1: A suspension of 4-(4,4,5,5-tetramethyl-1,3,2-dioxaborolan-2-yl)-1H-pyrazole (7.38 mmol, 1.43 g), 1-(chloromethyl)-4-methoxybenzene (7.38 mmol, 1.00 mL) and K$_2$CO$_3$ (7.38 mmol, 1.02 g) in acetonitrile (10 mL) was heated at 80° C. for 5 hours. Water was added and the aqueous phase was extracted with DCM. The organic phase was dried over Na$_2$SO$_4$, was filtered and was concentrated under reduced pressure to afford 1-(4-methoxybenzyl)-4-(4,4,5,5-tetramethyl-1,3,2-dioxaborolan-2-yl)-1H-pyrazole (6.68 mmol, 2.10 g, 91%) as a yellow oil.

LC (Zorbax SB-C$_{18}$, 3.5 µm, 4.6×30 mm Column): RT=2.55 min; MS m/z ES$^+$=315.

2-Bromo-6-(1-(4-methoxybenzyl)-1H-pyrazol-4-yl)pyridine

According to Scheme 13 Step 2: Pd(PPh$_3$)$_4$ (0.42 mmol, 488 mg) was added to a solution of 1-(4-methoxybenzyl)-4-

(4,4,5,5-tetramethyl-1,3,2-dioxaborolan-2-yl)-1H-pyrazole (4.22 mmol, 1.33 g), 2,6-dibromopyridine (4.22 mmol, 1.00 g) and of a 2 M solution of $K_3PO_4$ (6.33 mL) in DME (10 mL). The reaction mixture was stirred at 80° C. for 5 hours. The reaction was quenched with water and the aqueous phase was extracted with DCM. The organic phase was dried over $MgSO_4$, was filtered and was concentrated. The resulting crude product was purified by flash chromatography over silica gel using DCM as eluent to yield after evaporation 2-bromo-6-(1-(4-methoxybenzyl)-1H-pyrazol-4-yl)pyridine (2.90 mmol, 1.00 g, 61%) as a yellow oil.

LC (Zorbax SB-$C_{18}$, 3.5 µm, 4.6×30 mm Column): RT=2.62 min; MS m/z ES$^+$=345.

N-(2,5-Difluorophenyl)-6-(1-(4-methoxybenzyl)-1H-pyrazol-4-yl)pyridin-2-amine

According to Scheme 13 Step 3: A solution of 2-bromo-6-(1-(4-methoxybenzyl)-1H-pyrazol-4-yl)pyridine (0.58 mmol, 200 mg), 2,5-difluoroaniline (0.58 mmol, 58 µL) and KOtBu (0.58 mmol, 65 mg) in toluene (5 mL) was stirred for 15 hours at 100° C. The reaction was quenched with a saturated solution of $NH_4Cl$ and the aqueous phase was extracted with DCM. The organic phase was dried over $MgSO_4$, was filtered and was concentrated. The resulting crude product was purified by flash chromatography over silica gel using DCM/MeOH (98:2) as eluent to yield after evaporation N-(2,5-difluorophenyl)-6-(1-(4-methoxybenzyl)-1H-pyrazol-4-yl)pyridin-2-amine (0.25 mmol, 100 mg, 43%) as an orange oil.

LC (Zorbax SB-$C_{18}$, 3.5 nm, 4.6×30 mm Column): RT=2.93 min; MS m/z ES$^+$=393.

N-(2,5-Difluorophenyl)-6-(1H-pyrazol-4-yl)pyridin-2-amine

According to Scheme 13 Step 4: A solution of N-(2,5-difluorophenyl)-6-(1-(4-methoxybenzyl)-1H-pyrazol-4-yl)pyridin-2-amine (0.26 mmol, 100 mg) in TFA (5 mL) was microwaved for 10 min at 120° C. A saturated solution of $NaHCO_3$ was added to the reaction mixture and the precipitate formed was filtered and dried. The resulting crude product was purified by flash chromatography over silica gel using DCM/MeOH (95:5) as eluent to yield after evaporation N-(2,5-difluorophenyl)-6-(1H-pyrazol-4-yl)pyridin-2-amine (0.11 mmol, 30 mg, 43%) as a brown solid.

M.p.: 198-199° C.;

LC (Zorbax SB-$C_{18}$, 3.5 nm, 4.6×50 mm Column): RT=2.16 min; MS m/z ES$^+$=273;

$^1$H NMR (300 MHz, DMSO) 8.94 (1H, s), 8.66-8.58 (1H, m), 8.21 (1H, s), 7.98 (1H, s), 7.63-7.58 (1H, m), 7.30-7.22 (1H, m), 7.19-7.16 (1H, d), 6.95-6.93 (1H, d), 6.77-6.70 (1H, m).

The compounds in the following Tables have been synthezised according to the same methods as previous examples 1 to 8, as denoted in the column denoted as "Exp. nr". The compounds denoted with the asterisk have been exemplified in the Examples.

TABLE 1

Compounds prepared according to the Examples.

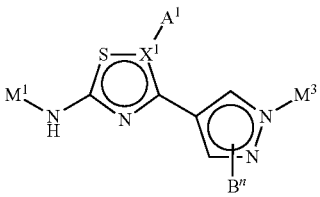

| Co.nr. | Exp nr. | M$^1$ | | M$^3$ B$^n$ |
|---|---|---|---|---|
| 1-1 | 1 | 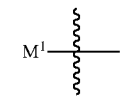 | 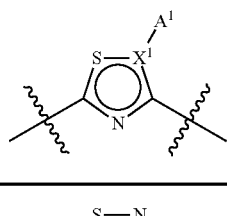 | 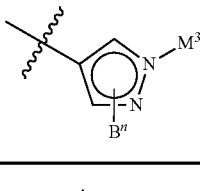 |
| 1-2* | 13 | 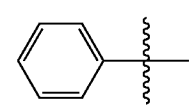 [SMILES: *c1ccccc1] | 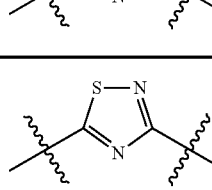 | 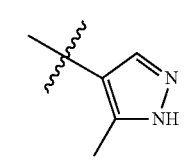 [SMILES: *c1cn[nH]c1C] |

TABLE 1-continued

Compounds prepared according to the Examples.

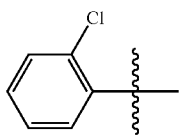 [SMILES: *c1ccccc1F]

| Co.nr. | Exp nr. | M¹ | (thiadiazole/thiazole) | (pyrazole) |
|---|---|---|---|---|
| 1-3* | 1 | 2-chlorophenyl | 1,3,4-thiadiazole-2,5-diyl | 3-methyl-1H-pyrazol-4-yl |
| 1-4 | 3 | 2-fluorophenyl | 1,3,4-thiadiazole-2,5-diyl | 3-methyl-1H-pyrazol-4-yl |
| 1-5* | 3 | pyridin-2-yl | 1,3,4-thiadiazole-2,5-diyl | 3-methyl-1H-pyrazol-4-yl |
| 1-6 | 3 | phenyl | 1,3,4-thiadiazole-2,5-diyl | 1H-pyrazol-4-yl |
| 1-7 | 4 | phenyl | thiazole-2,4-diyl | 3-methyl-1H-pyrazol-4-yl |
| 1-8 | 2 | phenyl | 1,3,4-thiadiazole-2,5-diyl | 3-propyl-1H-pyrazol-4-yl |
| 1-9* | 2 | pyridin-2-yl | 1,3,4-thiadiazole-2,5-diyl | 3-propyl-1H-pyrazol-4-yl |

TABLE 1-continued

Compounds prepared according to the Examples.

| Co.nr. | Exp nr. | M¹ | (thiadiazole/thiazole core) | (pyrazole with M³/Bⁿ) |
|---|---|---|---|---|
| 1-10 | 2 | 2-pyridyl | 1,3,4-thiadiazole-2,5-diyl | 5-CF₃-pyrazol-4-yl (NH) |
| 1-11 | 4 | 2-pyridyl | thiazole-2,4-diyl | 5-methyl-pyrazol-4-yl (NH) |
| 1-12* | 4 | 2-pyridyl | thiazole-2,4-diyl | 5-CF₃-pyrazol-4-yl (NH) |
| 1-13 | 4 | 2-pyridyl | thiazole-2,4-diyl | 3-isopropyl-pyrazol-4-yl (NH) |
| 1-14 | 4 | 2,6-difluorophenyl | thiazole-2,4-diyl | 5-methyl-pyrazol-4-yl (NH) |
| 1-15 | 5 | 2-pyridyl | 5-methyl-thiazole-2,4-diyl | 5-methyl-pyrazol-4-yl (NH) |
| 1-16* | 5 | 2-pyridyl | 5-methyl-thiazole-2,4-diyl | pyrazol-4-yl (NH) |

TABLE 1-continued
Compounds prepared according to the Examples.
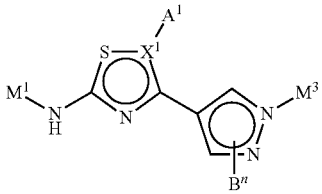

TABLE 1-continued

Compounds prepared according to the Examples.

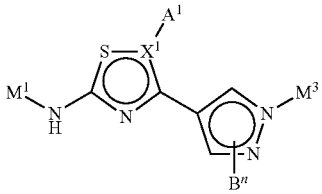

| Co.nr. | Exp nr. | M¹ | ⟨S—X¹(A¹)=N⟩ | pyrazole-M³/Bⁿ |
|---|---|---|---|---|
| 1-24 | 5 | 5-F-pyridin-2-yl | 4-methylthiazol-2,5-diyl | 1H-pyrazol-4-yl |
| 1-25 | 4 | pyridin-2-yl | thiazol-2,4-diyl | 1H-pyrazol-4-yl |
| 1-26* | 14 | pyridin-2-yl | 4-methylthiazol-2,5-diyl | 1-isobutyryl-pyrazol-4-yl |
| 1-27* | 15 | pyridin-2-yl | 4-methylthiazol-2,5-diyl | 1-carbamoyl-pyrazol-4-yl |
| 1-28 | 14 | pyridin-2-yl | 4-methylthiazol-2,5-diyl | 1-cyclohexanecarbonyl-pyrazol-4-yl |
| 1-29 | 5 | cyclohexyl | 4-methylthiazol-2,5-diyl | 1H-pyrazol-4-yl |
| 1-30 | 14 | 6-methyl-pyridin-2-yl | 4-methylthiazol-2,5-diyl | 1-isobutyryl-pyrazol-4-yl |

TABLE 1-continued

Compounds prepared according to the Examples.

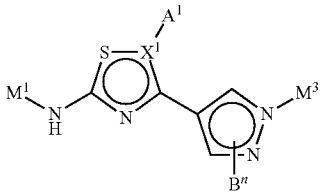

| Co.nr. | Exp nr. | M¹ | (thiazole with A¹, X¹) | (pyrazole with M³, Bⁿ) |
|---|---|---|---|---|
| 1-31 | 5 | 6-Cl-pyridin-2-yl | 4-methyl-thiazole-2,5-diyl | 1H-pyrazol-4-yl |
| 1-32* | 6 | pyridin-2-yl | 4-Cl-thiazole-2,5-diyl | 1H-pyrazol-4-yl |
| 1-33 | 5 | 6-F-pyridin-2-yl | 4-methyl-thiazole-2,5-diyl | 1H-pyrazol-4-yl |
| 1-34* | 16 | pyridin-2-yl | 4-methyl-thiazole-2,5-diyl | 1-(piperidine-1-carbonyl)-pyrazol-4-yl |
| 1-35 | 2 | pyridin-2-yl | 1,3,4-thiadiazole-2,5-diyl | 1H-pyrazol-4-yl |
| 1-36 | 14 | pyridin-2-yl | 1,3,4-thiadiazole-2,5-diyl | 1-isobutyryl-pyrazol-4-yl |
| 1-37 | 5 | cyclopentyl | 4-methyl-thiazole-2,5-diyl | 1H-pyrazol-4-yl |
| 1-38 | 2 | 6-methyl-pyridin-2-yl | 1,3,4-thiadiazole-2,5-diyl | 1H-pyrazol-4-yl |

TABLE 1-continued
Compounds prepared according to the Examples.
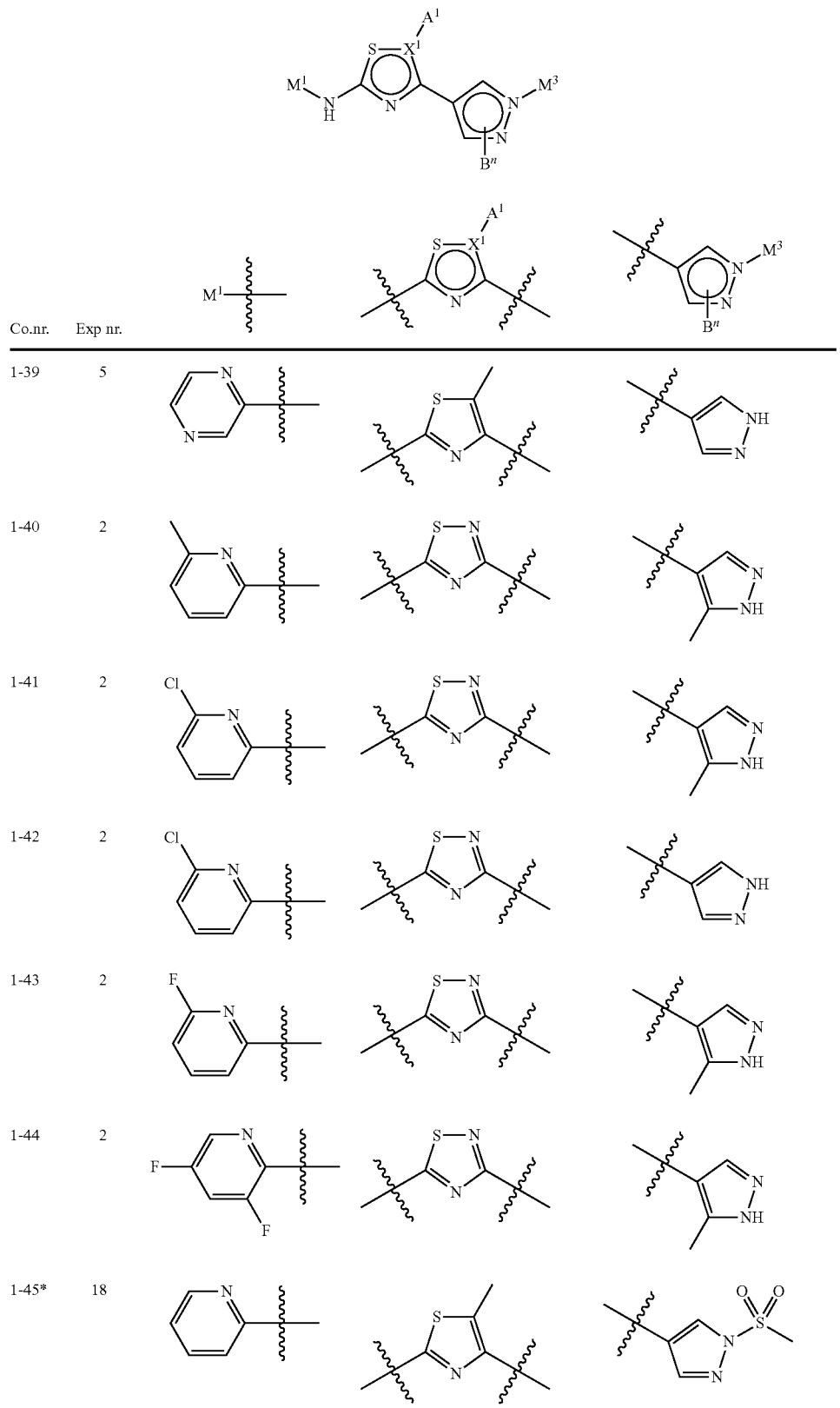

TABLE 1-continued
Compounds prepared according to the Examples.
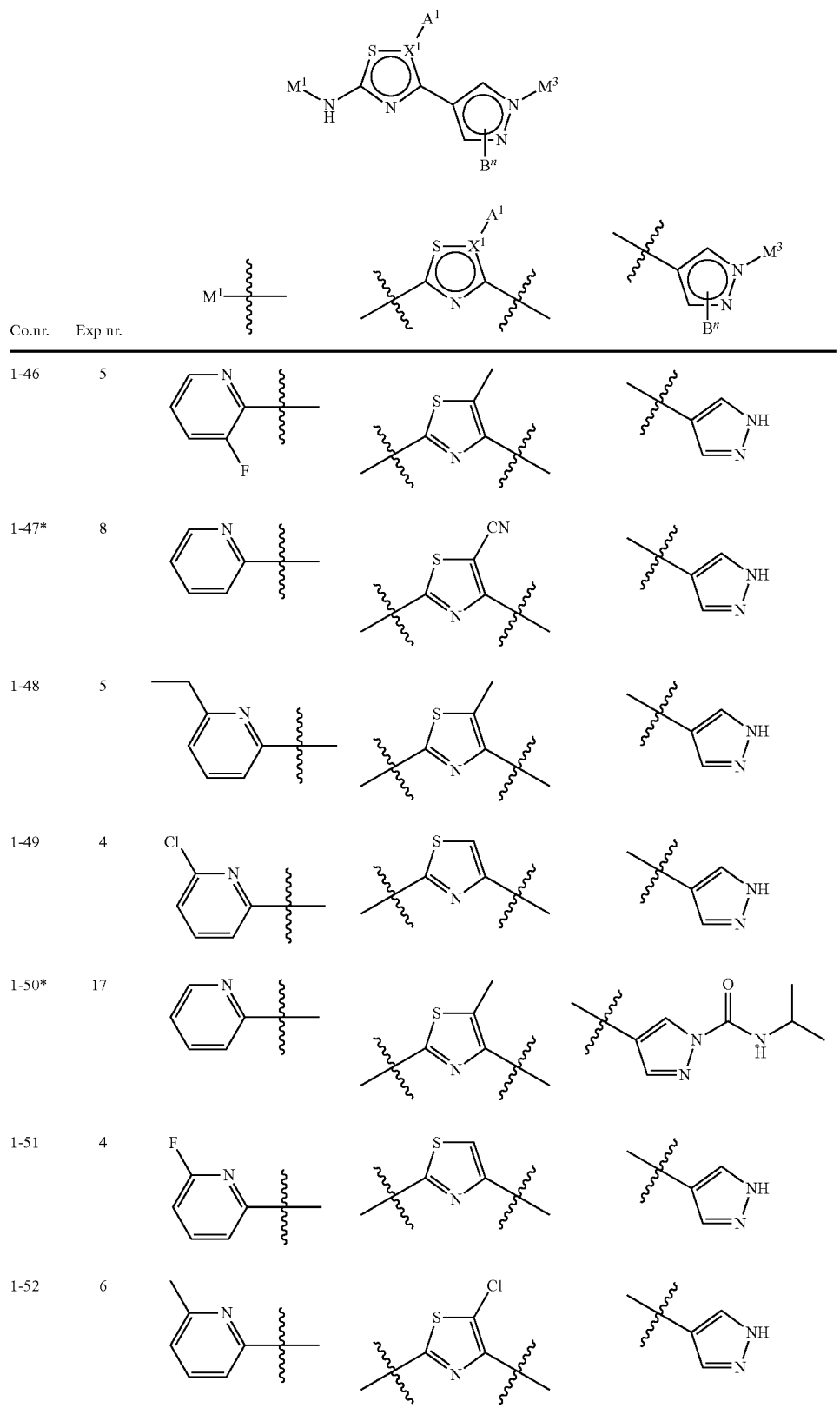

TABLE 1-continued

Compounds prepared according to the Examples.

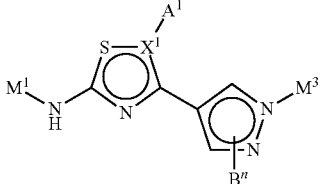

| Co.nr. | Exp nr. | M¹ | (thiazole with A¹, X¹) | (pyrazole with M³, Bⁿ) |
|---|---|---|---|---|
| 1-53 | 4 | 6-methylpyridin-2-yl | thiazole | 1H-pyrazol-4-yl |
| 1-54* | 9 | pyridin-2-yl | thiazole, A¹=CF₃ | 1H-pyrazol-4-yl |
| 1-55* | 10 | pyridin-2-yl | thiazole, A¹=Ph | 1H-pyrazol-4-yl |
| 1-56* | 7 | pyridin-2-yl | thiazole, A¹=F | 1H-pyrazol-4-yl |
| 1-57* | 11 | pyridin-2-yl | thiazole, A¹=CH₂OH | 1H-pyrazol-4-yl |
| 1-58 | 5 | 6-methoxypyridin-2-yl | thiazole, A¹=Me | 1H-pyrazol-4-yl |
| 1-59 | 17 | pyridin-2-yl | thiazole, A¹=Me | pyrazol-N-C(O)NHcyclopropyl |

TABLE 1-continued
Compounds prepared according to the Examples.
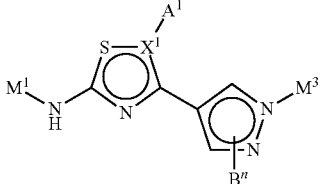
| Co.nr. | Exp nr. | M¹ | | |
|---|---|---|---|---|
| 1-60* | 12 | 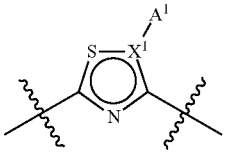 | 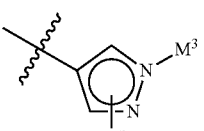 | 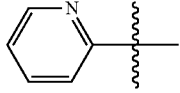 [SMILES: *c1ccccn1] |
| 1-61* | 12 | 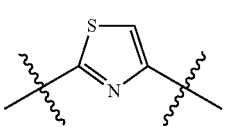 | 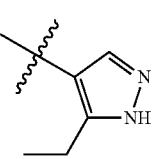 [SMILES: *c1cn[nH]c1CC] | 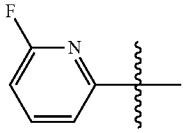 [SMILES: *c1cccc(F)n1] |
| 1-62 | 15 | 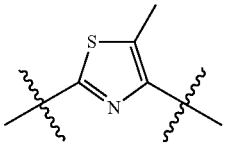 [SMILES: *c1nc(*)c(C)s1] | 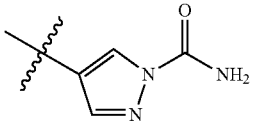 [SMILES: *c1cnn(C(N)=O)c1] | 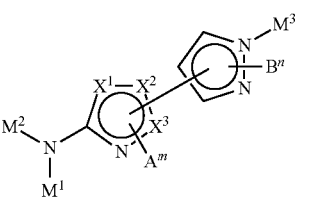 |
TABLE 2
Compounds prepared according to the Examples.
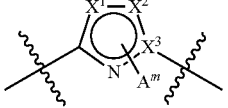
| Co.nr. | Exp nr. | | | |
|---|---|---|---|---|
| 2-1* | 19 | 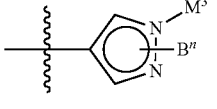 | | |

Physico-Chemical Data
LCMS-Methods:
LCMS were recorded on a Waters Micromass ZQ 2996 system by the following conditions:

Method 1

Reversed phase HPLC was carried out on an Zorbax SB-C18 cartridge (3.5 μm, 4.6×50 mm) from Agilent, with a flow rate of 1 mL/min. The gradient conditions used are: 95% A (water+0.5% of formic acid), 5% B (acetonitrile+0.5% of formic acid) to 100% B at 5.0 minutes, kept till 6.0 minutes and equilibrated to initial conditions at 6.5 minutes until 7.5 minutes. Injection volume 5-20 μL. ES MS detector was used, acquiring both in positive and negative ionization modes. Cone voltage was 30 V for both positive and negative ionization modes.

Method 2

Reversed phase HPLC was carried out on an Zorbax SB-C18 cartridge (1.8 μm, 4.6×30 mm) from Agilent, with a flow rate of 1.5 mL/min. The gradient conditions used are: 90% A (water+0.05% of formic acid), 10% B (acetonitrile+0.05% of formic acid) to 100% B at 3.5 minutes, kept till 3.7 minutes and equilibrated to initial conditions at 3.8 minutes until 4.5 minutes. Injection volume 5-20 μL. ES MS detector was used, acquiring both in positive and negative ionization modes. Cone voltage was 30 V for both positive and negative ionization modes.

All mass spectra were taken under electrospray ionisation (ESI) methods.

TABLE 3

Physico-chemical data for some compounds (nd = not determined).

| Co. Nr | Melting point (° C.) | MW (theor) | [MH$^+$] | RT (min) | LCMS Method | Physical form |
|---|---|---|---|---|---|---|
| 1-1 | nd | 257.314 | 258 | 1.97 | Method 2 | White solid |
| 1-2 | 204-208 | 299.351 | 300 | 4.41 | Method 1 | White solid |
| 1-3 | 180-182 | 291.759 | 292 | 2.18 | Method 2 | White solid |
| 1-4 | nd | 275.305 | 276 | 2.02 | Method 2 | White solid |
| 1-5 | >280 | 258.302 | 259 | 1.75 | Method 2 | White solid |
| 1-6 | 192 | 243.288 | 244 | 1.77 | Method 2 | White solid |
| 1-7 | 200-202 | 256.326 | 257 | 2.02 | Method 2 | Light grey solid |
| 1-8 | 170-172 | 285.367 | 286 | 2.32 | Method 2 | White solid |
| 1-9 | 248-250 | 286.355 | 287 | 2.15 | Method 2 | White solid |
| 1-10 | >260 | 312.274 | 313 | 2.13 | Method 2 | White solid |
| 1-11 | 255-257 | 257.314 | 258 | 1.50 | Method 2 | White solid |
| 1-12 | 250 | 311.286 | 312 | 2.07 | Method 2 | White solid |
| 1-13 | 195 | 285.367 | 286 | 1.75 | Method 2 | Yellow solid |
| 1-14 | nd | 292.31 | 293 | 1.92 | Method 2 | Yellow solid |
| 1-15 | 218 | 271.34 | 272 | 1.50 | Method 2 | Beige solid |
| 1-16 | 291-294 | 257.31 | 258 | 1.47 | Method 2 | White solid |
| 1-17 | 196-199 | 292.31 | 293 | 2.20 | Method 2 | Orange solid |
| 1-18 | 306 | 271.34 | 272 | 1.56 | Method 2 | White solid |
| 1-19 | 274 | 271.34 | 272 | 1.45 | Method 2 | Beige solid |
| 1-20 | >300 | 293.3 | 294 | 2.06 | Method 2 | Beige solid |
| 1-21 | 276-278 | 271.34 | 272 | 1.56 | Method 2 | Beige solid |
| 1-22 | 243-246 | 271.34 | 272 | 1.65 | Method 2 | White solid |
| 1-23 | 295 (dec.) | 271.34 | 272 | 1.55 | Method 2 | Yellow solid |
| 1-24 | 320 | 275.30 | 276 | 1.89 | Method 2 | Beige solid |
| 1-25 | 261-262 | 243.29 | 244 | 1.42 | Method 2 | White solid |
| 1-26 | 168 | 327.40 | 328 | 2.76 | Method 2 | Beige solid |
| 1-27 | 294-296 | 300.34 | 301 | 1.71 | Method 2 | White solid |
| 1-28 | 140-144 | 367.47 | 368 | 3.25 | Method 2 | White solid |
| 1-29 | 205-207 | 262.37 | 263.3 | 1.39 | Method 2 | Off-white solid |
| 1-30 | 159-160 | 341.43 | 342 | 3.00 | Method 2 | Beige solid |
| 1-31 | 290 (dec.) | 291.76 | 292 | 2.17 | Method 2 | White solid |
| 1-32 | 282-285 | 277.73 | 278 | 2.17 | Method 2 | Beige solid |
| 1-33 | 290 (dec) | 275.3 | 276 | 1.99 | Method 2 | Beige solid |
| 1-34 | 137-138 | 368.46 | 369 | 2.42 | Method 2 | White solid |
| 1-35 | 300 (dec.) | 244.28 | 245 | 1.57 | Method 2 | Beige solid |
| 1-36 | 248-254 | 314.37 | 315 | 2.61 | Method 2 | Beige solid |
| 1-37 | 197 | 248.35 | 249 | 1.26 | Method 2 | Beige solid |
| 1-38 | 276 | 258.30 | 259 | 1.75 | Method 2 | Beige solid |
| 1-39 | 252 | 258.30 | 259 | 1.63 | Method 2 | Beige solid |
| 1-40 | >300 | 272.33 | 273 | 1.94 | Method 2 | Brown solid |
| 1-41 | 285 (dec) | 292.75 | 293 | 2.02 | Method 2 | Brown solid |
| 1-42 | 317-319 | 278.72 | 279 | 1.84 | Method 2 | Brown solid |
| 1-43 | >300 | 276.29 | 277 | 1.88 | Method 2 | Yellow solid |
| 1-44 | >300 | 294.28 | 295 | 1.88 | Method 2 | Beige solid |
| 1-45 | 193 | 335.40 | 336 | 2.06 | Method 2 | White solid |
| 1-46 | 300 (dec.) | 275.30 | 276 | 1.94 | Method 2 | Beige solid |
| 1-47 | 250 (dec.) | 268.30 | 269 | 1.99 | Method 2 | Beige solid |
| 1-48 | 276-278 | 285.37 | 286 | 1.85 | Method 2 | Beige solid |
| 1-49 | 295 (dec.) | 277.73 | 278 | 2.06 | Method 2 | Beige solid |
| 1-50 | 297-298 | 342.42 | 343 | 2.43 | Method 2 | White solid |
| 1-51 | 281-285 | 261.28 | 262 | 1.90 | Method 2 | Beige solid |
| 1-52 | 278-282 | 291.76 | 292 | 2.38 | Method 2 | Beige solid |
| 1-53 | 259-260 | 257.31 | 258 | 1.49 | Method 2 | White solid |
| 1-54 | 250 (dec.) | 311.29 | 312 | 2.34 | Method 2 | Beige solid |
| 1-55 | 266-267 | 319.38 | 320 | 2.31 | Method 2 | White solid |
| 1-56 | nd | 261.28 | 262 | 1.98 | Method 2 | Brown solid |
| 1-57 | 250 (dec.) | 273.31 | 274 | 1.12 | Method 2 | White solid |
| 1-58 | nd | 287.34 | 288 | 2.11 | Method 2 | Brown solid |
| 1-59 | 270 (dec.) | 340.40 | 341 | 2.20 | Method 2 | White solid |
| 1-60 | 211-213 | 283.35 | 284 | 1.79 | Method 2 | Beige solid |
| 1-61 | 196-198 | 271.34 | 272 | 1.68 | Method 2 | Beige solid |
| 1-62 | 230 (dec.) | 318.33 | 319 | 2.19 | Method 2 | White solid |
| 2-1 | 198-199 | 272.25 | 273 | 2.16 | Method 2 | Brown solid |

TABLE 4

NMR-data

| Co. Nr | NMR-data |
|---|---|
| 1-1 | $^1$H NMR (300 MHz, DMSO) 11.02 (1H, s), 8.50-8.15 (1H, m), 7.95 (1H, s), 7.60 (2H, d), 7.50-7.30 (1H, m), 7.15-7.00 (1H, m), 2.61 (3H, s) |
| 1-2 | $^1$H NMR (300 MHz, DMSO) 11.05 (1H, s), 8.71 (1H, s), 7.70-7.55 (2H, m), 7.50-7.32 (2H, m), 7.15-7.05 (1H, m), 2.72 (3H, s), 2.61 (3H, s) |
| 1-3 | $^1$H NMR (300 MHz, DMSO) 12.95-12.70 (1H, br s), 10.45 (1H, s), 8.50 (1H, d), 8.10-7.80 (1H, m), 7.55 (1H, d), 7.50-7.38 (1H, m), 7.22-7.10 (1H, m), 2.61 (3H, s) |
| 1-4 | $^1$H NMR (300 MHz, MeOD) 8.40-8.28 (1H, m), 7.95 (1H, s), 7.20-6.92 (3H, m), 2.55 (3H, s) |
| 1-5 | $^1$H NMR (300 MHz, MeOD) 8.32 (1H, d), 7.92 (1H, s), 7.72-7.60 (1H, m), 7.02 (1H, d), 6.98-6.85 (1H, m), 2.55 (3H, s) |
| 1-6 | $^1$H NMR (300 MHz, DMSO) 11.02 (1H, s), 8.50-8.15 (1H, m), 8.15-7.80 (1H, m), 7.60 (2H, d), 7.50-7.30 (2H, m), 7.15-7.00 (1H, m) |
| 1-7 | $^1$H NMR (300 MHz, DMSO) 10.18 (1H, s), 7.85 (1H, s), 7.68 (2H, dd), 7.40-7.22 (2H, m), 6.98-6.88 (1H, m), 6.75 (1H, s), 2.45 (3H, s) |
| 1-8 | $^1$H NMR (300 MHz, DMSO) 10.92 (1H, s), 8.02-7.80 (1H, m), 7.65 (2H, d), 7.48-7.30 (2H, m), 7.12-7.00 (1H, m), 3.12-2.85 (2H, m), 1.80-1.60 (2H, m), 0.95 (3H, t) |
| 1-9 | $^1$H NMR (300 MHz, DMSO) 12.95-12.65 (1H, br s), 12.15 (1H, s), 8.42 (1H, d), 8.10-7.75 (2H, m), 7.18 (1H, d), 7.12-7.00 (1H, m), 3.12-2.90 (2H, m), 1.80-1.60 (2H, m), 0.95 (3H, t) |
| 1-10 | $^1$H NMR (300 MHz, DMSO) 12.60-11.90 (1H, br s), 8.45 (2H, s), 7.90-7.72 (1H, m), 7.22 (1H, d), 7.12-6.98 (1H, m) |

TABLE 4-continued

NMR-data

| Co. Nr | NMR-data |
|---|---|
| 1-11 | $^1$H NMR (300 MHz, DMSO) 12.70-12.40 (1H, br s), 11.24 (1H, s), 8.22 (1H, d), 7.85-7.55 (2H, m), 7.03 (1H, d), 6.90-6.80 (1H, m), 6.75 (s, 1H), 2.42 (3H, s) |
| 1-12 | $^1$H NMR (300 MHz, DMSO) δ 11.32 (1H, s), 8.32 (1H, dd), 8.19 (1H, s), 7.75-7.64 (1H, m), 7.12 (1H, d), 6.98-6.85 (2H, m) |
| 1-13 | $^1$H NMR (300 MHz, DMSO) δ 11.22 (1H, s), 8.30 (1H, d), 7.75-7.62 (2H, m), 7.13 (1H, d), 6.95-6.85 (1H, m) 6.82 (1H, s), 2.32-2.25 (1H, m), 1.28 (6H, d) |
| 1-14 | $^1$H NMR (300 MHz, DMSO) 7.84 (1H, s), 7.22-7.14 (2H, m), 7.04-6.98 (2H, m), 6.51 (1H, s), 2.49 (3H, s) |
| 1-15 | $^1$H NMR (300 MHz, DMSO) 12.70-12.50 (1H, br s), 11.00 (1H, s), 8.25 (1H, dd), 7.69-7.63 (2H, m), 7.05 (1H, d), 6.87 (1H, m), 2.35 (3H, s), 2.31 (3H, s) |
| 1-16 | $^1$H NMR (300 MHz, DMSO) 12.93 (1H, s), 11.15 (1H, s), 8.25 (1H, dd), 8.00-7.75 (2H, m), 7.70-7.62 (1H, m), 7.01 (1H, d), 6.90-6.80 (1H, m), 2.39 (3H, s) |
| 1-17 | $^1$H NMR (300 MHz, DMSO) 12.70-12.50 (1H, br s), 10.31 (1H, s), 8.68-8.50 (1 H, m), 7.85-7.70 (1H, m), 7.35-7.22 (2H, m), 6.85-6.70 (1H, m), 2.49 (3H, s) |
| 1-18 | $^1$H NMR (300 MHz, DMSO) 12.95 (1H, s), 11.09 (1H, s), 7.90 (2H, s), 7.57-7.52 (1H, m), 6.83-6.73 (2H, dd), 2.44 (3H, s), 2.40 (3H, s) |
| 1-19 | $^1$H NMR (300 MHz, DMSO) 12.95 (1H, s), 11.09 (1H, d), 7.94-7.80 (2H, m), 6.82 (1H, s), 6.74-6.72 (1H, d), 2.39 (3H, s), 2.26 (3H, s) |
| 1-20 | $^1$H NMR (300 MHz, DMSO) 12.4 (2H, s), 8.10 (1H, s), 7.90 (2H, s), 7.76-7.70 (1H, m), 2.38 (3H, s) |
| 1-21 | $^1$H NMR (300 MHz, DMSO) 12.75-12.40 (1H, br s), 11.22 (1H, s), 7.90-7.70 (1H, m), 7.65-7.50 (1H, m), 6.87 (1H, d), 6.82 (1H, s), 6.76 (1H, d), 2.45 (3H, s), 2.44 (3H, s) |
| 1-22 | $^1$H NMR (300 MHz, DMSO) 11.16 (1H, s), 8.28-8.26 (1H, m), 8.00-7.70 (2H, m), 7.70-7.62 (1H, m), 7.02 (1H, d), 6.91-6.85 (1H, m), 2.84 (2H, q), 1.25 (3H, t) |
| 1-23 | $^1$H NMR (300 MHz, DMSO) 12.70-12.45 (1H, br s), 11.22 (1H, s), 7.85-7.65 (1H, m), 7.62-7.49 (1H, m), 6.88 (1H, d), 6.82 (1H, s), 6.77 (1H, d), 2.50 (3H, s), 2.45 (3H, s) |
| 1-24 | $^1$H NMR (300 MHz, DMSO) 11.24 (1H, s), 8.26-8.25 (1H, d), 7.87 (2H, s), 7.71-7.64 (1H, m), 7.11-7.07 (1H, dd), 2.4 (3H, s) |
| 1-25 | $^1$H NMR (300 MHz, DMSO) 12.86 (1H, s), 11.33 (1H, s), 8.30-8.28 (1H, m), 8.02-7.81 (2H, m), 7.72-7.66 (1H, m), 7.08-7.05 (1H, m), 6.99 (1H, s), 6.93-6.89 (1H, m) |
| 1-26 | $^1$H NMR (300 MHz, DMSO) 11.23 (1H, s), 8.47 (1H, s), 8.26 (1H, dd), 8.19 (1H, s), 7.72-7.64 (1H, m), 7.03 (1H, d), 6.93-6.87 (1H, m), 3.88-3.77 (1H, m), 2.47 (3H, s), 1.24 (6H, d) |
| 1-27 | $^1$H NMR (300 MHz, DMSO) 11.21 (1H, s), 8.39 (1H, s), 8.26 (1H, d), 8.03 (1H, s), 7.91 (2H, d), 7.72-7.64 (1H, m), 7.02 (1H, d), 6.93-6.87 (1H, m), 2.44 (3H, s) |
| 1-28 | $^1$H NMR (300 MHz, DMSO) 11.26 (1H, s), 8.46 (1H, s), 8.26 (1H, d), 8.19 (1H, s), 7.72-7.64 (1H, m), 7.03 (1H, d), 6.90 (1H, dd), 3.64-3.53 (1H, m), 2.46 (3H, s), 1.95 (2H, d), 1.81-1.29 (8H, m) |
| 1-29 | $^1$H NMR (300 MHz, MeOD) 7.90-7.70 (2H, m), 3.45-3.30 (1H, m), 2.32 (3H, s) 2.15-1.92 (2H, m), 1.88-1.70 (2H, m), 1.72-1.58 (1H, m), 1.50-1.10 (5H, m) |
| 1-30 | $^1$H NMR (300 MHz, DMSO) 11.18 (1H, s), 8.47 (1H, s), 8.20 (1H, s), 7.60-7.52 (1H, m), 6.81 (1H, d), 6.76 (1H, d), 3.88-3.77 (1H, m), 2.46 (3H, s), 2.45 (3H, s), 1.24 (6H, d) |
| 1-31 | $^1$H NMR (300 MHz, DMSO) 11.46 (1H, s), 8.15-7.75 (2H, m), 7.75-7.65 (1H, m), 7.00 (1H, d), 6.95 (1H, d), 2.42 (3H, s) |
| 1-32 | $^1$H NMR (300 MHz, DMSO) 11.62 (1H, s), 8.30 (1H, d), 8.20-8.11 (1H, m), 7.99-7.90 (1H, m), 7.77-7.69 (1H, m), 7.04 (1H, d), 6.99-6.93 (1H, m) |
| 1-33 | $^1$H NMR (300 MHz, DMSO) 11.44 (1H, s), 8.05-7.85 (2H, m), 7.90-7.70 (2H, m), 6.95 (1H, dd), 6.55 (1H, dd), 2.42 (3H, s) |
| 1-34 | $^1$H NMR (300 MHz, DMSO) 11.23 (1H, s), 8.32 (1H, s), 8.26 (1H, dd), 8.04 (1H, s), 7.71-7.64 (1H, m), 7.03 (1H, d), 6.89 (1H, t), 3.80-3.50 (4H, m), 2.44 (3H, s), 1.70-1.50 (6H, s) |
| 1-35 | $^1$H NMR (300 MHz, DMSO) 12.26 (1H, s), 8.43 (1H, d), 8.25-7.90 (2H, m), 7.86-7.78 (1H, m), 7.14 (1H, d), 7.09-7.02 (1H, m) |
| 1-36 | $^1$H NMR (300 MHz, DMSO) 12.39 (1H, s), 8.66 (1H, s), 8.44 (1H, d), 8.35 (1H, s), 7.88-7.80 (1H, m), 7.17 (1H, d), 7.12-7.05 (1H, m), 3.87-3.75 (1H, m), 1.24 (6H, d) |
| 1-37 | $^1$H NMR (300 MHz, DMSO) 12.86 (1H, s), 8.00-7.52 (2H, m), 7.30 (1H, d), 3.85-3.70 (1H, m), 2.28 (3H, s), 1.95-1.75 (2H, m), 1.75-1.30 (6H, m) |
| 1-38 | $^1$H NMR (300 MHz, MeOD) 8.30-8.00 (2H, br s), 7.69-7.62 (1H, m), 6.89 (2H, dd), 2.58 (3H, s) |
| 1-39 | $^1$H NMR (300 MHz, DMSO) 11.63 (1H, s), 8.43 (1H, d), 8.27 (1H, dd), 8.08 (1H, d), 7.99 (1H, s), 7.80 (1H, s), 2.43 (3H, s) |
| 1-40 | $^1$H NMR (300 MHz, DMSO) 12.11 (1H, s), 7.88-7.85 (1H, br s), 7.73-7.68 (1H, m), 6.97-6.90 (2H, dd), 2.57 (3H, s), 2.53 (3H, s) |
| 1-41 | $^1$H NMR (300 MHz, DMSO) 12.90-12.40 (1H, br s), 8.00-7.80 (1H, m), 7.69-7.65 (1H, m), 6.96-6.83 (2H, m), 2.56 (3H, s) |
| 1-42 | $^1$H NMR (300 MHz, DMSO) 12.54 (1H, s), 8.24 (1H, s), 7.97 (1H, s), 7.90-7.82 (1H, m), 7.13 (2H, dd) |
| 1-43 | $^1$H NMR (300 MHz, DMSO) 12.95-12.70 (1H, br s), 12.44 (1H, s), 8.03-7.80 (2H, m), 7.08 (1H, d), 6.80 (1H, d), 2.59 (3H, s) |
| 1-44 | $^1$H NMR (300 MHz, DMSO) 12.95-12.80 (1H, br s), 12.60-12.35 (1H, br s), 8.40-8.39 (1H, m), 8.12-8.05 (1H, m), 8.05-7.80 (1H, br s), 2.58 (3H, s) |
| 1-45 | $^1$H NMR (300 MHz, DMSO) 11.25 (1H, s), 8.36 (1H, s), 8.28-8.21 (2H, m), 7.72-7.64 (1H, m), 7.03 (1H, d), 6.93-6.86 (1H, m), 3.60 (3H, s) |
| 1-46 | $^1$H NMR (300 MHz, DMSO) 8.10 (1H, d), 8.05-7.80 (2H, m), 7.68-7.50 (1H, m), 6.98-6.82 (1H, m), 2.42 (3H, s) |
| 1-47 | $^1$H NMR (300 MHz, DMSO) 12.34 (1H, s), 8.39 (1H, dd), 8.35-8.20 (1H, br s), 8.10-7.95 (1H, br s), 7.86-7.78 (1H, m), 7.14 (1H, d), 7.08 (1H, dd) |
| 1-48 | $^1$H NMR (300 MHz, DMSO) 12.99-12.90 (1H, br s), 11.10 (1H, s), 8.05-7.70 (2H, m), 7.62-7.50 (1H, m), 6.82 (1H, d), 6.75 (1H, d), 2.74 (2H, q), 2.42 (3H, s), 1.32 (3H, t) |
| 1-49 | $^1$H NMR (300 MHz, MeOD) 8.00-7.90 (2H, br s), 7.69-7.61 (1H, m), 6.98-6.90 (3H, m) |
| 1-50 | $^1$H NMR (300 MHz, DMSO) 11.21 (1H, s), 8.40 (1H, s), 8.33 (1H, d), 8.28 (1H, dd), 8.04 (1H, s), 7.72-7.64 (1H, m), 7.02 (1H, d), 6.93-6.87 (1H, m), 4.05-3.96 (1H, m), 2.44 (3H, s), 1.22 (6H, d) |
| 1-51 | $^1$H NMR (300 MHz, DMSO) 11.66 (1H, s), 8.01-7.81 (3H, m), 7.08 (1H, s), 6.99 (1H, dd), 6.61 (1H, dd) |
| 1-52 | $^1$H NMR (300 MHz, DMSO) 11.56 (1H, s), 8.25-7.85 (2H, m), 7.65-7.57 (1H, m), 6.82 (2H, t), 2.47 (3H, s) |
| 1-53 | $^1$H NMR (300 MHz, DMSO) 11.31 (1H, s), 8.05-7.75 (2H, m), 7.61-7.53 (1H, m), 6.98 (1H, s), 6.84 (1H, d), 6.76 (1H, d), 2.45 (3H, s) |
| 1-54 | $^1$H NMR (300 MHz, DMSO) 11.96 (1H, s), 8.38 (1H, d), 8.05-7.85 (2H, br s), 7.82-7.74 (1H, m), 7.12 (1H, d), 7.05-6.99 (1H, m) |
| 1-55 | $^1$H NMR (300 MHz, DMSO) 11.43 (1H, s), 8.28 (1H, d), 7.71 (1H, dd), 7.45-7.39 (7H, m), 7.07 (1H, d), 6.91 (1H, dd) |
| 1-56 | $^1$H NMR (300 MHz, DMSO) 11.40 (1H, s), 8.27 (1H, s), 8.05-7.85 (1H, br s), 7.85-7.65 (1H, br s), 7.78-7.65 (1H, m), 7.01 (1H, d), 6.96-6.90 (1H, m) |
| 1-57 | $^1$H NMR (300 MHz, DMSO) 11.24 (1H, s), 8.28 (1H, dd), 8.05-7.90 (1H, br s), 7.85-7.70 (1H, br s), 7.69-7.64 (1H, m), 7.03 (1H, d), 6.93-6.86 (1H, m), 5.39 (1H, t), 4.64 (2H, t) |
| 1-58 | $^1$H NMR (300 MHz, DMSO) 11.18 (1H, s), 7.92-7.82 (2H, m), 7.62-7.52 (1H, m), 6.55 (1H, d), 6.28 (1H, d), 4.02 (3H, s), 2.42 (3H, s) |
| 1-59 | $^1$H NMR (300 MHz, DMSO) 11.21 (1H, s), 8.63 (1H, d), 8.39 (1H, d), 8.28-8.22 (1H, m), 8.01 (1H, d), 7.72-7.64 (1H, m), 7.02 (1H, d), 6.93-6.87 (1H, m), 2.85-2.72 (1H, m), 2.44 (3H, s), 0.75-0.61 (4H, m) |
| 1-60 | $^1$H NMR (300 MHz, DMSO) 12.42 (1H, s), 11.29 (1H, s), 8.28 (1H, d), 7.90-7.78 (1H, m), 7.75-7.60 (1H, m), 7.06 (1H, d), 6.96 (1H, s), 6.99-6.82 (1H, m), 2.45-2.22 (1H, m), 1.10-0.70 (4H, m) |

TABLE 4-continued

NMR-data

| Co. Nr | NMR-data |
|---|---|
| 1-61 | $^1$H NMR (300 MHz, DMSO) 12.70-12.50 (1H, s), 11.24 (1H, s), 8.29 (1H, d), 7.90-7.62 (2H, m), 7.10 (1H, d), 6.98-6.85 (1H, m), 6.83 (1H, s), 3.05-2.75 (2H, m), 1.23 (3H, t) |
| 1-62 | $^1$H NMR (300 MHz, DMSO) 11.50 (1H, s), 8.41 (1H, s), 8.03 (1H, s), 7.95-7.79 (3H, m), 6.97 (1H, dd), 6.60 (1H, dd), 2.49 (3H, s) |
| 2-1 | $^1$H NMR (300 MHz, DMSO) 8.94 (1H, s), 8.66-8.58 (1H, m), 8.21 (1H, s), 7.98 (1H, s), 7.63-7.58 (1H, m), 7.30-7.22 (1H, m), 7.19-7.16 (1H, d), 6.95-6.93 (1H, d), 6.77-6.70 (1H, m) |

Pharmacology

The compounds provided in the present invention are positive allosteric modulators of mGluR4. As such, these compounds do not appear to bind to the orthosteric glutamate recognition site, and do not activate the mGluR4 by themselves. Instead, the response of mGluR4 to a concentration of glutamate or mGluR4 agonist is increased when compounds of Formula I to III are present. Compounds of Formula I to III are expected to have their effect at mGluR4 by virtue of their ability to enhance the function of the receptor.

mGluR4 Assay on HEK-Expressing Human mGluR4

The compounds of the present invention are positive allosteric modulators of mGluR4 receptor. Their activity was examined on recombinant human mGluR4a receptors by detecting changes in intracellular $Ca^{2+}$ concentration, using the fluorescent $Ca^{2+}$-sensitive dye Fluo-4-(AM) and a Fluorometric Imaging Plate Reader (FLIPR, Molecular Devices, Sunnyvale, Calif.)

Transfection and Cell Culture

The cDNA encoding the human metabotropic glutamate receptor (hmGluR4), (accession number NM_000841.1, NCBI Nucleotide database browser), was subcloned into an expression vector containing also the hygromycin resistance gene. In parallel, the cDNA encoding a G protein allowing redirection of the activation signal to intracellular calcium flux was subcloned into a different expression vector containing also the puromycin resistance gene. Transfection of both these vectors into HEK293 cells with PolyFect reagent (Qiagen) according to supplier's protocol, and hygromycin and puromycin treatment allowed selection of antibiotic resistant cells which had integrated stably one or more copies of the plasmids. Positive cellular clones expressing hmGluR4 were identified in a functional assay measuring changes in calcium fluxes in in response to glutamate or selective known mGluR4 orthosteric agonists and antagonists.

HEK-293 cells expressing hmGluR4 were maintained in media containing DMEM, dialyzed Fetal Calf Serum (10%), Glutamax™ (2 mM), Penicillin (100 units/mL), Streptomycin (100 µg/mL), Geneticin (100 µg/mL) and Hygromycin-B (40 µg/mL) and puromycin (1 µg/mL) at 37° C./5% $CO_2$.

Fluorescent Cell Based-$Ca^{2+}$ Mobilization Assay

Human mGluR4 HEK-293 cells were plated out 24 hours prior to FLIPR$^{384}$ assay in black-walled, clear-bottomed, poly-L-ornithine-coated 384-well plates at a density of 25,000 cells/well in a glutamine/glutamate free DMEM medium containing foetal bovine serum (10%), penicillin (100 units/mL) and streptomycin (100 µg/mL) at 37 C/5% $CO_2$.

On the day of the assay, the medium was aspirated and the cells were loaded with a 3 µM solution of Fluo-4-AM (LuBioScience, Lucerne, Switzerland) in 0.03% pluronic acid. After 1 hour at 37 C/5% $CO_2$, the non incorporated dye was removed by washing cell plate with the assay buffer and the cells were left in the dark at room temperature for six hours before testing. All assays were performed in a pH 7.4 buffered-solution containing 20 mM HEPES, 143 mM NaCl, 6 mM KCl, 1 mM $MgSO_4$, 1 mM $CaCl_2$, 0.125 mM sulfapyrazone, 0.1% glucose.

After 10 s of basal fluorescence recording, various concentrations of the compounds of the invention were added to the cells. Changes in fluorescence levels were first monitored for 180 s in order to detect any agonist activity of the compounds. Then the cells were stimulated by an $EC_{25}$ glutamate concentration for an additional 110 s in order to measure enhancing activities of the compounds of the invention. $EC_{25}$ glutamate concentration is the concentration giving 25% of the maximal glutamate response.

The concentration-response curves of representative compounds of the present invention were generated using the Prism GraphPad software (Graph Pad Inc, San Diego, USA). The curves were fitted to a four-parameter logistic equation:

$$(Y=Bottom+(Top-Bottom)/(1+10^{((Log\ EC_{50}-X)*Hill\ Slope)})$$

allowing the determination of $EC_{50}$ values.

The Table 5 below represents the mean $EC_{50}$ obtained from at least three independent experiments of selected molecules performed in duplicate.

TABLE 5

Activity data for selected compounds

| Compound no. | $Ca^{2+}$ Flux* |
|---|---|
| 1-1 | + |
| 1-2 | + |
| 1-3 | + |
| 1-4 | ++ |
| 1-5 | + |
| 1-6 | + |
| 1-7 | + |
| 1-8 | + |
| 1-9 | + |
| 1-10 | ++ |
| 1-11 | +++ |
| 1-12 | ++ |
| 1-13 | + |
| 1-16 | +++ |
| 1-18 | +++ |
| 1-25 | +++ |
| 1-27 | +++ |
| 1-31 | +++ |
| 1-32 | +++ |
| 1-33 | +++ |
| 1-43 | +++ |
| 1-46 | +++ |
| 1-47 | +++ |
| 1-49 | +++ |
| 1-51 | +++ |
| 1-53 | +++ |
| 1-54 | ++ |
| 1-56 | +++ |
| 1-60 | +++ |
| 1-61 | +++ |

*Table legend: (+): 1 µM < $EC_{50}$ < 10 µM (++): 500 nM < $EC_{50}$ < 1 µM (+++): $EC_{50}$ < 500 nM The results shown in Table 5 demonstrate that the compounds described in the present invention are positive allosteric modulators of human mGluR4 receptors. These compounds do not have activity by themselves but they rather increase the functional activity and/or maximal efficacy of glutamate or mGluR4 agonist.

Thus, the positive allosteric modulators provided in the present invention are expected to increase the effectiveness of glutamate or mGluR4 agonists at mGluR4 receptor. Therefore, these positive allosteric modulators are expected to be useful for treatment of various neurological and psychiatric disorders associated with glutamate dysfunction described to be treated herein and others that can be treated by such positive allosteric modulators.

FORMULATION EXAMPLES

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced by the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 mL.

3. Injectable

A parenteral composition is prepared by stirring 1.5% by weight of active ingredient of the invention in 10% by volume propylene glycol and water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound according to the general Formula (I),

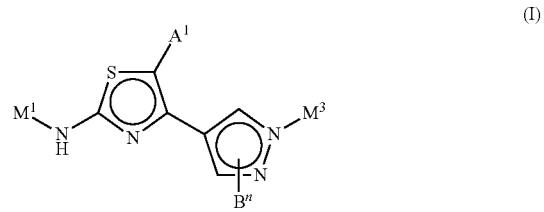

a pharmaceutically acceptable acid or base addition salt thereof, a stereochemically isomeric form thereof and an N-oxide form thereof, wherein:

$A^1$ radical is selected from the group of hydrogen, halogen, —CN, —$CF_3$, and an optionally substituted radical selected from the group of —($C_1$-$C_6$)alkyl, aryl;

n is 1;

$B''$ radicals are each independently selected from the group of hydrogen, —$CF_3$, and an optionally substituted radical selected from the group of —($C_1$-$C_6$)alkyl, and —($C_3$-$C_7$)cycloalkyl;

$M^1$ is selected from an optionally substituted 3 to 10 membered ring selected from the group of aryl and heteroaryl; and $M^3$ is hydrogen.

2. A compound according to claim 1 which can exist as optical isomers, wherein said compound is either the racemic mixture or one or both of the individual optical isomers.

3. A compound according to claim 1, wherein said compound is selected from:
4-(3-Methyl-1H-pyrazol-4-yl)-N-phenylthiazol-2-amine,
4-(3-Methyl-1H-pyrazol-4-yl)-N-(pyridin-2-yl)thiazol-2-amine,
N-(Pyridin-2-yl)-4-(3-(trifluoromethyl)-1H-pyrazol-4-yl)thiazol-2-amine; and
4-(3-Isopropyl-1H-pyrazol-4-yl)-N-(pyridin-2-yl)thiazol-2-amine
or a pharmaceutically acceptable acid or base addition salt thereof, a stereochemically isomeric form thereof and an N-oxide form thereof.

4. A compound according to claim 1, wherein said compound is selected from:
N-(2,6-Difluorophenyl)-4-(3-methyl-1H-pyrazol-4-yl)thiazol-2-amine,
5-Methyl-4-(3-methyl-1H-pyrazol-4-yl)-N-(pyridin-2-yl)thiazol-2-amine,
5-Methyl-4-(1H-pyrazol-4-yl)-N-(pyridin-2-yl)thiazol-2-amine,
N-(2,5-Difluorophenyl)-4-(3-methyl-1H-pyrazol-4-yl)thiazol-2-amine,
5-Methyl-N-(6-methylpyridin-2-yl)-4-(1H-pyrazol-4-yl)thiazol-2-amine,
5-Methyl-N-(4-methylpyridin-2-yl)-4-(1H-pyrazol-4-yl)thiazol-2-amine;
N-(3,5-Difluoropyridin-2-yl)-5-methyl-4-(1H-pyrazol-4-yl)thiazol-2-amin;
4-(3-Methyl-1H-pyrazol-4-yl)-N-(4-methylpyridin-2-yl)thiazol-2-amine,
5-Ethyl-4-(1H-pyrazol-4-yl)-N-(pyridin-2-yl)thiazol-2-amine,
4-(3-Methyl-1H-pyrazol-4-yl)-N-(6-methylpyridin-2-yl)thiazol-2-amine, N-(5-Fluoropyridin-2-yl)-5-methyl-4-(1H-pyrazol-4-yl)thiazol-2-amine,
4-(1H-Pyrazol-4-yl)-N-(pyridin-2-yl)thiazol-2-amine,
N-(6-Chloropyridin-2-yl)-5-methyl-4-(1H-pyrazol-4-yl)thiazol-2-amin;
5-Chloro-4-(1H-pyrazol-4-yl)-N-(pyridin-2-yl)thiazol-2-amine,
N-(6-Fluoropyridin-2-yl)-5-methyl-4-(1H-pyrazol-4-yl)thiazol-2-amine,
5-Methyl-N-(pyrazin-2-yl)-4-(1H-pyrazol-4-yl)thiazol-2-amine,
N-(3-Fluoropyridin-2-yl)-5-methyl-4-(1H-pyrazol-4-yl)thiazol-2-amine,
4-(1H-Pyrazol-4-yl)-2-(pyridin-2-ylamino)thiazol-5-carbonitrile,
N-(6-Ethylpyridin-2-yl)-5-methyl-4-(1H-pyrazol-4-yl)thiazol-2-amine,
N-(6-Chloropyridin-2-yl)-4-(1H-pyrazol-4-yl)thiazol-2-amine,
N-(6-Fluoropyridin-2-yl)-4-(1H-pyrazol-4-yl)thiazol-2-amine,
5-Chloro-N-(6-methylpyridin-2-yl)-4-(1H-pyrazol-4-yl)thiazol-2-amin;
N-(6-Methylpyridin-2-yl)-4-(1H-pyrazol-4-yl)thiazol-2-amine,
4-(1H-Pyrazol-4-yl)-N-(pyridin-2-yl)-5-(trifluoromethyl)thiazol-2-amin;
5-Phenyl-4-1H-pyrazol-4-yl)-N-(pyridin-2-yl)thiazol-2-amine,
5-Fluoro-4-(1H-pyrazol-4-yl)-N-(pyridin-2-yl)thiazol-2-amine,
(4-(1H-Pyrazol-4-yl)-2-(pyridin-2-ylamino)thiazol-5-yl)methanol,
N-(6-Methoxypyridin-2-yl)-5-methyl-4-(1H-pyrazol-4-yl)thiazol-2-amin;
4-(3-Cyclopropyl-1H-pyrazol-4-yl)-N-(pyridin-2-yl)thiazol-2-amine; and
4-(3-Ethyl-1H-pyrazol-4-yl)-N-(pyridin-2-yl)thiazol-2-amine or a pharmaceutically acceptable acid or base addition salt thereof, a stereochemically isomeric form thereof and an N-oxide form thereof.

5. A pharmaceutical composition comprising a compound as in any one of claim 1, or 2-4 and a pharmaceutically acceptable carrier and/or excipient.

* * * * *